US012616207B2

(12) United States Patent
Kong

(10) Patent No.: US 12,616,207 B2
(45) Date of Patent: May 5, 2026

(54) **BOXWOOD ENDOPHYTE *BURKHOLDERIA* SP SSG AS POTENTIAL BIOCONTROL AGENT AGAINST A WIDE RANGE OF PATHOGENS**

(71) Applicant: VIRGINIA TECH INTELLECTUAL PROPERTIES, INC., Blacksburg, VA (US)

(72) Inventor: Ping Kong, Virginia Beach, VA (US)

(73) Assignee: VIRGINIA TECH INTELLECTUAL PROPERTIES, INC., Blacksburg, VA (US)

( * ) Notice: Subject to any disclaimer, the term of this patent is extended or adjusted under 35 U.S.C. 154(b) by 625 days.

(21) Appl. No.: 17/905,283

(22) PCT Filed: Mar. 3, 2021

(86) PCT No.: PCT/US2021/020606
§ 371 (c)(1),
(2) Date: Aug. 30, 2022

(87) PCT Pub. No.: WO2021/178496
PCT Pub. Date: Sep. 10, 2021

(65) Prior Publication Data
US 2023/0225329 A1      Jul. 20, 2023

Related U.S. Application Data

(60) Provisional application No. 63/010,644, filed on Apr. 15, 2020, provisional application No. 62/985,165, filed on Mar. 4, 2020.

(51) Int. Cl.
*A01N 63/20*     (2020.01)
*A01P 3/00*      (2006.01)
*C12N 1/20*      (2026.01)

(52) U.S. Cl.
CPC ................ *A01N 63/20* (2020.01); *A01P 3/00* (2021.08); *C12N 1/20* (2013.01)

(58) Field of Classification Search
CPC .............. A01N 63/20; A01P 3/00; C12N 1/20
See application file for complete search history.

(56) References Cited

U.S. PATENT DOCUMENTS 6,524,998 B1     2/2003   Kloepper et al.
2004/0127687 A1  7/2004   Casida, Jr. et al.
(Continued)

OTHER PUBLICATIONS

NCBI Blast. SEQ ID No. 3 and ATCC 25416 Sequence Alignment. (Year: 2025).*

(Continued)

*Primary Examiner* — Jennifer A Berrios
*Assistant Examiner* — Chasity P Janosko
(74) *Attorney, Agent, or Firm* — Thomas | Horstemeyer, LLP

(57)     ABSTRACT

The disclosure, in one aspect, relates to compositions containing non-pathogenic *Burkholderia* species SSG and/or extracts from SSG cultures and methods of making and using the same. Also disclosed are methods for treating and preventing plant diseases caused by pathogens, the methods including applying the disclosed compositions to plants and/or soil, diseased leaf debris, or other plant growth media surrounding the plants. Finally, disclosed are methods for increasing plant growth using the disclosed compositions. The compositions are effective as well as environmentally benign and are not detrimental to human or animal health This abstract is intended as a scanning tool for purposes of searching in the particular art and is not intended to be limiting of the present disclosure.

18 Claims, 19 Drawing Sheets
Specification includes a Sequence Listing.

(56)                        References Cited

U.S. PATENT DOCUMENTS

| 2016/0100587 | A1 | 4/2016 | Bywater-Ekegard et al. |
| 2018/0170819 | A1 | 6/2018 | West et al. |
| 2019/0021337 | A1 | 1/2019 | Von Maltzahn et al. |

OTHER PUBLICATIONS

Kong, P., Evaluation of a novel endophytic Pseudomonas lactis strain for control of boxwood blight. J. Environ. Hort. 37(2), 39-43 (Year: 2019).*
Daligaul T et al. "Whole-Genome Assemblies of 56 *Burkholderia* Species," Genome Announcements, Nov. 20, 2014 (Nov. 20, 2014), vol. 2, No. 6: e01106-14, pp. 1-3. entire document.
International Search Report and Written Opinion for PCT/US2021/020606 mailed Aug. 6, 2021.

* cited by examiner

120

Boxwood cultivar & treatment

BOXWOOD ENDOPHYTE *BURKHOLDERIA* SP SSG AS POTENTIAL BIOCONTROL AGENT AGAINST A WIDE RANGE OF PATHOGENS

CROSS REFERENCE TO RELATED APPLICATIONS

This application is a U.S. national phase application under 35 U.S.C. 371 of International Patent Application No. PCT/US2021/020606, filed Mar. 3, 2021, which claims priority upon U.S. Provisional Application No. 62/985,165, filed on Mar. 4, 2020, and U.S. Provisional Application No. 63/010,644, filed on Apr. 15, 2020.

STATEMENT REGARDING FEDERALLY SPONSORED RESEARCH OR DEVELOPMENT

This invention was made with U.S. Government support under grant numbers 16-8130-0202-CA and 17-8130-0282-CA, and by Specialty Crop Block Grant for Virginia (FFY 2018-586, 301-190934), all awarded by the U.S. Department of Agriculture. The U.S. government has certain rights in the invention.

CROSS REFERENCE TO SEQUENCE LISTING

The genetic components described herein are referred to by sequence identifier numbers (SEQ ID NO). The SEQ ID NOs correspond numerically to the sequence identifiers <400>1, <400>2, etc. The sequence listing in written computer readable format (CRF) as a text file named "222204-1875_Replacement_Sequence_Listing_ST25.txt" created on Jan. 30, 2023 and updated on Mar. 6, 2023, and having a size of 11,144,438 bytes, is incorporated by reference in its entirety.

BACKGROUND

Boxwood (*Buxus*) is a genus of about 70 species in the family Buxaceae. As slow-growing evergreen shrubs and small trees, they are planted worldwide, especially in landscapes and gardens. Boxwood blight is a destructive disease caused by *Calonectria pseudonaviculata* (Cps). In the United States, the disease was first observed and confirmed in North Carolina and Connecticut in 2011 and it has been reported in 30 states as of February 2021. English boxwood (*Buxus sempervirens* 'Suffruticosa'), an iconic plant in American and European landscapes including many historic gardens and plantings, is highly susceptible to this disease. Currently, boxwood protection relies largely on repeated fungicide applications because there are essentially no cultivars that are immune to Cps and eradication of seriously diseased plants results in significant economic loss to the growers and owners. Furthermore, replacing English boxwood in the gardens of royal and historical estates with less susceptible varieties or cultivars is affected by the plants' market and historic values. Cps also attacks several *pachysandra*, sweet box, and potentially some common groundcovers and boxwood companion plants outside of the Buxaceae family.

While chemical control is effective, it is also expensive and potentially a threat to human health and to the environment. Specifically, chlorothalonil, one of the most effective compounds for controlling Cps, has recently been classified as a category one carcinogen and removed from the market in Europe. In addition, the use of fungicides in historic gardens and residential and commercial landscapes is particularly challenging. Economically viable and environmentally sound disease control methods are urgently needed.

Recent studies on mulching and biological control alternatives provided safer and more sustainable management of boxwood blight. Mulching over the infested soil and diseased leaf litter protect plants by effectively preventing pathogen inoculum from splashing onto healthy boxwood foliage. However, this method is powerless to avert transmission above the ground. Two recently identified Cps antagonists, *Trichoderma koningiopsis* from wild mushrooms and *Pseudomonas protegens* from plant nursery recycled irrigation water, have shown potential to be used to reduce disease by about 60%. However, ornamental plants at such protection levels are not marketable.

Plant diseases, including but not limited to boxwood blight, can wipe out entire crops and historical plantings in a short period of time. Globally, plant diseases pose an increasing risk to food security and plant biosecurity. The current approach to disease management depends mainly on chemical protection. This approach is not sustainable due to growing costs, fungicide resistance risk, and human and environmental safety concerns. Managing plant diseases in the environmental horticulture industry is particularly challenging as this industry produces a live commodity that requires the highest level of plant health for aesthetic value. More importantly, this commodity is expected to survive the stresses of shipment, retail, and being planted, then become established at its final destination. Contaminated plants at production facilities may appear healthy without any disease symptoms under intensive chemical protection programs. However, plants may become diseased when they reach their final destinations due to severe stress during shipment, sale, and field establishment, or from lack of continuing chemical protection. There is an urgent need to build a long-term disease-fighting mechanism into horticultural crop products to sustainably safeguard plants.

Endophytes are the microorganisms that reside within the host plant's tissues in a commensal or beneficial manner. Endophytes have received considerable attention for their potential as ideal biocontrol agents because of their ability to suppress plant pathogens and to promote plant growth and yield. Many endophytes that also act as biocontrol agents for plant diseases are also plant growth promoters.

Despite advancements in Cps control research, there is still a lack of biological control agents that are potent, effective, inexpensive, and safe for controlling boxwood blight and other plant diseases caused by bacteria, fungi, viruses, and oomycetes. It would be desirable if the agents were effective both as preventive measures and as post-exposure treatments, were non-pathogenic towards humans, and contributed to increased plant growth. It would further be desirable if the agents served as broad-spectrum biological control strains and additionally acted as a bio-sanitizer as well as a bio-fertilizer enhancing boxwood plant growth. These needs and other needs are satisfied by the present disclosure.

SUMMARY

In accordance with the purpose(s) of the present disclosure, as embodied and broadly described herein, the disclosure, in one aspect, relates to compositions containing non-pathogenic *Burkholderia* species SSG and/or extracts from SSG cultures and methods of making and using the same. Also disclosed are methods for treating and preventing plant diseases caused by pathogens, the methods including applying the disclosed compositions to plants and/or soil, diseased leaf debris, or other plant growth media surrounding the plants. Finally, disclosed are methods for increasing plant growth using the disclosed compositions. The compositions are effective as well as environmentally benign and are not detrimental to human or animal health.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3A. Disease incidence at 50 day after treatment. Each column depicts 18 pot plants from 3 experiments. Bar on the top is the standard error. FIG. 3B. Image of representative pots from treatments at 50 dat. FIG. 3C. Leaves on a branch of the treatment at 50 day after treatment. Each column depicts 12 pot plants from 3 experiments.

FIG. 6A annual *vinca* and *P. nicotianae*. FIG. 6B *rhododendron* and *P. ramorum*. FIG. 6C pepper and *P. capsica*. FIG. 6D tomato and *P. infestans*.

FIG. 7A. Volutella blight on boxwood Green velvet. FIG. 7B. Gray mold on *petunia*. FIG. 7C. Bacterial blight on geranium. FIG. 7D. Tomato spotted wilt virus on *impatiens*.

(FIG. 17A) Color produced at 2 days showing IAA production; (FIG. 17C) Growth on nitrogen free media at 4 days showing nitrogen fixation; (FIG. 17E) Halo produced around disks at 7 days showing phosphate solubilization and (FIG. 17G) Color change at 3 days showing siderophore production. FIGS. 17B, 17D, 17F, and 17H are images of the control tube or plate for FIGS. 17A, 17C, 17E, and 17G, respectively.

Figure 1:
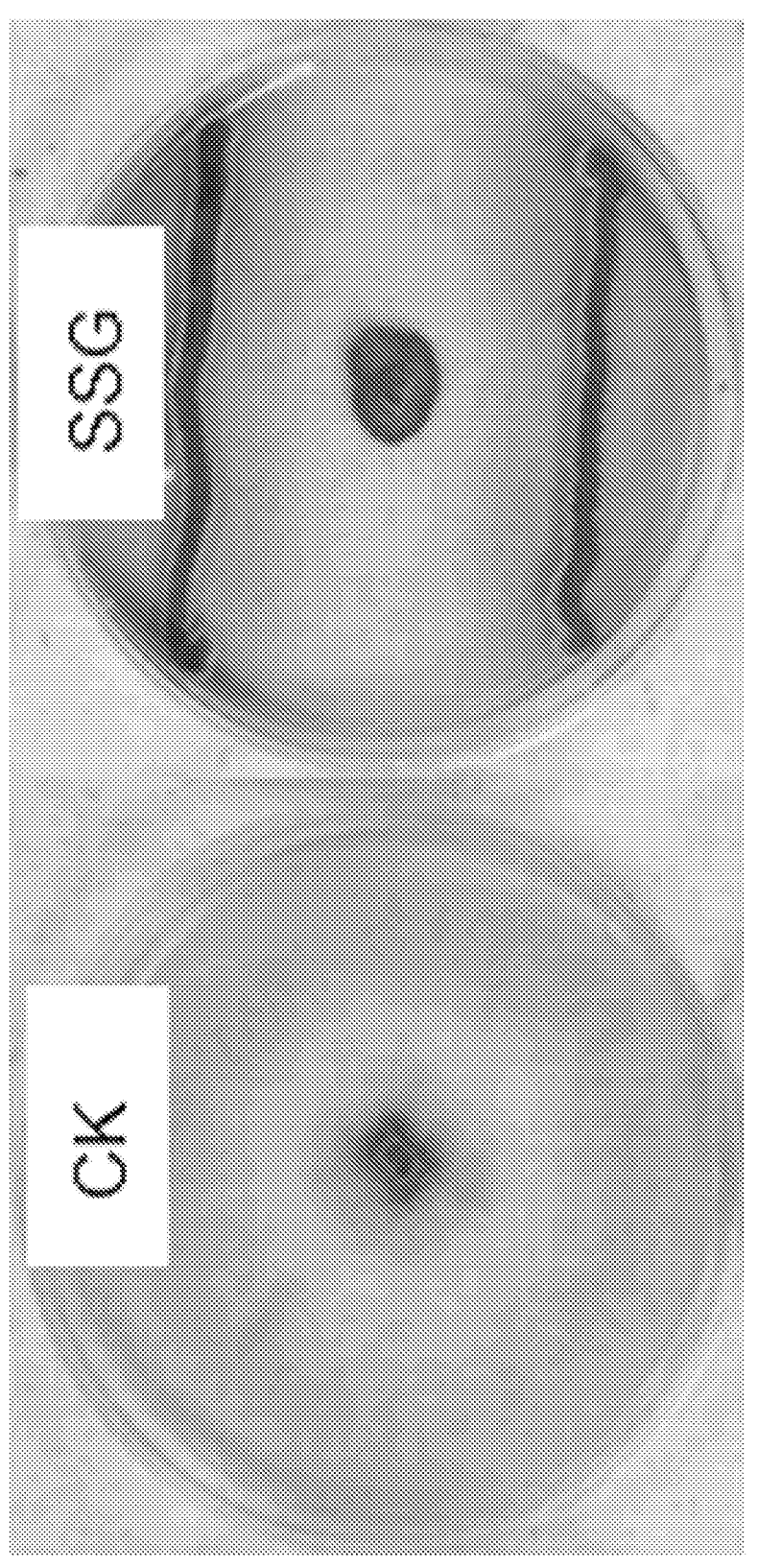
FIG. 1 is a photograph comparing growth of Cps on PDA at 28 days of the assay with nutrient broth (CK) and SSG from boxwood, showing the effects of SSG on *Calonectria pseudonaviculata* (Cps).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are compositions and methods for treating or preventing a plant disease caused by a bacterial, fungal, or *Phytophthora* pathogen, the methods including applying to a plant, a plant growing medium, or diseased leaf debris an effective amount of a composition, wherein the composition includes a microbial strain comprising a DNA sequence exhibiting at least 85% sequence identity to at least one of SEQ ID NOs. 1-6, an extract produced by culturing the microbial strain, or any combination thereof. In a further aspect, the microbial strain can be *Burkholderia cepacia* complex (Bcc) strain SSG.

Also disclosed are compositions methods for increasing plant growth, the methods including applying to a plant or to a plant growing medium an effective amount of a composition, wherein the composition includes a microbial strain comprising a DNA sequence exhibiting at least 85% sequence identity to at least one of SEQ ID NOs. 1-6, an extract produced by culturing the microbial strain, or any combination thereof, so that a treated plant has increased growth compared to an untreated plant. In a further aspect, the microbial strain can be *Burkholderia cepacia* complex (Bcc) strain SSG.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a plant," "a leaf," or "an excipient," includes, but is not limited to, collections, mixtures, or combinations of two or more such plants, leaves, or excipients, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of an active ingredient refers to an amount that is sufficient to achieve the desired improvement in the property modulated by the formulation component, e.g. achieving the desired level of pathogen and/or disease control. The specific level in terms of wt % in a composition required as an effective amount will depend upon a variety of factors including the amount and type of *Burkholderia* metabolites in the composition and/or presence of live cells, amount and type of any carriers or excipients, conditions surrounding the plants to be treated, length of time since treatment and/or number of treatments to be applied, degree of infestation, and identity of the pathogen to be treated.

As used herein, the terms "optional" or "optionally" means that the subsequently described event or circumstance can or cannot occur, and that the description includes instances where said event or circumstance occurs and instances where it does not.

"Inoculum" as used herein refers to a composition containing microorganisms, wherein the composition used to pretreat a plant for the purpose of establishing a population of the microorganisms on the plant. A successful inoculum can be at an active growth stage and size and will generally be free from contamination and may include additional components useful for establishing a population of microorganisms such as, for example, culture medium, solvents, buffers, and the like. In some aspects, a Cps fungal inoculum is prepared to infect plants in order to assess the efficacy of disclosed treatments. In other aspects, an SSG inoculum can be used to treat plants suffering from boxwood blight.

"Colony forming units" (CFU) refers to an estimate of the number of viable microorganisms (e.g., bacteria or fungi) in a sample. In one aspect, number of CFU in a sample can be established by culturing the sample on a plate and counting microbial colonies, wherein each colony is assumed to have arisen from a single cell or group of cells.

As used herein, "conidium" refers to an asexual, non-motile fungal spore. In one aspect, conidia are important reproductive features for Cps. In another aspect, application of the compositions and extracts disclosed herein can interfere with conidium formation and/or germination, or can cause lysis of Cps conidia.

"Microsclerotia" as used herein are resting structures of a fungus such as, for example, Cps. A "*sclerotium*" is a had mass of fungal mycelium that contains some amount of nutritional reserve high in oils and low in moisture and that can survive environmental extremes; a "microsclerotium" is so defined based on relative size.

"Mycelium" as used herein refers to a vegetative body of a fungus composed of branching fungal "hyphae." The hyphae secrete enzymes that can break down biopolymers, the decomposition products of which are then absorbed by the mycelium and used as nutrients.

"Zoospores" are asexual, motile propagules of oomycetes such as *Phytophthora* and *Pythium* species. A zoospore uses a flagellum for locomotion and can additionally be transmitted to uninfected plants by wind, water, and the like. "Sporulation" refers to the formation of spores from vegetative cells during adverse environmental conditions.

"Boxwood blight" refers to a fungal disease of boxwood plants (i.e. *Buxus* species, varieties, and cultivars). Boxwood blight is caused by *Calonectria pseudonaviculata* (Cps), which is also sometimes called *Cylindrocladium buxicola*. *Buxus sempervirens* varieties may be more susceptible to boxwood blight but related species of *Pachysandra* and *Sarcococca* are also susceptible. Boxwood blight is initially found as spots or lesions on leaves, progressing to browning of leaves, which then fall off. Cps zoospores can remain viable for several years in fallen boxwood leaves and can be dispersed by wind, rain, contaminated clothing, animals, and the like. Disclosed herein are methods and compositions for treating and preventing boxwood blight and other diseases caused by plant pathogens.

As used herein, "cell suspension" refers to compositions including un-lysed *Burkholderia cepacia* SSG cells, while "cell free supernatant" refers to solutions produced by centrifugation of an SSG culture suspension followed by filtration of the supernatant to remove any remaining cells.

"Genomovar" as used herein refers to a *Burkholderia* strain that is phenotypically indistinguishable from related *Burkholderia* strains but that can be classified as a species based on DNA sequencing or other biochemical testing.

"Phytopathosystem" refers to a combination of a plant and pathogen. In one aspect, a *Buxus sempervirens* plant infected with Cps is an example of a phytopathosystem.

As used herein, the terms "treating" and "treatment" can refer generally to obtaining a desired physiological effect in a diseased plant. The effect can be, but does not necessarily have to be, prophylactic in terms of preventing or partially preventing a disease, symptom, or condition thereof. The effect can be therapeutic in terms of a partial or complete cure of a disease, condition, symptom or adverse effect attributed to the disease, disorder, or condition. The term "treatment" as used herein can include any treatment of a fungal, bacterial, and/or oomycete infection in a plant, and can include any one or more of the following: (a) preventing the disease from occurring in a plant which may have been exposed to an infected plant; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Plants in need of treatment can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder, and/or condition. Treating the disease, disorder, or condition can include ameliorating at least one symptom of the particular disease, disorder, or condition, even if the underlying pathophysiology is not affected.

As used herein, the term "prevent" or "preventing" refers to precluding, averting, obviating, forestalling, stopping, or hindering a plant disease from infecting a plant or spreading among a plant population, especially by advance action. It is understood that where reduce, inhibit or prevent are used herein, unless specifically indicated otherwise, the use of the other two words is also expressly disclosed. In one aspect, prevention of the plant disease is associated with reduced transmission of the plant disease, either by (i) stopping the spread of the disease from one part of a plant to the rest of the plant or (ii) stopping the spread of the disease from one plant to a nearby plant. Reduced transmission and prevention can be assessed quantitatively based on knowledge in the art such as plant growth habit, conditions for disease spread in a given installation type, and the like, wherein reduced transmission or prevention results in a lower amount of spread of a disease than would ordinarily be expected.

As used herein, "increase" or "increasing" refers to making something greater in size, amount, length, or the like. Thus, in one aspect, a treatment that increases plant growth leads to an improvement in at least one growth-related quality of the plant compared to an untreated plant (e.g., the plant with increased growth is larger in size, has greater foliage area, produces more fruits, or has a longer lifetime than an untreated counterpart).

Unless otherwise specified, temperatures referred to herein are based on atmospheric pressure (i.e. one atmosphere).

Microbial Compositions and Extracts

In one aspect, disclosed herein are compositions including a microbial strain that has a DNA sequence exhibiting from about 85% to about 100% sequence identity to at least one of SEQ ID NOs. 1-6, or at least 85, 86, 87, 88, 89, 90, 91, 92, 93, 94, 95, 96, 97, 98, 99, 99.5, or 100% sequence identity to at least one of SEQ ID NOs. 1-6, or a combination of any of the foregoing values, or a range encompassing any of the foregoing values. In one aspect, SEQ ID NOs. 1-6 represent contigs of the genome sequence of SSG. Further in this aspect, SEQ ID NOs. 1-6 can be assembled in a sequential order to identify or elucidate one or more portions of the genome of SSG.

In another aspect, the microbial strain can be a *Burkholderia cepacia* complex (Bcc) member. In a further aspect, the Bcc member can be an epidemic strain marker-negative strain (i.e. does not cause negative effects with respect to human health in either healthy or immunocompromised individuals). In some aspects, the Bcc member is referred to herein as SSG.

In another aspect, the microbial strain can be frozen, lyophilized, or present as metabolically active cells. In one aspect, the microbial strain is present in the composition in an amount of from about $10^9$ to about $10^3$ colony forming units (CFU) per mL, or at about $10^9$, $10^8$, $10^7$, $10^6$, $10^5$, $10^4$, or about $10^3$ CFU/mL, or a combination of any of the foregoing values, or a range encompassing any of the foregoing values.

In yet another aspect, disclosed herein are extracts produced by culturing the disclosed microbial strains and/or microbial compositions. In one aspect, the extracts are substantially free of microbial cells. In another aspect, the extracts can be produced by (a) culturing the microbial strain in a culture medium and (b) filtering the culture medium. In one aspect, the culture medium can be filtered with a 0.22 μm filter Excipients, Diluents, Carriers, and Additional Active Ingredients In any of these aspects, the compositions further include at least one excipient, diluent, or carrier, or any combination thereof. In another aspect, the at least one excipient, diluent, or carrier can be a surfactant, a solvent, an emulsifier, a buffer, a cryoprotectant, a salt, microbial culture medium, a wetting agent, a bulking agent, an anti-caking agent, a thickener, a clay, a mineral, a lipid, a gum, a dye or colorant, a biological waste material, or any combination thereof. In some aspects, one compound or component can fit in different categories (e.g., a clay can also act as a thickener and/or a bulking agent, or a salt may also have buffering properties and/or act as a cryoprotectant, and the like).

In one aspect, the cryoprotectant can be ethylene glycol, propylene glycol, glycerol, dimethyl sulfoxide, sucrose, trehalose, or any combination thereof.

In one aspect, the clay can be a natural clay, a clay mineral, or a natural or synthetic silicate salt. In a further aspect, the clay can be selected from aluminum magnesium silicate, aluminum potassium sodium silicate, aluminum silicate, aluminum sodium silicate, attapulgite-type clay, bentonite, calcium oxide silicate, calcium silicate, Fuller's earth, kaolin, magnesium oxide silicate, magnesium silicate, magnesium silicate hydrate, montmorillonite, perlite, potassium aluminum silicate, vermiculite, wollastonite, zeolites, or any combination thereof.

In another aspect, the salt can be a salt, buffer, or any combination thereof. In one aspect, the salt can be calcium acetate, calcium citrate, calcium sulfate, citric acid, dipotassium citrate, disodium citrate, disodium sulfate, ferric oxide, ferrous oxide, iron magnesium oxide, magnesium carbonate, magnesium oxide, magnesium sulfate, potassium acetate, potassium bicarbonate, potassium chloride, potassium citrate, potassium sulfate, sodium acetate, sodium bicarbonate, sodium chloride, sodium citrate, sodium sulfate, zinc iron oxide, zinc oxide, zinc stearate, hydrates thereof, conjugate acids and/or bases thereof, and any combination thereof.

In another aspect, the mineral can be calcium carbonate, feldspar, granite, graphite, gypsum, hematite, lime, limestone, mica, mica-group minerals, nepheline syenite, pumice, shale, or any combination thereof.

In one aspect, the lipid can be one or more waxes, one or more acylglycerols, one or more triglycerides, one or more diglycerides, one or more monoglycerides, one or more fatty acids, one or more steroids, or any combination thereof. Examples of useful lipids include, but are not limited to, tristearin, glycerol behenate, glycerol monostearate, stearic acid, cholesterol, cetyl palmitate, and combinations thereof. In another aspect, the lipid can further function as an emulsifier, surfactant, detergent, wetting agent, foaming agent, dispersant, or any combination thereof.

In one aspect, the dye or colorant can be selected from chlorophyll, red cabbage color, ultramarine blue, or any combination thereof.

In another aspect, the thickener can be agar, carrageenan, or any combination thereof. In another aspect, the wax can be beeswax, carnauba wax, paraffin wax, or any combination thereof. In still another aspect, the gum can be locust bean gum, gellan gum, guar gum, gum arabic, gum tragacanth, xanthan gum, or any combination thereof.

In one aspect, the biological waste material can be almond hulls, almond shells, bone meal, bran, bread crumbs, cardboard, cellulose or a chemically-modified cellulose, citrus meal, citrus pulp, clam shells, cocoa, cocoa shell flour, cocoa shells, coffee grounds, cork, corn cobs, cracked wheat, diatomaceous earth, Douglas fir bark, egg shells, fish meal, peanut shells, peat moss, red cedar chips, sawdust, soybean hulls, soybean meal, soybean flour, walnut flour, walnut shells, wheat, or any combination thereof.

In some aspects, the surfactant can be a polysorbate such as, for example, polysorbate 20. In another aspect, the solvent can be water. In one aspect, the at least one excipient, diluent, or carrier can confer increased stability, wettability, dispersibility, or adherence to a substrate relative to a composition lacking the carrier.

In one aspect, the composition can be or include an emulsion, colloid, granule, pellet, powder, spray, suspension, or solution.

In another aspect, the composition can further include at least one additional active ingredient. In a further aspect, the additional active ingredient can be a fertilizer, a pesticide, an herbicide, or any combination thereof.

Method for Treating or Preventing Plant Disease

In one aspect, disclosed herein is a method for treating or preventing a plant disease caused by a pathogen, the method including applying the disclosed compositions to a plant. In another aspect, the composition can be applied from about 2 days to about 30 days prior to exposure to the pathogen, or can be applied 2, 3, 4, 5, 6, 7, 8, 9, 10, 11, 12, 13, 14, 15, 16, 17, 18, 19, 20, 21, 22, 23, 24, 25, 26, 27, 28, 29, or about 30 days prior to exposure to the pathogen, or a combination of any of the foregoing values, or a range encompassing any of the foregoing values. In one aspect, the composition is applied 2, 10, 20, or 30 days prior to exposure to the pathogen. In an alternative aspect, the composition can be applied from about 3 hours to about 48 hours following exposure to the pathogen, or can be applied at 2, 6, 9, 12, 15, 18, 21, 24, 27, 30, 33, 36, 39, 42, 45, or about 48 hours following exposure to the pathogen, or a combination of any of the foregoing values, or a range encompassing any of the foregoing values. In one aspect, the composition is applied 3, 24, or 48 hours after exposure to the pathogen.

In another aspect, applying the composition to a plant about 1 day prior to exposure to or inoculation with a pathogen reduces at least one symptom of a plant disease by about 99%. In another aspect, applying the composition to a plant about 30 days prior to exposure to the pathogen reduces at least one symptom of a disease by from about 30% to about 75%, or by about 30, 35, 40, 45, 50, 55, 60, 65, 70, or about 75%, or a combination of any of the foregoing values, or a range encompassing any of the foregoing values. In some aspects, the at least one symptom can be blight.

In one aspect, disclosed herein is a method for treating or preventing a plant disease caused by a pathogen, the method including applying the disclosed compositions to at least one environmental component of a plant. In another aspect, the environmental component can be leaf debris, soil, the plant's rhizosphere, a potting or bedding material as disclosed herein, or any combination thereof. About 5 days after treatment with the disclosed compositions and/or extracts, primary inocula (e.g., conidia, microsclerotia) can be reduced by at least about 30%. In still another aspect, about 30 days following treatment with the disclosed compositions and/or extracts, primary inocula can be reduced by at least about 75%. In a still further aspect, treatment with the disclosed compositions and/or methods can remain effective for at least 50 days.

In one aspect, the pathogen can be a bacterium, a fungus, or an oomycete. In a further aspect, when the pathogen is a bacterium, the bacterium can include, but is not limited to, *Escherichia coli*, *Erwinia carotovora*, *Pseudomonas syringae*, *Ralstonia solanacearum*, *Stenotrophomonas maltophilia*, or *Xanthomonas campestris*.

In another aspect, when the pathogen is a fungus, the fungus can include, but is not limited to, *Calonectria pseudonaviculata*, *Alternaria* tenuissium, *Botrytis cinerea*, *Collectortrichum acutatum*, Collectortrichum frutticola, Collectortrichum gleosporiodes, Collectortrichum *viniferum*, *Fusarium* proliferaturm, *Fusarium solani*, or *Volutella buxi*.

In still another aspect, when the pathogen is an oomycete, the pathogen can be a *Phytophthora* species such as, for example, P. *capsica*, P. *cinnamomi*, P. *infestans*, P. *nicotianae*, P. *ramorum*, or P. *sojae*.

In one aspect, the plant can be an ornamental plant, a food plant, an energy crop, a fiber crop, a timber crop, or any combination thereof. In still another aspect, the composition can be applied to the roots, leaves, fruits, flowers, stems, or seeds of the plant, or any combination thereof. In an alternative aspect, the composition can be applied to soil, compost, mulch, leaf litter, sawdust, straw, pine straw, wood chips, gravel, plant growing medium, or other material in a bed surrounding the plant.

In one aspect, the plant can be Fraser fir (*Abies fraseri*), petunia (*Petuniaxhybrida*), rhododendron (*Rhododendron catawbiense*), annual *vinca* (*Catharanthus roseus*), bell pepper (*Capsicum annuum*), cucumber (*Cucumis sativus*), tomato (*Solanum lycopersicum*), hydrangea (*Hydrangea* paniculate), pansy (*Viola tricolor* var. *hortensis*), boxwood (*Buxus* semipervirens), geranium (*Pelargonium* spp.), or *impatiens* (*Impatiens walleriana*), or another species, variety, cultivar, or hybrid thereof. In one aspect, the fungus is *Calonectria pseudonaviculata* (Cps) and the plant is boxwood.

In one aspect, performing the method reduces at least one symptom of the plant disease by from at least 50% to 100%, or by at least 50, 55, 60, 65, 70, 75, 80, 85, 90, 95, 99, 99.5, or 100%, or a combination of any of the foregoing values, or a range encompassing any of the foregoing values. In one aspect, performing the method reduces at least one symptom of the plant disease by at least 50, 65, 90, or 99%.

In another aspect, the at least one symptom can be leaf yellowing, leaf loss, wilting, dwarfing or hypoplasia, gall formation, mycelium or mold growth, smuts, rusts, sclerotia, tissue necrosis, cankers, blight, rot, hypertrophy, or any combination thereof.

In one aspect, performing the method reduces transmission of the plant disease by from at least 50% to 100%, or by at least 50, 55, 60, 65, 70, 75, 80, 85, 90, 95, 99, 99.5, or 100%, or a combination of any of the foregoing values, or a range encompassing any of the foregoing values. In one aspect, performing the method reduces transmission of the plant disease by at least 65, 90, or 99%. In a further aspect, rates of transmission of various plant diseases are known or can be estimated by those knowledgeable in the art based on conditions such as, for example, in a nursery or landscape installation when a diseased plant is introduced. Further in this aspect, reduction of transmission can be calculated following application of the compositions and methods disclosed herein by visually inspecting surrounding plants for symptoms of plant disease such as those discussed herein. Rates of transmission among untreated plants can then be compared to rates of transmission among treated plants and a percentage or amount of reduction can be calculated.

In some aspects, the plant pathogen can be a fungus and performing the method lyses at least a portion of fungal conidia, causes defects in formed fungal conidia, suppresses mycelial growth, reduces survival of fungal microsclerotia, reduces sporulation, or any combination thereof.

In one aspect, disclosed herein is a method for treating or preventing a plant disease caused by a pathogen, the method including at least the step of applying to a plant or to a plant growing medium an effective amount of a composition, wherein the composition includes a microbial strain having a DNA sequence exhibiting at least 85% sequence identity to at least one of SEQ ID NOs. 1-6, an extract produced by culturing the microbial strain, or any combination thereof. In a further aspect, the plant disease can be boxwood blight. Also disclosed are plants treated using the disclosed methods. In another aspect, the DNA sequence can have at least 85, 86, 87, 88, 89, 90, 91, 92, 93, 94, 95, 96, 97, 98, 99, 99.5, or 100% sequence identity to at least one of SEQ ID NOs. 1-6, a combination of any of the foregoing values, or a range encompassing any of the foregoing values.

Method for Increasing Plant Growth

In one aspect, disclosed herein is a method for increasing plant growth, the method including applying the disclosed compositions to a plant so that the treated plant has increased growth compared to an untreated plant. In a further aspect, the plant can be an ornamental plant, a food plant, an energy crop, a fiber crop, a timber crop, or any combination thereof. In another aspect, the composition can be applied to the roots, leaves, fruits, flowers, stems, or seeds of the plant, or any combination thereof. In still another aspect, the composition can be applied to soil, compost, mulch, leaf litter, sawdust, straw, pine straw, wood chips, gravel, plant growing medium, or other material in a bed surrounding the plant.

In one aspect, performing the method can deliver an increased amount of an auxin to the treated plant compared to an untreated plant. In one aspect, the auxin can be indole-3-acetic acid (IAA). In another aspect, performing the method increases the amount of nitrogen available to the treated plant compared to an untreated plant. In yet another aspect, performing the method increases the amount of soluble phosphate available to the treated plant compared to an untreated plant. In still another aspect, performing the method increases the concentration of siderophores available to the treated plant compared to an untreated plant.

In one aspect, the plant can be Fraser fir, *petunia, rhododendron*, annual *vinca*, bell pepper, cucumber, tomato, *hydrangea*, pansy, boxwood, geranium, or *impatiens*.

In another aspect, increasing plant growth can result in increased biomass of the treated plant compared to an untreated plant. In another aspect, increasing plant growth can result in increased fruit production of the treated plant compared to an untreated plant. In still another aspect, increasing plant growth can lead to increased production period of the treated plant compared to an untreated plant, or to an increased productive lifespan of the treated plant compared to an untreated plant. In yet another aspect, increasing plant growth can result in an increased foliage area of the treated plant compared to an untreated plant, wherein increased foliage area can include a greater number of leaves, a larger surface area per individual leaf, or any combination thereof. In one aspect, plant growth can be increased by from at least 35% to at least 75% compared to an untreated plant, or by about 35, 40, 45, 50, 55, 60, 65, 70, or about 75% compared to an untreated plant, or a combination of any of the foregoing values, or a range encompassing any of the foregoing values. In one aspect, plant growth increase by about 35%, about 55%, or about 75% compared to an untreated plant.

In still another aspect, disclosed herein is a method for increasing plant growth, the method including the steps of applying to a plant or to a plant growing medium an effective amount of a composition, wherein the composition includes a microbial strain that includes a DNA sequence exhibiting at least 85% sequence identity to at least one of SEQ ID NOs. 1-6, an extract produced by culturing the microbial strain, or any combination thereof, so that a treated plant has increased growth compared to an untreated plant. In another aspect, the DNA sequence can have from about 85% to about 100% sequence identity to at least one of SEQ ID NOs. 1-6, or about 85, 86, 87, 88, 89, 90, 91, 92, 93, 94, 95, 96, 97, 98, 99, 99.5, or about 100% sequence identity, or a combination of any of the foregoing values, or a range encompassing any of the foregoing values. Also disclosed are plants treated by the disclosed methods.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Aspects

The present disclosure can be described in accordance with the following numbered Aspects, which should not be confused with the claims.

Aspect 1. A composition comprising a microbial strain comprising a DNA sequence exhibiting at least 85% sequence identity to at least one of SEQ ID NOs. 1-6 and at least one excipient, diluent, or carrier.

Aspect 2. The composition of aspect 1, wherein the DNA sequence exhibits at least 90% sequence identity to at least one of SEQ ID NOs. 1-6.

Aspect 3. The composition of aspect 1, wherein the DNA sequence exhibits at least 95% sequence identity to at least one of SEQ ID NOs. 1-6.

Aspect 4. The composition of aspect 1, wherein the DNA sequence exhibits at least 99% sequence identity to at least one of SEQ ID NOs. 1-6.

Aspect 5. The composition of aspect 1, wherein the DNA sequence exhibits at least 99.5% sequence identity to at least one of SEQ ID NOs. 1-6.

Aspect 6. The composition of any one of aspects 1-5, wherein, in the composition, the microbial strain is frozen, lyophilized, or is present as metabolically active cells.

Aspect 7. The composition of any one of aspects 1-6, wherein, in the composition, the microbial strain is present in an amount of from about $10^9$ to about $10^3$ colony forming units per mL.

Aspect 8. The composition of any one of aspects 1-6, wherein, in the composition, the microbial strain is present in an amount of from about $10^9$ to about $10^8$ colony forming units per mL.

Aspect 9. The composition of any of aspects 1-8, wherein the at least one excipient, diluent, or carrier confers increased stability, wettability, dispersibility, or adherence to a substrate relative to a composition lacking the carrier.

Aspect 10. An extract produced by culturing a microbial strain comprising a DNA sequence exhibiting at least 85% sequence identity to at least one of SEQ ID NOs. 1-6.

Aspect 11. The extract of aspect 10, wherein the DNA sequence exhibits at least 90% sequence identity to at least one of SEQ ID NOs. 1-6.

Aspect 12. The extract of aspect 10, wherein the DNA sequence exhibits at least 95% sequence identity to at least one of SEQ ID NOs. 1-6.

Aspect 13. The extract of aspect 10, wherein the DNA sequence exhibits at least 99% sequence identity to at least one of SEQ ID NOs. 1-6.

Aspect 14. The extract of aspect 10, wherein the DNA sequence exhibits at least 99.5% sequence identity to at least one of SEQ ID NOs. 1-6.

Aspect 15. The extract of any one of aspects 10-14, wherein the extract is substantially free of microbial cells.

Aspect 16. The extract of any one of aspects 10-15, wherein the extract is produced by:
(a) culturing the microbial strain in a culture medium; and
(b) filtering the culture medium.

Aspect 17. A composition comprising the extract of any one of aspects 10-16 and at least one excipient, diluent, or carrier.

Aspect 18. The composition of any one of aspects 1-9 or 17, wherein the composition comprises an emulsion, a colloid, a granule, a pellet, a powder, a spray, a suspension, or a solution.

Aspect 19. The composition of any one of aspects 1-9, 17, or 18, wherein the at least one excipient, diluent, or carrier comprises a surfactant, a solvent, an emulsifier, a buffer, a cryoprotectant, a salt, microbial culture medium, a wetting agent, a bulking agent, an anti-caking agent, a thickener, a clay, a mineral, a wax, a gum, a dye or colorant, a biological waste material, or any combination thereof.

Aspect 20. The composition of aspect 19, wherein the surfactant comprises polysorbate 20.

Aspect 21. The composition of aspect 19, wherein the solvent comprises water.

Aspect 22. The composition of any one of aspects 1-9 or 17-21, wherein the composition further comprises an effective amount of at least one additional active ingredient.

Aspect 23. The composition of aspect 22, wherein the additional active ingredient comprises a fertilizer, a pesticide, an herbicide, or any combination thereof.

Aspect 24. The composition of any of aspects 17-23, wherein the at least one excipient, diluent, or carrier confers increased stability, wettability, dispersibility, or adherence to a substrate relative to a composition lacking the carrier.

Aspect 25. A method for treating or preventing a plant disease caused by a pathogen, the method comprising applying the composition of any one of aspects 1-9 or 17-24 to a plant.

Aspect 26. The method of aspect 25, wherein the composition is applied from about 2 to about 30 days prior to exposure to the pathogen.

Aspect 27. The method of aspect 25, wherein the composition is applied from about 3 hours to about 48 hours after exposer to the pathogen.

Aspect 28. The method of any one of aspects 25-27, wherein applying the composition about 1 day prior to exposure to the pathogen reduces at least one symptom of a disease by about 99%.

Aspect 29. The method of any one of aspects 25-27, wherein applying the composition about 30 days prior to exposure to the pathogen reduces at least one symptom of a disease by from about 30% to about 75%.

Aspect 30. The method of aspect 28 or 29, wherein the at least one symptom comprises blight.

Aspect 31. A method for treating or preventing a plant disease caused by a pathogen, the method comprising applying the composition of any one of aspects 1-9 or 17-24 to at least one environmental component of a plant.

Aspect 32. The method of aspect 31, wherein the at least one environmental component comprises leaf debris, soil, the plant's rhizosphere, or any combination thereof.

Aspect 33. The method of any one of aspects 25-27, wherein applying the composition reduces primary inocula by at least 30% after 5 days.

Aspect 34. The method of aspect 31 or 32, wherein applying the composition reduces primary inocula by at least 75% after 30 days.

Aspect 35. The method of any one of aspects 31-34, wherein applying the composition reduces primary inocula for a period of at least 50 days.

Aspect 36. The method of any one of aspects 25-35, wherein the pathogen comprises a bacterium, a fungus, an oomycete, or a virus.

Aspect 37. The method of aspect 36, wherein the bacterium comprises *Escherichia coli*, *Erwinia carotovora*, *Pseudomonas syringae*, *Ralstonia solanacearum*, *Stenotrophomonas maltophilia*, or *Xanthomonas campestris*.

Aspect 38. The method of aspect 36, wherein the fungus comprises *Calonectria pseudonaviculata*, *Alternaria* tenuissium, *Botrytis cinerea*, *Collectortrichum acutatum*, Collectortrichum frutticola, Collectortrichum gleosporiodes, Collectortrichum *viniferum*, *Fusarium* proliferaturm, *Fusarium solani*, or *Volutella buxi*.

Aspect 39. The method of aspect 36, wherein the oomycete comprises a *Phytophthora* species.

Aspect 40. The method of aspect 39, wherein the *Phytophthora* species comprises P. *capsica*, *P. cinnamomi*, *P. infestans*, *P. nicotianae*, *P. ramorum*, or *P. sojae*.

Aspect 41. The method of aspect 36, wherein the virus comprises a tospovirus or tomato spotted wilt virus.

Aspect 42. The method of any one of aspects 25-41, wherein the plant comprises an ornamental plant, a food plant, an energy crop, a fiber crop, a timber crop, or a combination thereof.

Aspect 43. The method of any one of aspects 25-42, wherein the composition is applied to the roots, leaves, fruits, flowers, stems, or seeds of the plant, or any combination thereof.

Aspect 44. The method of any one of aspects 25-43, wherein the composition is applied to soil, compost, mulch, leaf litter, sawdust, straw, pine straw, wood chips, gravel, plant growing medium, or other material in a bed surrounding the plant.

Aspect 45. The method of any one of aspects 25-44, wherein the plant comprises Fraser fir, *petunia, rhododendron*, annual *vinca*, bell pepper, cucumber, tomato, *hydrangea*, pansy, boxwood, geranium, or *impatiens*.

Aspect 46. The method of aspect 45, wherein the fungus comprises *Calonectria pseudonaviculata* and the plant comprises boxwood.

Aspect 47. The method of any one of aspects 25-46, wherein performing the method reduces at least one symptom of the plant disease by at least 50%.

Aspect 48. The method of any one of aspects 25-46, wherein performing the method reduces at least one symptom of the plant disease by at least 65%.

Aspect 49. The method of any one of aspects 25-46, wherein performing the method reduces at least one symptom of the plant disease by at least 90%.

Aspect 50. The method of any one of aspects 25-46, wherein performing the method reduces at least one symptom of the plant disease by at least 99%.

Aspect 51. The method of any one of aspects 42-50, wherein the at least one symptom comprises leaf yellowing, leaf loss, wilting, dwarfing or hypoplasia, gall formation, mycelium or mold growth, smuts, rusts, sclerotia, tissue necrosis, cankers, blight, rot, hypertrophy, or any combination thereof.

Aspect 52. The method of any one of aspects 25-46, wherein performing the method reduces transmission of the plant disease by at least 50%.

Aspect 53. The method of any one of aspects 25-46, wherein performing the method reduces transmission of the plant disease by at least 65%.

Aspect 54. The method of any one of aspects 25-46, wherein performing the method reduces transmission of the plant disease by at least 90%.

Aspect 55. The method of any one of aspects 25-46, wherein performing the method reduces transmission of the plant disease by at least 99%.

Aspect 56. The method of any one of aspects 25-36, 38, or 42-55, wherein the plant pathogen is a fungus and wherein performing the method lyses at least a portion of fungal conidia, causes defects in formed fungal conidia, suppresses mycelial growth, reduces survival of fungal microsclerotia, reduces sporulation, or any combination thereof.

Aspect 57. A method for treating or preventing a plant disease caused by a pathogen, the method comprising applying to a plant or to a plant growing medium an effective amount of a composition, wherein the composition comprises a microbial strain comprising a DNA sequence exhibiting at least 85% sequence identity to at least one of SEQ ID NOs. 1-6, an extract produced by culturing the microbial strain, or any combination thereof.

Aspect 58. The method of aspect 57, wherein the plant disease comprises boxwood blight.

Aspect 59. A plant treated using the method of any one of aspects 25-53.

Aspect 60. A method for increasing plant growth, the method comprising applying the composition of any one of aspects 1-9 or 17-21 to a plant, so that a treated plant has increased growth compared to an untreated plant.

Aspect 61. The method of aspect 60, wherein the plant comprises an ornamental plant, a food plant, an energy crop, a fiber crop, a timber crop, or a combination thereof.

Aspect 62. The method of aspect 60 or 61, wherein the composition is applied to the roots, leaves, fruits, flowers, stems, or seeds of the plant, or any combination thereof.

Aspect 63. The method of any one of aspects 60-62, wherein the composition is applied to soil, compost, mulch, leaf litter, sawdust, straw, pine straw, wood chips, gravel, plant growing medium, or other material in a bed surrounding the plant.

Aspect 64. The method of any one of aspects 60-63, wherein performing the method delivers an increased amount of an auxin to the treated plant compared to an untreated plant.

Aspect 65. The method of aspect 64, wherein the auxin comprises indole-3-acetic acid.

Aspect 66. The method of any one of aspects 60-65, wherein performing the method increases an amount of nitrogen available to the treated plant compared to an untreated plant.

Aspect 67. The method of any one of aspects 60-66, wherein performing the method increases an amount of soluble phosphate available to the treated plant compared to an untreated plant.

Aspect 68. The method of any one of aspects 60-67, wherein performing the method increases a concentration of siderophores available to the treated plant compared to an untreated plant.

Aspect 69. The method of any one of aspects 60-68, wherein the plant comprises Fraser fir, *petunia, rhododendron,* annual *vinca,* bell pepper, cucumber, tomato, *hydrangea,* pansy, boxwood, geranium, or *impatiens.*

Aspect 70. The method of any one of aspects 60-69, wherein increasing plant growth comprises increased biomass of the treated plant compared to an untreated plant.

Aspect 71. The method of any one of aspects 60-70, wherein increasing plant growth comprises increased fruit production of the treated plant compared to an untreated plant.

Aspect 72. The method of any one of aspects 60-71, wherein increasing plant growth comprises increased production period of the treated plant compared to an untreated plant.

Aspect 73. The method of any one of aspects 60-72, wherein increasing plant growth comprises increased productive lifespan of the treated plant compared to an untreated plant.

Aspect 74. The method of any one of aspects 60-73, wherein increasing plant growth comprises increased foliage area of the treated plant compared to an untreated plant.

Aspect 75. The method of aspect 74, wherein increased foliage area comprises a greater number of leaves, a larger surface area per individual leaf, or any combination thereof.

Aspect 76. The method of any one of aspects 60-75, wherein performing the method increases plant growth by at least 35% for an untreated plant compared to an untreated plant.

Aspect 77. The method of any one of aspects 60-76, wherein performing the method increases plant growth by at least 55% for an untreated plant compared to an untreated plant.

Aspect 78. The method of any one of aspects 60-77, wherein performing the method increases plant growth by at least 75% for an untreated plant compared to an untreated plant.

Aspect 79. A method for increasing plant growth, the method comprising applying to a plant or to a plant growing medium an effective amount of a composition, wherein the composition comprises a microbial strain comprising a DNA sequence exhibiting at least 85% sequence identity to at least one of SEQ ID NOs. 1-6, an extract produced by culturing the microbial strain, or any combination thereof, so that a treated plant has increased growth compared to an untreated plant Aspect 80. A plant treated using the method of any one of aspects 60-79.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Materials and Methods for Assessment of Control of Boxwood Blight

SSG Isolation, Growth Conditions, Cell Suspension, and Cell Free Supernatant (CFS)

Figure 4:
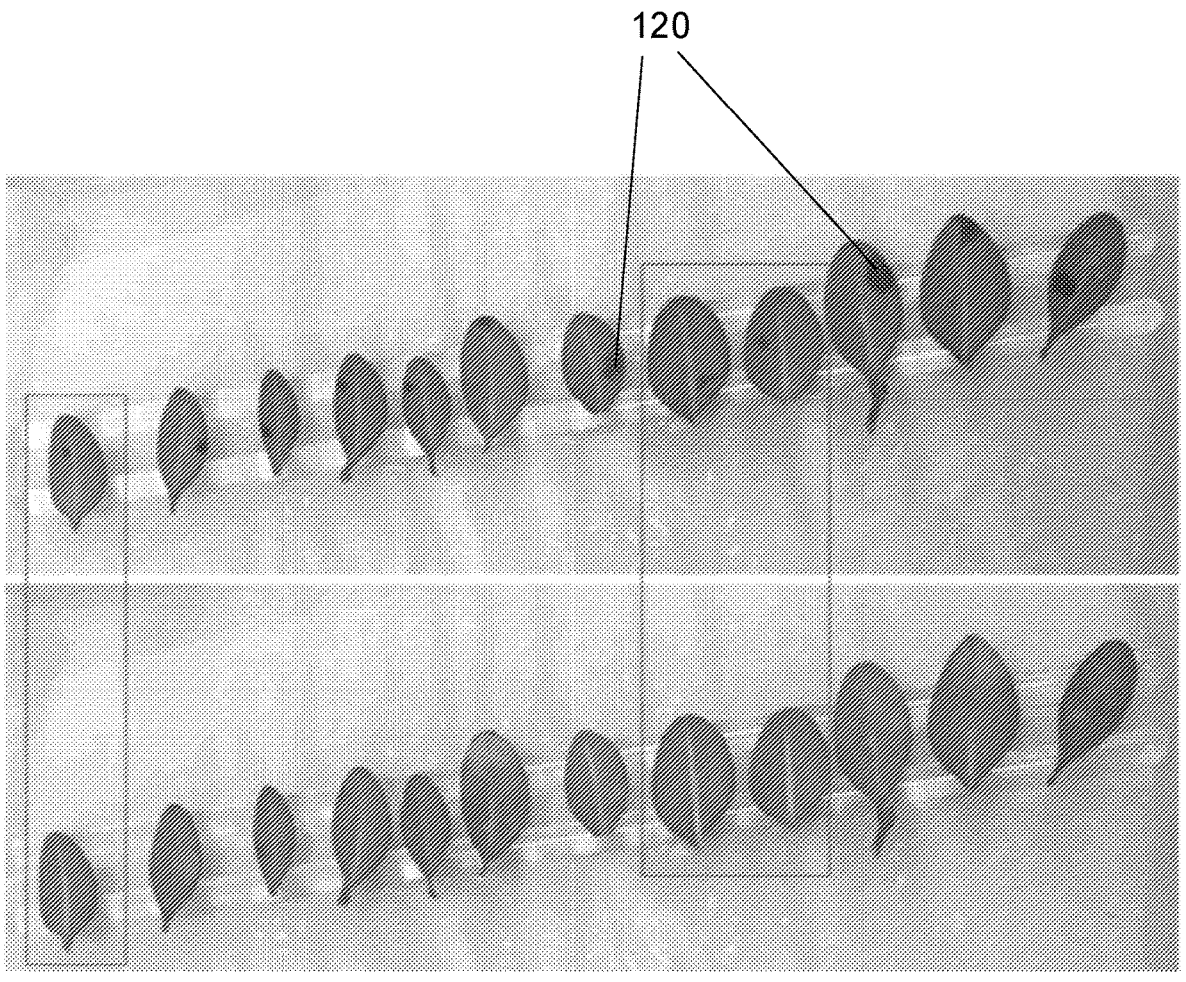
FIG. 4 shows changes (reversion of symptoms) at inoculation sites on detached boxwood leaves after receiving a drop containing conidia of *Calonectria pseudonaviculata*. Top. Water-soaked lesion appeared on individual leaves 2 days after inoculation (dpi). Bottom. Water-soaked lesions disappeared from three leaves (in rectangle) while progressing to show blight symptoms and signs on other leaves at 7 dpi.

In an experiment, individual detached leaves of *Buxus sempervirens* 'Justin Brouwers' were inoculated with a drop of conidia suspensions of *Calonectria pseudonaviculata* (Cps) and water-soaked lesions appeared at two days post inoculation (dpi). While lesions on most of these leaves expanded by 7 dpi, a few disappeared (FIG. 4). SSG was isolated from the symptom reversed leaves. These leaves were surface sterilized with 70% ethanol, cut into small pieces, and vortexed in sterile deionized water (SDW) for 10 min. The supernatant was plated on potato dextrose agar (PDA, Sigma-Aldrich, St. Louis, MO, USA) after brief precipitation by gravity and grown for 48 h at 25° C. To isolate SSG, colonies on the plates were grouped and subjected to selection by dual culture assay against Cps.

SSG was grown in 4 mL nutrient broth (Sigma-Aldrich, St. Louis, MO, USA) at 28° C. for 24 h as a stock culture for long-term storage at −80° C., for short-term storage at 4° C., as streak culture on nutrient agar, and other uses. For fresh stock culture preparation, a single colony was taken from the plate and grown in PD broth or nutrient broth overnight at 28° C. To make a large amount of culture, 1 mL of the stock culture was grown in 150 mL for 40 h. The culture was centrifuged at $14210\times g$ for 15 min to suspend the pellet for preparation of cell suspensions and to pass the supernatant through a 0.22 μm-filter for preparation of cell-free supernatant (CFS).

Growth Conditions of Cps and Conidial Inoculum Preparation

A Cps isolate, Sb1, from sweet box (*Sarcococca hookeriana* var. *humilis*) was used. The isolate was grown at 25° C. and maintained at 20° C. on PDA as described previously. The conidia for plant inoculation was produced using a liquid culture in PD broth which produced a high concentration of inocula as described in the literature. Conidia were suspended in 0.01% polysorbate 20, and the concentration of conidial suspensions was determined with a hemocytometer.

Dual Culture Assays on Antagonism of the Isolates

Dual-culture assays were conducted in 90-mm PDA plates. A mycelial plug of the Cps was placed in the center of the plate and equidistantly surrounded with two streaks of the control (nutrient broth) and a 24 h-culture of a test bacterial isolate in nutrient broth (FIG. 1). For each test bacterial isolate, the assay included three replicate plates and was repeated twice. All plates were incubated at 25° C. in the dark. Cps colony growth diameters were measured at 1, 2 and 4 weeks.

Microscopy of Effects of SSG on Cps Conidia Morphogenesis

A time-course assay was conducted in 24-well plates to determine the effects of SSG on Cps conidia survival, germination and differentiation. In each three replicate wells, 100 μL of Cps suspension at $10^4$ conidia/mL was added into 700 μL of acidic PD broth as control, SSG CFS, or $10^7$ colony forming units (cfu)/mL in PD broth. After being kept in the dark at 25° C. for 1, 4, 8, 24 and 48 h, treatments were examined and photographed for conidia lysis, germination, and differentiation under an Olympus IX71 inverted microscope at magnification of 100×. The assay was repeated once and each treatment included three replicate wells.

Microscopy of Effects of SSG on Survival of Microsclerotia from Leaf Tissue

Microsclerotia were extracted from infected boxwood leaves 8 weeks after inoculation as described in the literature. 30 μL of the suspension was added into 700 μL of PD broth as the control, SSG CFS, or $10^7$ cfu/mL in PD broth in a 2-mL tube. The tubes were kept at 25° C. in the dark and a 100 μL aliquot of the suspension was spread on acidic PDA at 1, 4, 8, 24, 48 h and 2 weeks after treatment and recorded for number of Cps colonies after 7 days at 25° C. in the dark. Microsclerotia survival at 1 h and 14 days after treatment was also examined and photographed under an Olympus IX71 inverted microscope at magnification of 40×. Each treatment included 3 replicate tubes.

Plant and Growth Conditions

*Buxus sempervirens* 'Justin Brouwers' in 1 gallon (7 inch) pots was used in the study. Plants were kept in the field plot at the Virginia Tech Hampton Roads Agricultural Research and Extension Center (HRAREC), watered, and fertilized regularly before the experiment. Since Cps is a high alert plant pathogen in the USA, plants were transferred at the time of experiments to the laboratory, watered regularly or as needed, and tested at 23° C. with a 9 h light/15 h dark cycle.

Plant Treatments with SSG

Treatments included SSG CFS, the suspension of the cell pellet in 200 mL 0.01% polysorbate 20, its dilutions, and the control, 0.01% polysorbate 20 or nutrient broth. A 10-fold serial dilution was made from the cell suspension with 0.01% polysorbate 20. The concentration of the suspension was determined using the suspensions of 7th and 8th dilutions that were plated onto PDA for cfu/mL. Treatments also included treatment time and intervals before and after the challenge of plants with Cps inoculum. Plant treatment before Cps inoculation included a lead time of 2, 10, 20, and 30 days while that after Cps inoculation included a post time of 3, 24, and 48 h.

At treatment, plants in each of three pots in a large plastic container (22×13×17.5 in) before or after Cps inoculation, were sprayed with 20 mL of the tester. Plants were kept in the containers with covers for 24 h after spray. All experiments were repeated at least once.

Plant Inoculation with Cps and Disease Assessment

Plants before and after treatment were inoculated with a Cps conidial suspension at $1\text{-}4\times10^4$ conidia/mL. Plants in each pot were sprayed with 20 to 50 mL inoculum depending on the Cps concentration used. Plants after inoculation were kept in the containers with covers for 48 h to promote plant infection and then without covers for additional 5 days for disease development. The number of infected leaves in each pot were counted to calculate disease incidence. The % efficacy of each treatment for control of boxwood blight was computed by dividing the difference in disease incidence between the control and the treatment by the control disease incidence.

Effects of SSG on Cps Sporulation from Leaf Litters

Six boxwood plant pots were placed into upside-down empty pots in the containers to prevent cross contamination during the experiment and plants were watered 24 h before treatment. Diseased leaf litters were harvested from diseased plants 3 weeks after inoculation with Cps conidia at $5\times10^4$/mL and stored at 4° C. for over 30 days after drying. Each container was sprinkled with about 100 leaves. Half of the pots were sprayed with 70 mL 50% culture (about $10^{7\text{-}8}$ cfu/mL) onto the litter under the plants, and another half of the ports were sprayed with the same amount of 50% of the same media used for the culture as control. The containers were watered overhead every other day until the end of the experiment to allow inoculation by splash to plants after covered with lids for 24 h after treatment. Ten of the treated leaves were sampled from each pot at 5, 10, 20, 30, 40, and 50 days post-treatment (dpt) and placed in a moist crisper for 4 days for Cps sporulation. To quantify sporulation, the leaves were suspended in 10 mL 0.01% polysorbate 20 by vortexing for 10 min and the suspension was loaded onto a hemocytometer for conidia count under a microscope. Each experiment containing 6 replicate pots was conducted three times.

Effects of SSG on Boxwood Protection from Cps Splash from Leaf Litter

At 50 dpt, the branches and leaves including fallen ones in the pots of the leaf litter treatments in two experiments were counted to determine leaf variation between the treatments and the ratio of leaves and branches. The latter was used to estimate the total leaves of each pot in all experiments. Branches and diseased leaves in all 6 pots of each treatment were counted in all experiments. Disease incidence of treatments was determined based on these counts and leaves per branch. The experiment was repeated twice.

Assessment of SSG Survival in the Soil after the Treatment

At 50 dpt of treatments of above experiments, a 100 mg soil sample was taken 3 cm depth under the surface of each treatment pot to determine SSG survival. Individual samples were suspended in 10 mL SDW by vortexing for 15 min. After this settled for 10 min, 100 μL of the suspension was spread onto a PDA plate. Colonies were counted after the plates were incubated at 25° C. for 48 h. Colonies for three plates were counted for each sample.

Taxonomy of SSG Isolates

DNA extracted from SSG cells was used for taxonomy by sequencing and restriction fragment length polymorphism (RFLP). For16S rRNA gene PCR and sequencing, universal primers 27F, 968F, and 1410R were used. For RecA gene PCR and sequencing, BCRI and 2 primers were used. Sequences were blasted against known sequences of microbes to match to a species level.

In addition to sequencing, SSG PCR products of RecA were subjected to HaeIII and Mn/I-based RFLP analysis to place SSG to a genomovar of *Burkholderia cepacia* complex (Bcc). DNA of SSG was also amplified with specific primers for *B. cepacia* epidemic strain marker (BCESM) to differentiate SSG from clinical strains of Bcc.

SSG was streaked on *Burkholderia cepacia* selective agar (BCSA, LabGenome, Houston, TX, USA) and incubated at 25, 35, and 42° C. for 72 h to confirm its membership in Bcc.

Statistics

Standard errors were calculated from standard deviation and number of replicates from each assay with Microsoft Excel. T-test at equal variances in Excel was used for evaluating statistical significance between treatments according to the least significant difference (LSD) at P=0.05.

Example 2: Results and Discussion for Assessment of Control of Boxwood Blight

SSG Inhibits Cps Growth, Conidium Morphogenesis, and Microsclerotium Germination SSG was selected among eight bacterial isolates from symptom-reversed leaf area of boxwood after inoculation with Cps because of its superior antagonism presented in the dual culture assay. Mycelial growth of plugs in the center of plates were not (or were, but only to some extent) suppressed by other isolates during the assay. In contrast, mycelial growth was suppressed by SSG from beginning of the assay and did not change through the end of the assay.

The time course study showed that both the cells and cell free supernatant (CFS) of SSG affected conidium morphogenesis. Conidia in the SSG cell suspension did not germinate at any time point, and more and more of them lysed with increasing exposure time. None were present at 24 h after the treatment.

Similarly, those in CFS had a significantly lower germination rate than the control (P<0.0001) indicating lysis of conidia. However, there were half empty conidia which were not apparent in the cell treatment. Furthermore, very few germlings of CFS treatment developed and formed hypha. In contrast, germination rate of control was high at the first hour and climbed with increase of incubation time and formed hypha and mycelia.

Both CFS and SSG also suppressed the survival of Cps microsclerotia from leaf litters. Isolated microsclerotia did not form colonies at 4 h after incubation in SSG cell suspension and in CFS for 8 h. In contrast, they formed colonies in control under the same conditions. In media broth, the control had massive mycelia growth at 2 weeks after the treatment while CFS and cells treatments grew nothing although those in CFS survived longer.

SSG Reduced Disease Incidence of Boxwood Blight

Figure 2:
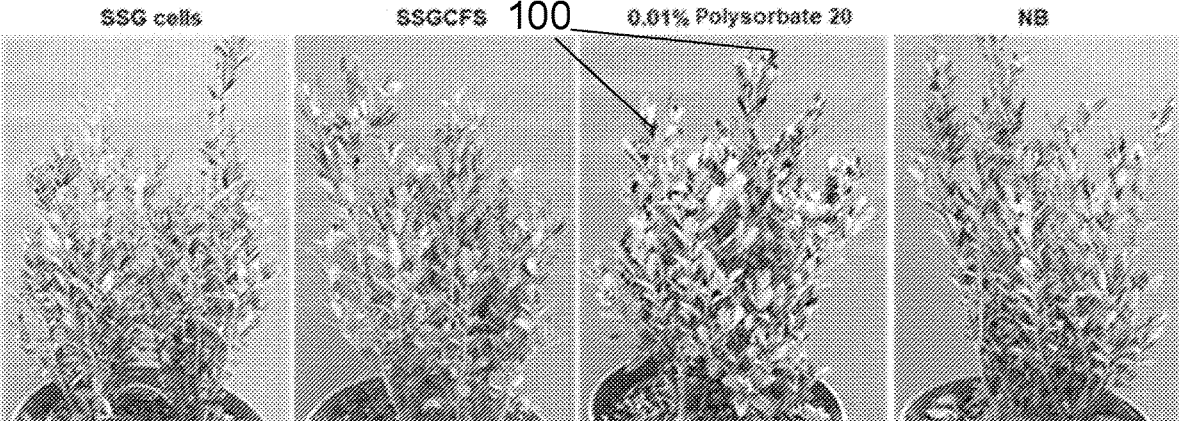
FIG. 2 shows protection of *Buxus sempervirens* 'Justin Brouwers' plants with SSG cells and cell-free supernatant (CFS) in comparison with controls (0.01% polysorbate 20 and nutrient broth) 7 days after inoculation with Cps conidia

With reference to FIG. 2, SSG also reduced disease incidence of boxwood blight. Compared to the controls, plants treated with cell suspension in 0.01% polysorbate 20 at >$10^8$ cfu/mL and CFS received 99.6% and 66.9% protection against blight 100, respectively, when inoculated with conidia. Protection by cell suspension decreased with decreasing number of cells. It reduced to 85.7% at $10^7$ cfu/mL, although protection was not significantly different from the higher concentration. There was significant reduction of protection when the cell concentrations were reduced between $10^{3-6}$ cfu/mL and plants received 35 to 40% protection. However, plants had little protection when cells were further diluted.

Lead time for treatment before the inoculation also affected the plant protection efficacy. Efficacy did not change significantly between lead time 2 days and 10 days. Efficacy was reduced when lead time was 20 days or longer. However, plants received more than 50% protection, indicating the persistence of antagonism of SSG.

Treatment after Cps inoculation was less effective compared to pretreatment. However, infection was suppressed if inoculated plants were treated early. Results varied compared to using cell suspension of CFS (Table 1). Infection was reduced by 99%, 81%, and 61% when inoculated plants were sprayed with SSG cells at >$10^8$ cfu/ml at 3, 24, and 48 h after inoculation. There was decrease of efficacy with progression of infection. However, when CFS was used, 99.2% of plants were protected from infection at 48 h after inoculation.

TABLE 1

Effect of Post-Treatment Time with SSG after Inoculation with
*Calonectria pseudonaviculata* (Cps) on Disease Incidence

| Time Post Inoculation (h) | CK1 | Cells[x] | Reduction | CK2 | CFS[y] | Reduction |
|---|---|---|---|---|---|---|
| 3 | 65.1 ± 7.3[z] | 0.7 ± 0.2 | 99.0 | NA | NA | NA |
| 24 | NA | 12.3 ± 1.2 | 81.2 | NA | NA | NA |
| 48 | NA | 25.2 ± 2.8 | 61.3 | 59.9 ± 7.1 | 0.5 ± 7.1 | 99.2 |

[x]Cell suspension at >$10^8$ cfu/mL controlled by 0.01% polysorbate 20. Disease incidence reduction was calculated compared to the control at 3 h post inoculation.
[y]Cell-free supernatant from 40 h cell culture and controlled by the nutrient broth medium. Disease incidence reduction was calculated compared to the control at 48 h post inoculation.
[z]Average of disease incidence (%) by Cps inoculation at 48 h post inoculation with Cps at 1-5 × $10^4$ conidia/mL from 6 replicate pots of plants from two independent experiments. Numbers after ± indicate standard error.
NA = Not Available SSG Reduced Cps Sporulation and Protected Plants from Leaf Litters Cps sporulation on leaf litters after sprayed with SSG culture was significantly reduced compared to the control. The reduction, about 40,000 conidia/cm² was consistent at each sampling time despite of nature reduction. Conidium production of SSG treatment was almost controlled at 30 or longer exposure. While many conidia were observed for the control, there were very few conidia at the last sampling time (50 dpt). Meanwhile, SSG colonies were recovered from the sample soil indicating survival of SSG in soil. The density of cells in the soil was about 18,500 (±42) cfu/g.

Figures 3A, 3B, 3C:
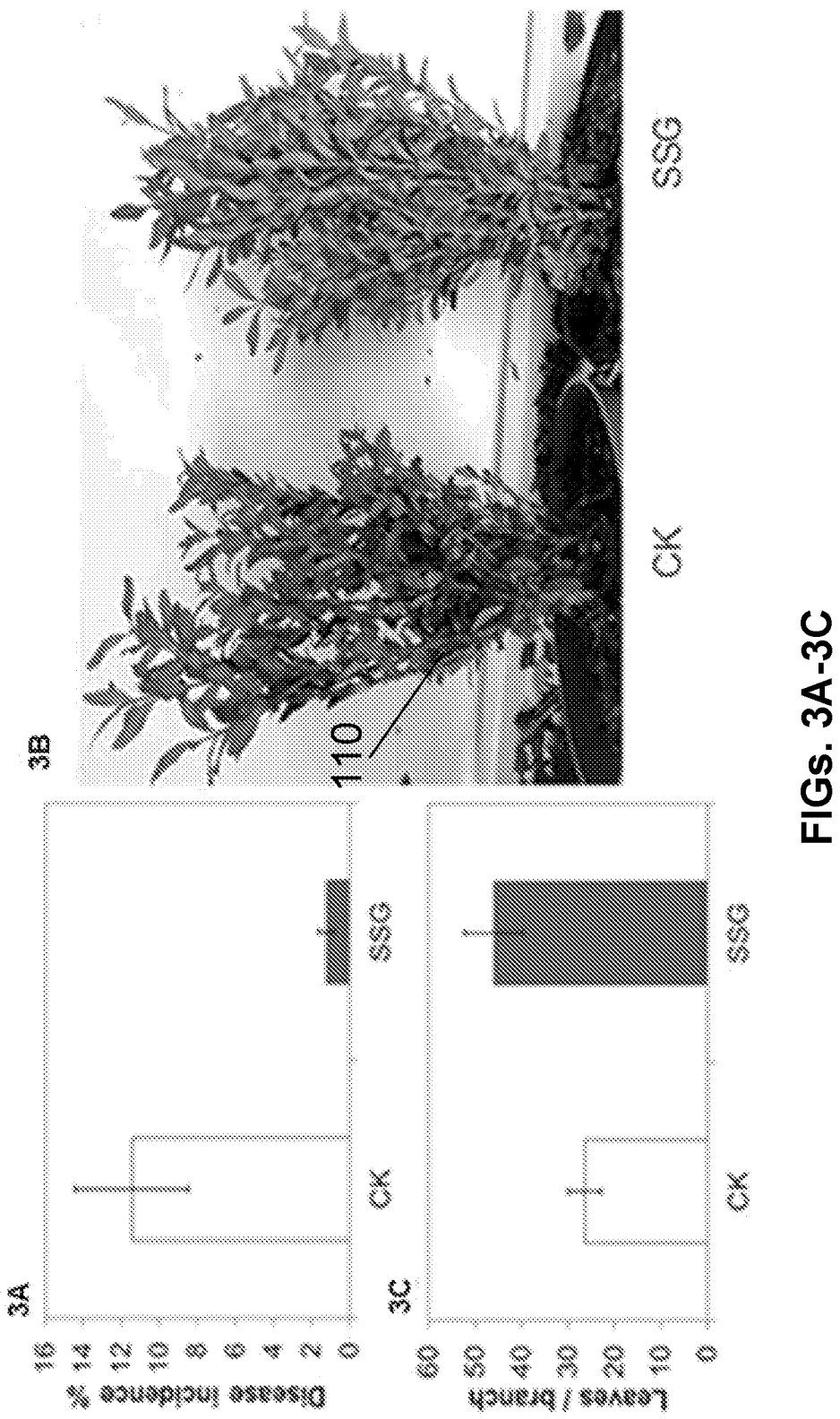
FIGS. 3A-3C show the effect of SSG on plant protection against Cps from leaf debris.

SSG also affected plant infection through leaflitters and plant growth. Plants in the pots with treated leaf litters by SSG culture had significantly lower disease incidence (1.2%) than the control (11.4%) 50 dpt after the treatment (FIG. 3A). With reference to FIG. 3B, disease 110 occurred mainly on the bottom of the leaves, indicating that the inoculum originated from the litters. Furthermore, SSG pots had significantly more leaves compared to the control pots, indicating plant growth during the treatment.

Identification of SSG

DNA of SSG was sequenced for 16S rRNA gene. The sequence of SSG matched at 99% identity with many of those know species in the *Burkholderia cepacia* complex (Bcc). To confirm that SSG was a member of Bcc, SSG was grown on Bcc selective media (BCSA) at 25, 37, and 42° C. Sage colonies appeared in the plates at 25 and 37° C. and the media color turned to yellow after 48 h, indicating SSG as a typical Bcc bacteria. To further classify SSG, DNA of SSG was amplified for RecA gene and digested with HeaIII and MnII restriction enzymes. However, RFLPs showed inconsistent patterns between genomovars I and III. The sequence of the RecA gene of SSG placed SSG in different subtrees despite that it matched several known species in Bcc and had the best match to *B. cepacia* strains. SSG was negative for *B. cepacia* epidemic strain marker (BCESM) when the DNA was further analyzed. These results indicated that taxonomy of SSG in Bcc was not clear but differed from clinical strains.

DISCUSSION

This study identified SSG as a potential biofungicide of boxwood blight from boxwood endophyte isolates. SSG provided strong protection against boxwood blight when the cells at higher than one million cfu/mL and cell free supernatant (CFS) of cultures were used to pretreat the plant 10 days before inoculation of the pathogen Cps. The efficacy is superlative compared to those previously reported non-indigenous fungal *Trichoderma koningiopsis* and bacterial *Pseudomonas protegens*, and its control efficacy is comparable to that of currently used fungicides. SSG is also very effective in controlling infection at the early stage after the inoculation. Symptoms from Cps infection on susceptible English Boxwood can appear as early as two days after inoculation following penetration and colonization on at 5 and 12 h. 99% of plants were prevented from symptom production when treated with SSG cells at >$10^8$ cfu/mL 3 h after inoculation and CFS of SSG 48 h after inoculation with Cps, suggesting that SSG may be used to terminate the infection process and stop the penetration of the pathogen. Furthermore, SSG gradually degraded Cps in leaf debris. Since SSG can survive in the soil at least 50 days as indicated by sampling at the end of the experiment, it may be used as a sustainable biosanitizer for pathogen inocula in/on the soil and diseased leaf litters. Plant disease biocontrol plays an important role in Integrated Pest Management (IPM) systems in reducing dependence on chemical inputs.

With a high efficacy in boxwood blight control and plant protection, SSG as one of few plant Burkholderial endophytes reported, has great potential to fulfill the task and beyond.

Boxwood protection by SSG may be derived from direct and indirect antagonisms involving complex modes of action. Direct antagonisms is demonstrated by conidium lysis and no germination of microsclerotia in SSG cells. The bacterial metabolites greatly contributed to the killing and suppression. First, diffusion of SSG suppressed mycelium growth of Cps. Second, conidia had poor survival and germination and abnormal differentiation, and microsclerotia decreased survival after incubation with CFS. Similarly, CFS suppressed early plant infection and reduces disease incidence. However, SSG volatiles are unlikely involved because no suppression was observed when dual cultures of SSG and Cps were placed in the divided plates. Direct antagonism of SSG may be attributed to production of antibiotics commonly found in Bcc species such as pyrrolnitrin, occidiofungins, and cepafungins (glidobactins).

Bcc species produce pyrrolnitrin optimally late in the growth phase and accumulated a main portion in their cells. The fact that CFS rescued plants from infection by Cps at 48 h after inoculation while SSG cells only did for the infection at 3 h but not later also support involvement of antibiotics appears linked to presence and amount of pyrrolnitrin. However, whether and how these antibiotics and if there novel antibiotics or metabolites involve direct antagonisms of SSG to Cps remained to be further investigated. In addition to metabolites, SSG cells may also contributed the direct antagonism of SSG. In the in vitro experiments, conidia lysed in the SSG cell suspension were significantly more than those in CFS, suggesting that SSG cells may out-compete or kill Cps during germination and penetration. Further investigation of direct interaction between bacterial cells and Cps using lockout of antibiotic gene SSG or drugs blocking the release of antibiotics is warranted to confirm this mode of action of SSG.

Indirect antagonism by SSG is shown by the presence of constant medium levels of protection from treatments at extended lead time longer than two days and cell concentrations at 1,000 cfu/mL or higher. Bcc bacteria contain complex QS systems for the regulation of the production of a variety of extracellular products including siderophores and antibiotics and for plant colonization and growth. Although it is not clear how SSG interacts with plant, same level of protection resulted from different concentrations or survival status of cells does not look like a consequence of antibiotics alone but more like a consequence of plant defense elicited by threshold signals of SSG at treatment. Another implication of the involvement of indirect antagonism is from the fact that SSG was one of the endophytes from the leaf area of symptom reversion after Cps inoculation. However, it is not clear what role SSG played in the healing process. Bacterial endophytes including *Burkholderia* have many traits contributing to indirect antagonisms. They produce growth regulators and other chemicals to promote plant defense and growth. *Burkholderia* produce siderophores, giving a competitive advantage at scavenging for iron. They also produce 1-aminocyclopropane-1-carboxylate (ACC) deaminase, fix nitrogen, and solubilize phosphate for plant growth promotion.

SSG as a highly effective *Burkholderia* antagonistic endophyte for Cps and possesses great potential in controlling boxwood blight. However, like other bacterial biocontrol agents and fungicides, SSG does not work at its best for more than 10 days for pretreatment. This may be due to decrease of survival of SSG on plant surface or limited entry into plant tissue as suggested by reduction of efficacy with increased treatment lead time.

*Burkholderia* has been recovered from various environments. In this study, SSG was isolated from plant tissue and survived in soil for at least 50 days. It is likely that light and moisture conditions may be the major factors associating SSG survival on leaf surface and in soil and plant tissue. Another issue that may be encountered in the application of SSG is its safety. SSG belongs to Bcc and is very similar to *B. cepacia* in sequence in genomovar I although it is phylogenetically different from any of the known strains in the genomovar that are dominant with environmental strains. More importantly, SSG was originated from a plant and is negative for the human virulent BCESM marker, confirming its difference from clinical strains associated with cystic fibrosis patients.

Example 3: Materials and Methods for Effects of SSG on Other Plant Pathogens/Diseases Plant Pathogen Cultures and Growth Conditions Plant bacterial, fungal, and oomycete pathogens including *Fusarium solani* (11B07), *Volutella buxi, Phytophthora capsici* (22H3), P. cinnamormi (30D6), *P. infestans* (27E7), *P. nicotianae* (1B11), *P. ramorum* (32G2), *P. sojae* (28G4), *E. coli* (DH52) (60622), *Erwinia carotovora* (60627), Psuedomonas *syringae* (60625), *Ralstonia solanacearum* (60622), *Stenotrophomonas maltophilia* (PE1-sy), and *Xanthomonas* campastris (60627) were used in this study. Strain/isolate cultures of fungi, *Phytophthora*, and bacteria were plated out from long term storage and grown on PDA, V8 agar, and nutrient agar plates, respectively at 25° C. before tests were performed.

Dual Cultural Assays

Streak and disk methods described in the manuscript were used for tests of culture growth of bacterial and fungal/*Phytophthora* pathogens, respectively in this study. Each test included three replicate plates and was repeated at least once.

Similar methods used for conidia of Cps described in Example 1 were used for investigating the effects of SSG on the survival and germination of zoospores. Zoospore were produced using a plug and wet plate method described previously. Specifically, 100 μL zoospore suspension at $10^5$/mL was added into 2 mL PDB (CK), CFS from 40 h-culture in PDB, or suspension of SSG cells in PDB and incubated at 23° C. Zoospore behavior was observed under a microscope after 24 h.

Plants and Growth Conditions

Test plants include annual *vinca* (*Catharanthus* 'Little White'), cucumber (*Cucumis sativus*), pepper (*Capsicum*), rhododendron (*Rhododendron catawbiense* 'Boursault'), and tomato (*Solanum lycopersicum*). Plants except for *rhododendron* were 1-gallon plant gifts from Sunder's Brothers and were seeded in a greenhouse under mist. Seedlings with four leaves were transferred into 4-inch pots and grown in the greenhouse for an additional 4-8 weeks. Plants were fertilized once with slow-release fertilizer and watered 2-3 times each week before use.

Plant Protection Against Diseases

Five phytopathosystems with plants and *Phytophthora* spp described above were investigated. Both treatment and inoculation were conducted in the large containers described in Example 1 in the laboratory. Plants were pretreated 48 h with the diluted cell culture or resuspended and diluted cell culture with 0.01% polysorbate 20 before inoculation. Controls were the same solution (nutrient broth, or 0.01% polysorbate 20) without the bacterial culture. Plants were kept in the containers with lids to keep moisture for 24 h after treatment with 30 mL for plants in the 4 inch pots and 50 mL for plants in the 1-gallon pots at $10^{7-8}$ cfu/mL. Inoculation with zoospores was conducted after the lids had been removed for 24 h. Inoculum concentrations ranged from $1.3 \times 10^3$/mL to $2 \times 10^4$/mL, and 25 mL or 75 mL was sprayed on plants in each 4 inch and 1-gallon pot, respectively. Inoculated plants were kept in containers with lids for 24 h and without lids for 1 week for infection development. Total leaves, infected leaves, or lesion number on leaves was recorded to determine the disease incidence. Each treatment in the experiment for a phytopathosystem included three replicate plant pots. Experiments were repeated twice for annual *vinca, P. nicotianae*, and *rhododendron* with *P. ramorum*, once for pepper or cucumber with *P. capsici*, and none for tomato with *P. infestans*.

Example 4: Results and Discussion for Effects of SSG on Other Plant Pathogens/Diseases Effects of SSG on Culture Growth of Varieties of Plant Pathogens SSG was tested for suppression of cell and mycelium growth on isolates/strains of 14 bacteria, fungal and *Phytophthora* species. In the 6 bacterial strains tested, significant inhibition was observed on four, including Psuedomonas *syringae, Stenotrophomonas maltophilia, Xanthomonas campestris*, and *E. coli*. Among them, *Xanthomonas* campastris was most vulnerable, with a suppression zone nearly 3 cm in diameter. However, there was no suppression on *Erwinia carotovora*, and suppression on *Ralstonia solanacearum* was not significant, suggesting the antagonistic spectrum of SSG on bacteria is limited.

SSG inhibited the growth of all test fungi and *Phytophthora*. Among *Phytophthora*, the growth of P. irifestans, *P. ramorum*, and *P. sojae* were totally suppressed, although *P. capsici, P. cinnamomi*, and *P. nicotianae* were not. This difference may result from growth speed of the species on V8 agar. The former three species grew slow so that they may be caught up by diffusion of SSG strips while the latter three grew fast, and the first grown mycelia were not affected.

Suppression on *Phytophthora* by metabolites from SSG was also shown with zoospores. Zoospores in PDB germinated and developed mycelia after 24 h incubation. In contrast, most zoospores in CFS disappeared or lysed. However, those in SSG cell suspension in PDB appeared less affected. One third of them also germinated, although the germlings were weak and the hyphal development was poor. This suggests that SSG metabolites are responsible for zoospore degradation and germination suppression and are effective at a certain concentration that the cells did not achieve because of resuspension.

Effects of SSG on *Phytophthora* Diseases

Figures 6A, 6B, 6C, 6D:
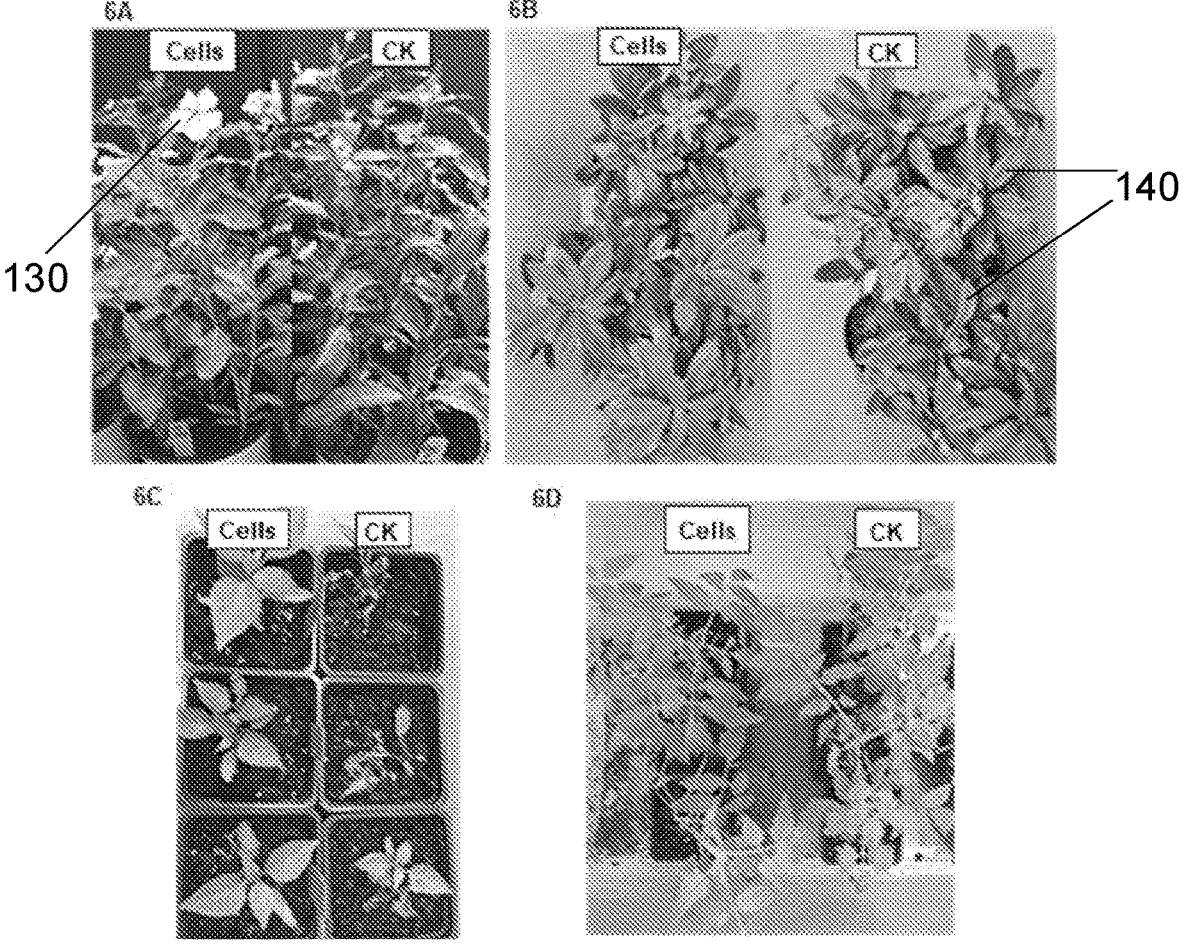
FIGS. 6A-6D show plant protection against *Phytophthora* species by SSG.

Plants of annual *vinca*, cucumber, pepper, *rhododendron*, and tomatoes were tested against *P. nicotianae, P. capsici, P. ramorum*, and *P. infestans*, respectively, after being treated with SSG (see FIGS. 6A-6D). With reference to FIG. 6A, annual *vinca* received excellent protection against *P. nicotianae* as evidenced by increased number of/larger flowers 130. Shoot and leaf infection was reduced by 98% and 96%, respectively when cell culture of SSG was used. The reduction was 97 and 91%, respectively, with the resuspended cells and 85% and 71% with CFS. These results indicate that using cells or CFS alone reduced disease severity and using both cells and metabolites of SSG gave the best protection of plants. The latter may involve direct and indirect antagonism.

Efficacy of plant protection against the pathogen by SSG was also significant in *rhododendron-P. ramorum* system. With reference to FIG. 6B, resuspended SSG cells allowed 60% reduction of leaf infection 140 and 80% reduction of lesions. Efficacy of SSG decreased with extended treatment lead time. However, reduction rates of pretreatments of 1 and 2 weeks were same (40%), indicating the presence of induced resistance. It is not clear whether the efficacy may improve with SSG culture.

Plant protection in cucumber/pepper-*P. capsici* by SSG was not as good as in the above phytopathosystems although SSG culture was not also used in those experiments. Between CFS and suspended cells, better results were obtained with the latter. They reduced plant infection of pepper and cucumber by 55% and 33%, respectively, compared with CFS that reduced the infection by 27% and 17%. No protection was shown for tomato against *P. infestans*. The lower efficacy of SSG on these systems likely results from the susceptibility of test plants to SSG. Various levels of plant toxicity was observed on the test plants treated with CFS and cells alone which appeared associated with the tenderness and hairy status of plant. The more tender the plants, the less protection. The hairy cucumber and tomato plants had little protection.

Example 5: Materials and Methods for Potent *Burkholderia* Endophyte Against Boxwood Blight Caused by *Calonectria pseudonaviculata*

Cps Isolate and Conidia Production

Cps isolate Sb1 (12A01) was used in this study. This isolate, although recovered from affected sweet box (*Sarcococca hookeriana* var. *humilis*), was part of the same clone introduced to a private garden via infected English boxwood and has the same virulence as those from boxwood on the same garden as shown in a comparative study. Cultures were grown and maintained at 25° C. on Difco™ potato dextrose agar (PDA, Becton, Dickinson and Company, Sparks, MD, USA). Conidia were produced using fresh potato dextrose broth (PDB). Briefly, a small amount of mycelia was scraped from the culture surface then evenly distributed in 90 mm plates with fresh PDB. After a 4 day incubation at 25° C., the nutrient medium was decanted. Mycelial mats that formed and were attached to the plate bottom were rinsed with sterilized distilled water (SDW). These washed plates were then placed under fluorescent light at 1200 lux to induce the production of conidia. Conidia were harvested with SDW or 0.01% polysorbate 20 (Croda Inc., New York, NY, USA) into a beaker; spore concentration was determined with a hemocytometer.

Plant Growth Conditions and Biosafety Measures for all in-Planta Inoculation Studies

*Buxus sempervirens* 'Justin Brouwers' boxwood was used in all inoculation studies. Blight-free liners were donated by Saunders Brothers Inc. (Piney River, VA, USA). Two liners were potted in a 15 cm plastic pot with pine bark-based potting mix and fertilized once with slow-release fertilizer (Harrell's LLC, Lakeland, FL, USA). Plants were irrigated up to three times a day, depending upon the time of year, and maintained on a gravel pad until use at the Virginia Tech Hampton Roads Agricultural Research and Extension Center in Virginia Beach, VA, USA.

To prevent Cps from spreading to nearby boxwood plantings, all inoculation studies were done in a laboratory with restricted access. During each experiment, plants were placed in Ultra™ Latching Storage Boxes (66 cm×41 cm×50 cm, Sterilite Corporation, Townsend, MA, USA) to further contain the diseased plant materials. At the termination of experiments, all used plants and planting materials were autoclaved before disposal, while used boxes and other tools are washed and decontaminated with 70% ethanol.

Isolation and Selection of the Bacterial Endophyte from Boxwood Leaves with Unusual Response to Cps Inoculation Detached leaves of Justin Brouwers boxwood were washed in tap water then surface sterilized with 70% ethanol and inoculated with a drop of Cps conidia. Water-soaked lesions developed on individual leaves within 2 days. With reference to FIG. 4, however, not all of these lesions 120 progressed further; instead, some disappeared at 7 days post-inoculation.

Figure 14:
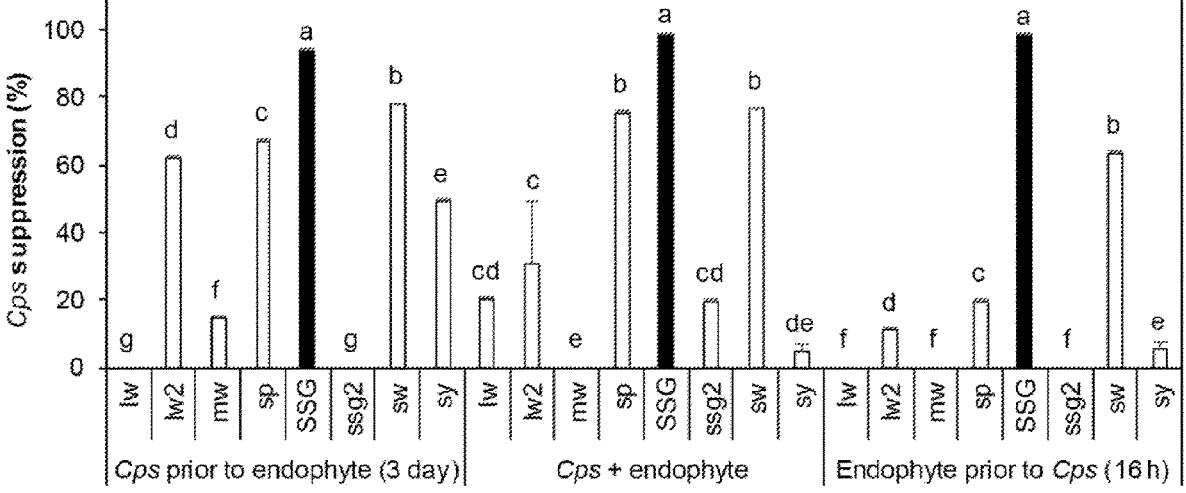
FIG. 14 shows reduction in colony diameter of 4 week old *Calonectria pseudonaviculata* (Cps) by SSG and other boxwood endophytes coded by size (s=small, m=medium, l=large) and color (p=pink, sg=sage green, w=white, y=yellow), plus a number if more than one isolate of similar color types and sizes assessed in three dual culture assays with slightly different Cps seeding timings in relation to bacterial streaking: 3 days before (left), at the same time (middle), and 16 h later (right). Each column represents a mean of triplicate plates, topped with a standard error bar. Columns topped with the same letter within each assay did not differ according to the LSD test at p=0.05.

The leaves showing symptom reversion were surface sterilized again with 70% ethanol, cut into small pieces, then vortexed in SDW for 10 min. When the leaf debris settled to the bottom, 100 μL of the supernatant was plated onto PDA then incubated at 25° C. for 48 h. Resultant bacterial colonies were grouped by color and size; eight representative colonies were subcultured on Difco nutrient agar (NA, Becton, Dickinson and Company, Sparks, MD, USA) for initial evaluation using a dual culture assay. Briefly, a mycelial plug of Cps was placed in the center of 90 mm PDA plates and a bacterial isolate from a 24 h liquid culture in Difco nutrient broth (NB, Becton, Dickinson and Company, Sparks, MD, USA) was streaked equidistantly on its left and right sides. Control plates were streaked with NB without the small sage green (SSG). The assay was done three times with slightly different timings of Cps seeding in relation to bacterial streaking: 3 days before in the first run, at the same time in the second run, and 16 h later in the third run. Each run included three replicate plates per bacterial isolate. All plates were incubated at 25° C. in the dark. The diameter of the Cps colony in each plate was measured 4 weeks later. The bacterial isolate that produced small sage green (SSG) colonies on PDA was consistently most effective against Cps growth (FIG. 14); subsequently, it was selected for further evaluation.

SSG Cell Suspension and Cell-Free Supernatant Preparation

SSG was maintained on PDA plates. For liquid culture, a 4 mL NB was inoculated with a single colony and incubated on a G24 Environmental Incubator Shaker (New Brunswick Scientific Inc., Edison, NJ, USA) at 180 rpm and 28° C. overnight, then used as a culture stock. For experiments, 150 mL NB or PDB was inoculated with 1 mL of the SSG stock then incubated for 40 h under the same conditions. The culture was centrifuged at 14,210×g for 15 min. Bacterial cells in pellets were resuspended in 200 mL PDB for in vitro assays or 0.01% polysorbate 20 for plant inoculation studies. Bacterial cell concentration of resultant resuspensions was determined by spreading 100 μL of its dilutions on PDA then counting the emerging colonies after a 2 day incubation at 25° C. The resultant bacterial cell concentrations ranged from $10^8$ to $10^9$ colony-forming units (cfu) per milliliter. In the meanwhile, the supernatant was further passed through a 0.22 μm filter to produce cell-free supernatant (CFS). Resuspended bacterial cells and CFS were evaluated separately for their potential against Cps unless stated otherwise. The resuspended bacterial cells and CFS treatments hereafter were referred to as Cell and CFS, respectively.

SSG Effect on Cps Conidia Survival and Germination

Three treatments, cell at $10^7$ cfu/mL, CFS, and PDB only as a control, were included in this study. A 100 μL aliquot of Cps suspension at $10^4$ conidia/mL SDW was mixed with 700 μL of Cell, CFS, or PDB in Costar™ 24 well Flat Bottom Cell Culture Plates (Corning Inc., Corning, NY, USA). The mixtures were incubated at 25° C. in the dark for 1, 4, 8, 24, or 48 h then examined for conidia lysis, germination, and germling differentiation using an Olympus IX71 inverted microscope (Olympus Corporation of the Americas Headquarters, Center Valley, PA, USA) at magnification of 100×. This assay included triplicate wells per treatment and was done twice.

Effect of SSG on Boxwood Blight

Four treatments were included in this study: (1) Cell at $10^8$ cfu/mL 0.01% polysorbate 20, (2) CFS, (3) 0.01% polysorbate 20 (as the control for the Cell treatment), and (4) NB (as the control for CFS). Boxwood foliage was pretreated at 20 mL/plant using hand sprayers one day prior to being challenged with Cps. This experiment had triplicate plants per treatment and was done three times. Treated plants were arranged in a randomized complete block design in the storage boxes for inoculation with Cps at 1 to $5\times10^4$ conidia/mL 0.01% polysorbate 20 at 20 mL/pot. Inoculated plants were kept in closed storage boxes for 48 h to facilitate infection. Diseased leaves and healthy-looking leaves on each plant were counted 7 days post inoculation. Disease incidence was calculated by dividing the diseased leaf count by the total leaf count.

Effect of SSG Concentration on Boxwood Blight

Five concentrations of 0, $10^3$, $10^5$, $10^7$ and $10^9$ cfu/mL 0.01% polysorbate 20 were included in the initial run. Based on the results from the initial run, the concentration of $10^3$ cfu/mL was excluded from the second run. Plant pretreatment including the lead time of one day, Cps inoculation, and disease assessment all were performed as described above with two minor changes. Cps inoculum concentration was at $5\times10^4$ and $2\times10^4$ conidia/mL in the initial and repeated runs, respectively. Likewise, the highest SSG cell concentration was slightly greater in the first than the second runs ($3\times10^9$ vs. $2\times10^9$ cfu/mL).

Effect of SSG Treatment Lead Time on Boxwood Blight

All boxwood plants were treated with SSG at $4\times10^8$ cfu/mL or 0.01% polysorbate 20 as control. A quarter of the plants pretreated with SSG and those with polysorbate 20 were inoculated with Cps at $2\times10^4$ conidia/mL 1, 10, 20, and 30 days later. SSG pretreatment, Cps inoculation, and disease assessment were all performed as described above for the SSG concentration experiment. Blight control was calculated for each lead time by dividing the difference in disease incidence between SSG treated and control plants by that of the control plants. This experiment was repeated once with SSG at $2\times10^9$ cells/mL and Cps at $10^4$ conidia/mL.

Effect of Post-Inoculation SSG Treatment on Boxwood Blight

This study included the application of resuspended SSG cells at three-time points: 3, 24, and 48 h post inoculation, plus a nontreated control. Cps inoculation, SSG treatment, disease assessment, and blight control calculations were done as described above for the lead-time experiment. The experiment was conducted twice with SSG at $5\times10^8$ cfu/mL and $4\times10^8$ cfu/mL while Cps was at $5\times10^4$ conidia/mL and $2\times10^4$ conidia/mL in the first and second runs, respectively.

SSG Effect on Potential of Diseased Leaves as a Source of Inoculum

This study began with collecting and air-drying diseased leaves then storing them in a cold room at 4° C. for 15 months. One hundred stored leaves were spread on the surface of the potting mix under healthy Justin Brouwers plants in a container, then immediately cover sprayed (not onto the boxwood foliage) with a mixture of 35 mL NB culture of SSG and 35 mL SDW at a final concentration of $10^8$ cfu/mL or 1 strength NB without SSG. Each treatment included three replicate plant containers and treatments were arranged in a randomized complete block design. After 24 h, plants in treated containers were overhead watered using a watering can, which was repeated every other day until the end of the experiment. To prevent cross contamination between treatments through movement of accumulated water at the bottom of boxes, plant containers were placed on inverted empty containers. Three sets of data were collected with Cps sporulation on leaf litter and blight incidence on boxwood foliage assessed six times while SSG survival in the potting mix was determined twice post-treatment. This experiment was conducted twice.

Cps ability to sporulate on control and SSG-treated leaf litter was assessed at 5, 10, 20, 30, 40, and 50 days post-treatment. On each assessment day, ten leaves were collected from each pot and placed onto mesh overlaid moist paper towels in closed plastic crispers for 5 days. These leaves were placed in a test tube with 10 mL 0.01% polysorbate 20 then vortexed for 10 min to dislodge conidia. Concentrations of conidia in resultant suspension were determined with a hemocytometer, and six independent counts were averaged for each replicate sample. The per ml conidia concentration was equivalent to the number of conidia produced per leaf. This number was then divided by Justin Brouwers average leaf size of 2 $cm^2$ to calculate the number of conidia produced per unit leaf area.

Blighted leaves including those fallen ones were counted for each plant. The total number of leaves on each plant was estimated by counting the number of branches then multiplying by a factor of 26 leaves per branch, which was predetermined based on the branch and leaf counts for plants in randomly selected 24 pots. Disease incidence was determined by dividing the diseased leaf count by total leaf estimate.

To determine SSG survival in soilless potting mix, a 100 mg sample was taken from the top 2 cm in each container using a straw. Each potting mix sample was added to a test tube with 10 mL SDW then vortexed for 15 min. After diluting 10 to $10^6$ times, 100 µL of original prep or a dilution was spread onto a PDA plate after the debris settled. Small sage green colonies were counted after a 72 h incubation at 25° C. Their SSG identity was verified with *Burkholderia cepacia* selective agar (BCSA, LabGenome, Houston, TX, USA).

SSG Species Identity and Differentiation from Epidemic Strains of *Burkholderia cepacia*

Three major steps were taken to determine SSG species identity. First, SSG was streaked onto BCSA medium and incubated at 25, 35, and 42° C. for 72 h to determine whether it belongs to the Bcc. Second, DNA was extracted from SSG cells, then 16S rRNA and RecA genes were amplified by PCR using the universal primers 27F, 968F, and 1410R, and primers BCR1 and 2, respectively. PCR products were sequenced at Eton Bioscience (Research Triangle Park, Raleigh, NC, USA). Processed sequences were deposited into GenBank (Accession: MK424809 for RecA gene and MK418913 for 16S DNA) and blasted against existing sequences in the NCBI repository and at EzBioCloud to determine the identity of this bacterial endophyte. Third, RecA PCR products were digested with HaeIII and MnlI then their RFLP were analyzed as described previously to determine their genomovar association in the Bcc.

Two additional steps were taken to assess SSG risk as a human health hazard. First, bacterial DNA was amplified with specific primers for the Bcc epidemic strain marker (BCESM) to determine whether this endophyte is associated with any known opportunistic human pathogens in the complex. Second, an onion maceration assay was conducted to differentiate SSG from clinical strains that generally do not macerate onion bulb scale tissue. Briefly, pieces of fresh onion scales were wounded with a sterilized needle and inoculated with 10 µL of 40 h SSG culture at $10^8$ cells/mL or NB as the control. The inoculated onion scales were incubated at 25° C. in a moist container, and symptom development of onion scale tissue was recorded after 3 days.

Data Analysis

Data from different experimental runs, if homogenous, were pooled then subjected to analysis of variance (ANOVA) to determine the level of difference among treatments and that of interactions among factors using Statistical Analysis Software version 9.4 (SAS Institute, Cary, NC, USA). Otherwise, they were analyzed by an experimental run. Treatment means were separated according to the least significant difference (LSD) test at p=0.05.

Example 6: Results and Discussion for Potent *Burkholderia* Endophyte Against Boxwood Blight Caused by *Calonectria pseudonaviculata*

SSG Effect on Cps Conidia Survival and Germination

Figure 8:
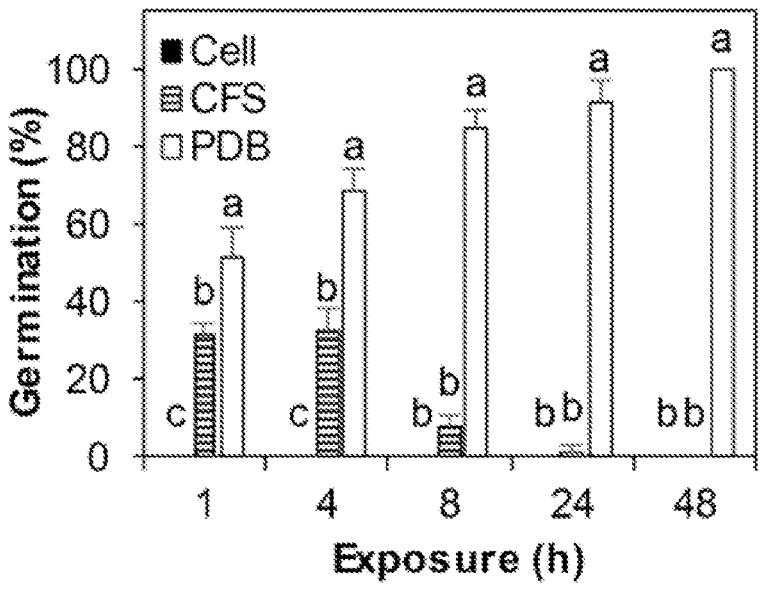
FIG. 8 shows conidia germination of *Calonectria pseudonaviculata* after being incubated in small sage green (SSG) cell suspension at $10^7$ cfu/mL (Cell), cell-free supernatant (CFS), or potato dextrose broth (PDB). Each column is an average of six replicates from two repeated assays and is topped by a standard error bar. Columns marked with the same letter within each exposure time did not differ according to the least significant difference (LSD) test at p=0.05.
Figure 9:
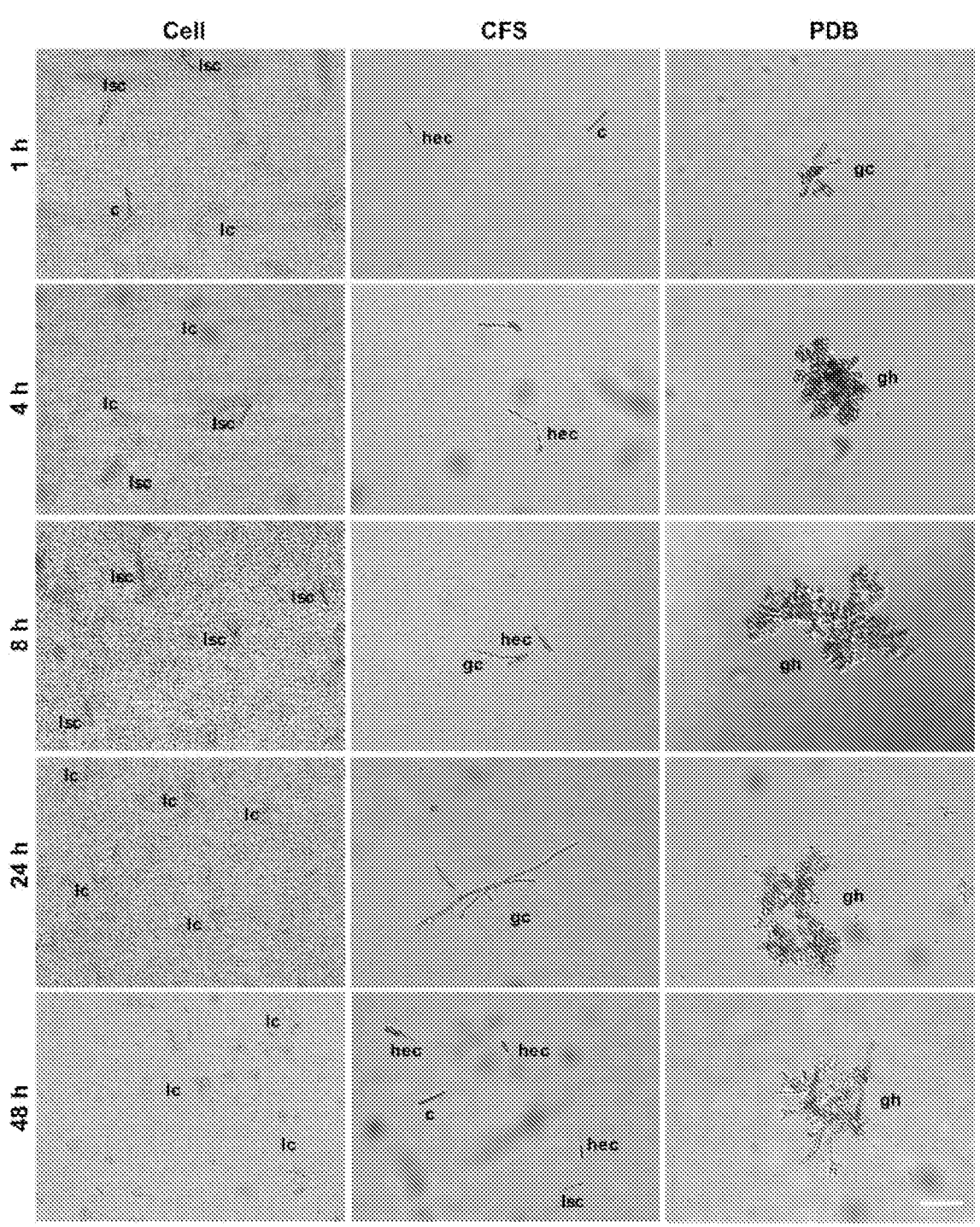
FIG. 9 shows micrographs of conidia morphology of *Calonectria pseudonaviculata* after being incubated in SSG cell suspension at $10^7$ cfu/mL (Cell), cell-free supernatant (CFS), or potato dextrose broth (PDB): c=conidium, lsc=lysing conidium, lc=lysed conidium, hec=half empty conidium, gc=germinating conidium, gh=growing hyphae from conidial germling. Bar=50 μm.

Difference was observed in germination of conidia among Cell, CFS, and PDB treatments (p<0.01), but not between the two experimental runs (p=0.19) nor among the exposure times (p=0.23). There were, however, significant interactions between treatment and exposure time (p<0.01). About 52% of conidia in control wells with PDB germinated within 1 h; their germination rate increased with time, reaching 100% at 48 h (FIG. 8) with germling aggregation and further development into hyphae (FIG. 9). In contrast, conidia germinated at a much lower rate in wells with CFS than those in control wells. None of the conidia in wells with SSG cells germinated over the 48-h period; in fact, they were all lysed. Similar conidial lysis was observed in wells with CFS, but to a lesser extent. Conidia that had not been lysed had an empty cell, they germinated poorly, and fewer germlings developed further (FIG. 9).

Effect of SSG on Boxwood Blight

Substantial blight control was seen on 'Justin Brouwers' plants pretreated with resuspended SSG cells or CFS one day prior to inoculation with Cps. Resuspended SSG cells were consistently more effective than CFS for blight control in all experiments (p<0.01). The former reduced blight incidence by nearly 100% when compared to the control with 0.01% polysorbate 20. Comparatively, CFS reduced blight incidence by 73% when compared to the control with NB. No difference in blight control among three experimental runs (p=0.31) nor any interaction between experiment run and treatment (p=0.35) was observed.

Effect of SSG Concentration on Boxwood Blight

Greater blight severity was observed (p<0.01) on control plants in initial than repeated experiments (98% vs. 33% leaves blighted) due to the difference in Cps inoculum concentration between the two runs ($5 \times 10^4$ vs. $2 \times 10^4$ conidia/mL).

Figure 10:
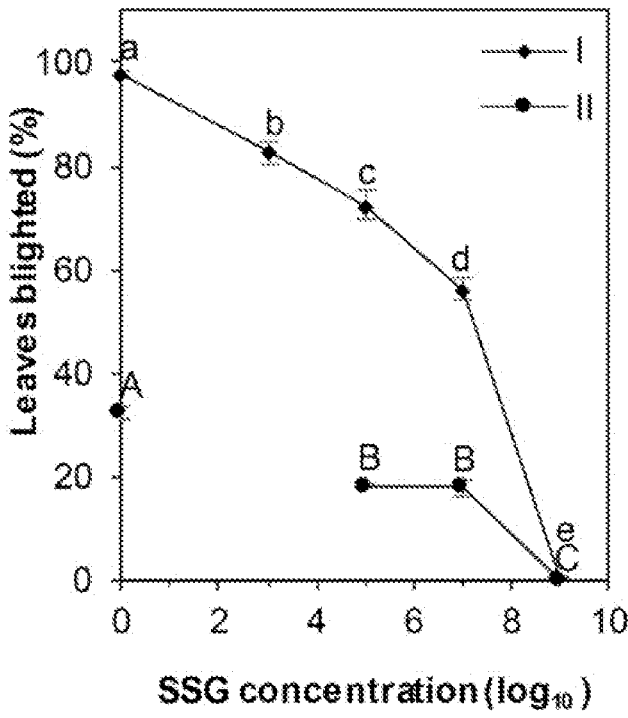
FIG. 10 shows leaf blight incidence on *Buxus sempervirens* 'Justin Brouwers' boxwood decreased with increasing SSG concentration from 0 to $10^9$ cfu/mL applied one day prior to inoculation with *Calonectria pseudonaviculata* at $5 \times 10^4$ and $2 \times 10^4$ conidia/mL in the initial (I) and repeated experiments (II), respectively. Boxwood blight was assessed 7 days after inoculation. Data points represent mean leaves blighted (%) of three replicate plants and are presented with a standard error bar. Means marked with the same small case letter did not differ in the first run and those with the same uppercase letter did not differ in the repeated run according to the LSD test at p=0.05.

Blight incidence decreased (p<0.01) with increasing SSG cell concentration: 83% on boxwood pretreated with SSG at $3 \times 10^3$ cfu/mL and 1% on those at $3 \times 10^9$ cfu/mL in the initial experiment (FIG. 10). A similar decreasing trend was observed in the repeated experiment: 18% leaves blighted at $2 \times 10^5$ cfu/mL and 1/10 percent at $2 \times 10^9$ cfu/mL (FIG. 10).

Effect of SSG Treatment Lead Time on Boxwood Blight

Figure 11:
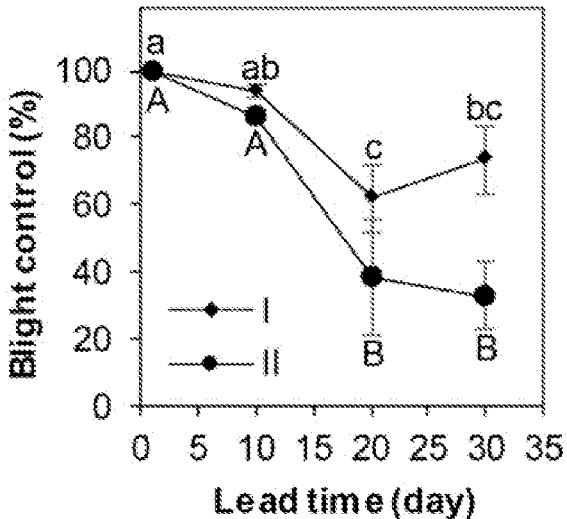
FIG. 11 shows blight control by SSG at $10^8$ cfu/mL decreased with increasing application lead time prior to inoculation with *Calonectria pseudonaviculata* at 1 to $2 \times 10^4$ conidia/mL. Each data point is a mean blight control of three replicate Justin Brouwers boxwood plants and is presented with a standard error bar. Means marked with the same small case letter did not differ in the first run and those with the same uppercase letter did not differ in the repeated run according to the LSD test at p=0.05.

When boxwood plants were cover sprayed with SSG at $4 \times 10^8$ cfu/mL prior to inoculation with Cps, significant differences were observed in blight control between two experimental runs (p=0.01) and four lead times (p<0.01). Blight control was over 99% in both runs when SSG was applied one day prior to inoculation with Cps, and the control efficacy decreased with increasing lead time (FIG. 11). Specifically, this decrease was significant between the lead times of 10 and 20 days, but not between 1 and 10 days, nor between 20 and 30 days in both runs.

Effect of Post-Inoculation SSG Treatment on Boxwood Blight

Figure 12:
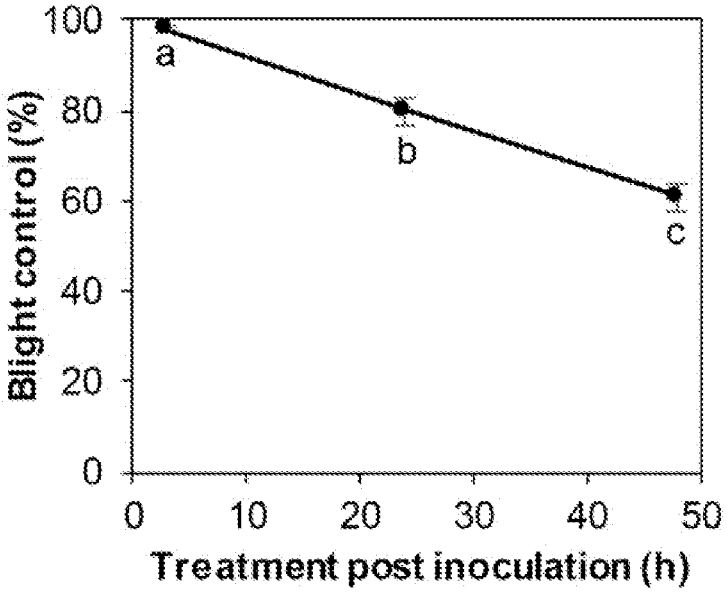
FIG. 12 shows blight control by SSG at $10^8$ cfu/mL decreased with increasing treatment time post inoculation with *Calonectria pseudonaviculata* at $10^4$ conidia/mL. Each data point is a mean blight control of six replicate Justin Brouwers boxwood plants from two experimental runs and is presented with a standard error bar. Data points marked with different letters differed according to the LSD test at p=0.05.

SSG applied 3 h post-inoculation reduced blight by 98% (FIG. 12). However, blight control decreased (p<0.01) with increasing time: 62% at 48 h post-inoculation. No difference was observed in blight control between two experimental runs (p=0.23).

SSG Effect on Potential of Diseased Leaves as a Source of Inoculum

Figure 13:
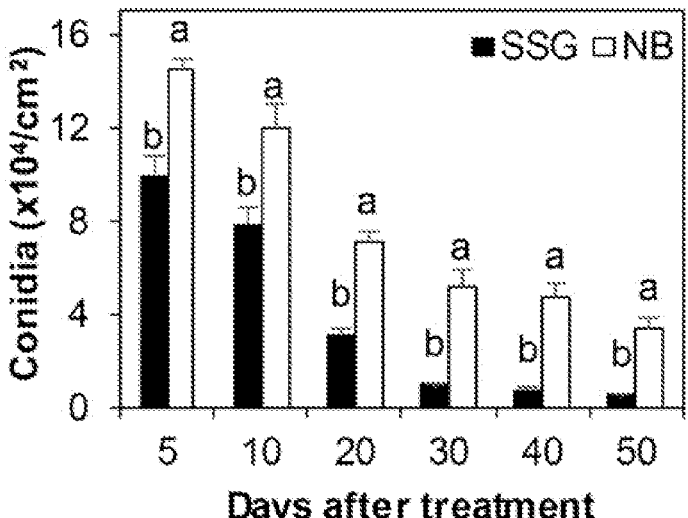
FIG. 13 shows SSG reduced sporulation by *Calonectria pseudonaviculata* on blighted leaves for a range of time after they were placed under healthy plants then cover sprayed with SSG suspension at $10^8$ cells/mL (SSG) or with nutrient broth (NB) as a control. Each column depicts an average of six replicates from two experimental runs and is topped with a standard error bar. Columns marked with different letters within each sampling time differed according to the LSD test at p=0.05.

More conidia were produced consistently on diseased leaf litter cover sprayed with NB than that treated with NB culture containing both SSG cells and metabolites in experiments (p<0.01, FIG. 13). Conidia production of both treatments decreased steadily with increasing post-treatment time (p<0.01). The number of conidia produced on NB-treated leaf litter was 144,542/cm$^2$ and 33,888/cm$^2$ at 5 and 50 days post-treatment, respectively. Likewise, the number of conidia produced on SSG-treated leaf litter was 98,756/cm$^2$ and 5,231/cm$^2$ at 5 and 50 days post-treatment, respectively.

Conidia produced on the leaf litter resulted in boxwood blight on the lower portion of Justin Brouwers plants. However, a higher percentage of leaves developed blight symptoms from the control litter cover sprayed with NB than those treated with SSG (11% vs. 1%, p<0.01). Difference was not observed in blight incidence between two experimental runs (p=0.25) nor among six assessment dates (p=0.70).

SSG population in sampled potting mix declined over the 50 day period (p<0.01) with 6×10$^9$ and 2×10$^6$ cfu/g at the beginning and termination of the study, respectively. The variety and population of other microbes recovered along with SSG also declined during the same period, and this decline was most obvious for fungi. SSG was never detected in control potting mix treated with NB.

SSG Species Identity and Differentiation from Epidemic Strains of *Burkholderia cepacia*

Several lines of evidence supported SSG's membership in the Bcc, although it does not seem to belong to any known species. It grew well in *B. cepacia* selective agar at 25° C. and 37° C., but not 42° C. Its 16S rDNA sequence also was 99% identical to many known species in the Bcc with *B. cepacia* JCM 2799 and *Burkholderia* sp. JJOA-S as the closest match when being blasted through NCBI and EzBio-Cloud, respectively. Likewise, its RecA gene sequence had the best alignment with that of *B. cepacia* strain IST431. When SSG RecA PCR products were digested with HaeIII and MnlI restriction enzymes, they produced a RFLP pattern that was similar to type "H" of genomovar III and type "d" of genomovar I, respectively. This result indicated that SSG belonged to neither genomovar I nor III because the expected RFLP pattern for genomovar I was "D" with HaeIII digestion, and for genomovar III was "g" with Mn/I digestion.

Figure 15:
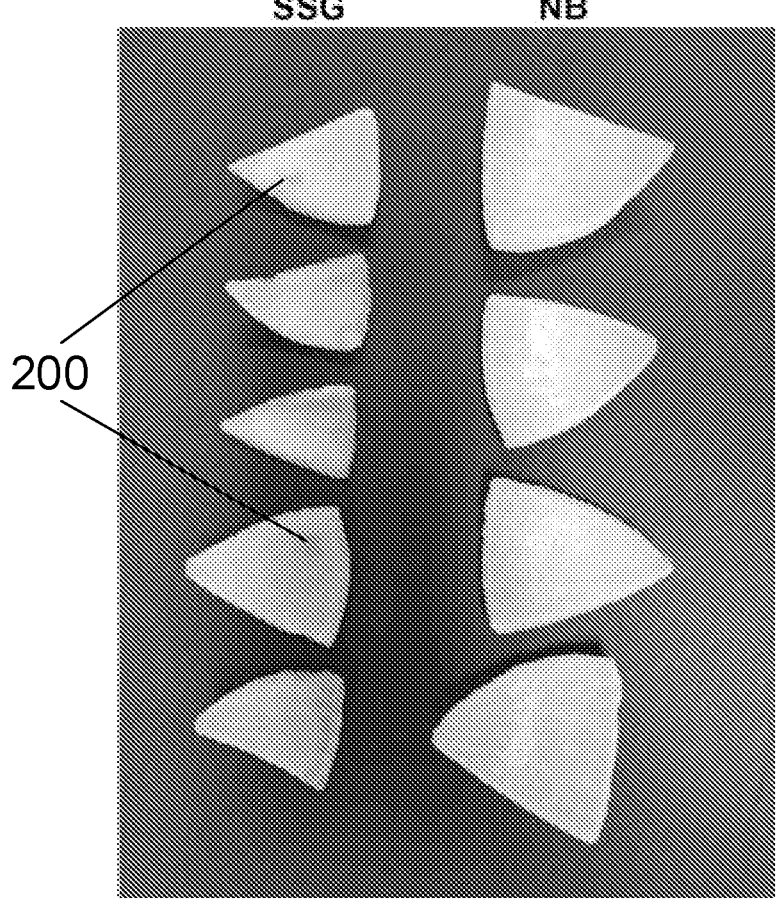
FIG. 15 shows symptoms on onion scales at 3 days after inoculation with a 10 µL drop of 48 h culture of SSG or nutrient broth (NB) control.

Both ID and RFLP indicated that SSG was distinct from all known clinical strains in the Bcc. In addition, SSG DNA was not amplified with the *B. cepacia* epidemic strain marker. Furthermore, unlike clinical strains, SSG macerated onion scale tissues (FIG. 15).

DISCUSSION

This study identified a potent *Burkholderia* endophyte, SSG, with both protective and curative properties against boxwood blight. As a protectant, SSG at 10$^8$ cfu/mL applied one day prior to inoculation with Cps provided almost complete protection of Justin Brouwers boxwood, a highly susceptible cultivar under high disease pressure environments (FIG. 11). This blight control efficacy is comparable to those of the most effective fungicides. In fact, it performed much better than the most effective biofungicides and all biocontrol agents identified to date, including Root-Shield Plus, non-indigenous isolates of *Trichoderma koningiopsis*, and *Pseudomonas protegens*, as well as an indigenous strain of *Pseudomonas lactis*. As a curative agent, SSG reduced blight by 98% when its cell suspension at 10$^8$ cfu/mL was applied 3 h after inoculation with Cps (FIG. 12).

In addition to directly protecting boxwood plants from infection by Cps, SSG greatly affected other major steps in the boxwood blight disease cycle. First, fallen diseased leaves are important sources of inoculum for new infection. SSG reduced the pathogen's ability to produce conidia on diseased leaf litter by 32% at 5 days after cover spray treatment; this reduction rate increased with time: 85% at 40 days and longer (FIG. 13). Second, conidia are the major dispersal and infective structure for boxwood blight. SSG at 10$^7$ cfu/mL completely lysed conidia while CFS had a similar but lesser impact. Together, SSG is an effective biological sanitizer and may be used to reduce the pathogen population at sites of infestation.

SSG may involve complex modes of action against Cps. First, some environmental Bcc species are known to produce unique antifungal antibiotics such as pyrrolnitrin, occidiofungin, and glidobactins. SSG may produce these antibiotics for suppression of Cps mycelial growth, although their species and mechanisms are yet to be elucidated. Second, SSG may also produce chitinases and glucanases that break down the cell wall building blocks, including chitin, glucans, and other polymers during the lysis process. The fact that conidia were lysed at a much greater rate in wells with live bacterial cells than those with CFS supports this hypothesis. Further studies on the molecular interactions between SSG and Cps are warranted to understand the modes of action by which SSG acts against Cps. It is worth noting that when Cps and SSG were grown in different sections of multisection Petri plates, no suppression was observed. Thus, the involvement of volatile compounds by SSG in Cps suppression is unlikely.

Many endophytes can elicit plant resistance during plant infection, and more than likely, SSG is able to do the same in boxwood against boxwood blight. This hypothesis is supported by the fact that boxwood plants remained moderately protected from infection by Cps even 20 days and longer after SSG treatment (FIG. 11). SSG may have elicited plant defenses that provide persistent resistance to the disease, although at low to moderate levels. Bcc bacteria survive poorly on leaf surfaces. The sustained blight control by SSG in the present study may also be due in part to their entry into plant tissue at a low rate that may continually act against Cps. Further study on the interaction between plant and SSG is warranted to elucidate the mechanisms underlying the sustained blight control.

Bcc is a very diverse *Burkholderia* group including some opportunistic human pathogens that are associated with lung infection in patients with cystic fibrosis. Although SSG belongs to Bcc, its profiles do not match with those of any known species in this complex and its likelihood of being a human pathogen is low. First, SSG was tested negative for BCESM, the standard human virulence marker used by the United States Environmental Protection Agency for registration of biocontrol products with Bcc as an active ingredient. With reference to FIG. 15, SSG macerated 200 fresh onion scales, a phenomenon not observed for known clinical strains. Additionally, SSG was isolated from surface-sterilized plant tissue whereas all clinical strains were isolated from human tissue or waste.

Although SSG may protect boxwood from infection by Cps for 3 to 4 weeks, longer than most fungicides currently labeled for protecting boxwood and/or controlling Cylindrocladium diseases, its efficacy decreased with time (FIG. 11). This reduction in SSG efficacy with time may be due in part to a declining bacterial population. Therefore, the second question of practical importance is how SSG interacts with boxwood and how its survival inside and on the surface of boxwood foliage may be improved for sustained high blight control performance. Formulation and delivery methods could have tremendous impacts on the performance of microbial biocontrol agents. So, an additional question is how SSG may be formulated and delivered to enhance its entry and survival inside and on the surface of boxwood plants for sustained survival and blight control performance. Nevertheless, this study identified a highly potent biocontrol agent with protectant, curative, and sanitizing properties.
Example 7: SSG Genome SSG genome DNA was extracted from overnight cultures in nutrient broth (BD, Sparks, MD) at 28° C. using Nucleo-Spin® Microbial DNA-Macherey Nagel (TaKaRa Bio, Bethlehem, PA) and quantified using Quantus™ Fluorometer (Promega, Madison, WI). Sequencing was performed on a MinION device (Oxford Nanopore Technologies, Oxford, United Kingdom). The sequencing library was prepared with the ligation sequencing kit (SQK-LSK109) according to the manufacturer's instructions and run in a FLO-MIN106 (R9.4.1) flow cell. Sequence basecalling was performed using MinKnow (Oxford Nanopore, Oxford, United Kingdom) at Q Score of 11 and run option of Fast5 for 20 h. Fastq files with a total of 9.46 Gb bases from 1.19 million reads that passed the Q score were used for de novo genome assembly using Canu version 1.8 with the default parameters for Nanopore data. After read correction and trimming, the final assembly from the retained single largest high-quality chunk of sequences resulted in a sequence with a total length of 8,571,737 bp and an average GC content of 66.9% arranged in six contigs. The genome coverage is 108.64-fold (N50=5,470,797) (Table 2). The assembly was annotated using Prokka 1.14.1 and Rast 2.0. Prokka predicted 9039 protein-coding sequences (CDS) and 76 tRNA, nine rRNA and one tmRNA. Rast predicted 10209 CDS, 67 tRNAs, 18 rRNAs and one tmRNA.

TABLE 2

| Genome Features of *Burkholderia* sp. SSG | |
|---|---|
| Feature | Value |
| Genome size (bp) | 8,571,737 |
| GC content (%) | 66.9 |
| Secondary metabolism gene clusters | 866 |
| Coding sequence | 10209 |
| tRNA | 67 |
| rRNA | 18 |
| tmRNA (transfer messenger RNA) | 1 |

Eight hundred and sixty-six secondary metabolism gene clusters were detected through Rast analysis. 15 gene clusters related to antibiotic biosynthesis were detected with antiSMASH 5, which included genes for nonribosomal peptide synthetase (NRPS), polyketide synthase (PKS), pyrrolnitrinis and bacteriocin production (Table 3). These clusters accounted for 6% of the genome assembly. This genome capacity for antibiotic biosynthesis is more than twice that of other analyzed Bcc species. This feature of SSG is consistent to its potent antagonism we observed on oomycete, some bacterial and fungal pathogens. Interestingly, except for gene cluster for biosynthesis of terpene that has been used for pesticide (Table 3), through Prokka and Rast annotation, we identified genes for production of insecticidal photopexin and presqualene diphosphate synthase (hpnD).

TABLE 3

| Predicted Secondary Metabolite Clusters Involving Antibiotic Biosynthesis | | | | | | |
|---|---|---|---|---|---|---|
| Cluster | Number | Contig | Average size (bp) | % in the genome | Examples | Potential Applications |
| Non-ribosomal peptide synthetase (NRPS) | 3 | 1 & 6 | 52601 | 1.84 | Pyochelin, ornibactin | Cytotoxic antibodies |
| Polyketide synthase (PKS) | 2 | 1 | 46054 | 1.07 | Polyketide, myxochromide D, capsular polysaccharide | Antibiotic, anticancer agents |
| tRNA-dependent cyclodipeptide synthases (CDPS) | 1 | 79 | 22042 | 0.26 | Cyclodipeptide | Antifungal, antiviral (influenza A), anti-multidrug resistant bacterial, and anticancer agents |
| Terpene synthase | 5 | 1, 19, 79 | 21463 | 1.25 | Terpene | Pesticides |
| Aryl polyene | 1 | 19 | 41210 | 0.48 | Polyene | Antioxidants, antibiotics |
| Bacteriocin | 1 | 79 | 10758 | 0.13 | Protein TolQ, Colicin V synthase | Antibacterial drug |
| Phosphonate | 1 | 1 | 40578 | 0.47 | Phosphinothricin tripeptide | Antifungal and anti-oomycete agent |

TABLE 3-continued

| Predicted Secondary Metabolite Clusters Involving Antibiotic Biosynthesis | | | | | |
|---|---|---|---|---|---|
| Cluster | Number | Contig | Average size (bp) | % in the genome | Examples | Potential Applications |
| Other | 1 | 79 | 41082 | 0.48 | Pyrrolnitrin | Antibacterial, antifungal, and anti-oomycete agent |

Many genes involving plant growth promoting traits were also identified through manual annotation (Table 4). These included genes for nitrogen fixation including a nitrogenase gene (eg. NifQ) and a hgIE cluster or heterocyst glycolipid synthase-like PKS involving nitrogen fixation in cyanobacteria heterocyst as well as other genes for nitrogen fixation and regulation including pstN and glnB. There were also genes for phosphate solubilization (glucose dehydrogenase and pyrroloquinoline quinone (PQQ)) synthesis proteins for organic acid production, siderophore production for iron binding and transfer as well as genes for plant growth hormone production or modulation such as auxin biosynthase and ethylene metabolism.

TABLE 4

| Predicted Genes/Products Involving Plant Growth Promotion Traits (PGPT) | | | | | |
|---|---|---|---|---|---|
| Gene/product | Number of genes (>) | Example | Contig | PGP trait | Potential application |
| Coenzyme pyrroloquinoline quinone (PQQ) | 5 | pqqB, C, D, E | 1, 79 | Plant defense, production of glucose dehydrogenases (GDHs) | Plant stress resistant elicitor, gluconic acid production, antioxidant, antineuroinflammatory drug production |
| Hydrogen cyanide synthase | 6 | HcnB, C | 1 | Regulating availability of phosphate | Biofertilizer |
| Proteins in butanediol metabolic process | 2 | BudC | 2, 19 | Plant defense | Plant resistant elicitor |
| Nitrogen metabolism and transport | 4 | gdh, glnB, ptsN | 19, 89 | Regulating nitrogen utilization | Biofertilizer |
| Urea degradation | 20 | ureA-I, allA, alc, pucl | 1, 19, 79 | Regulating nitrogen utilization | Biofertilizer |
| 1-aminocyclopropane-1-carboxylate deaminase (ACC) | 1 | acdS | 1 | Reducing plant ethylene levels | Plant growth regulator |
| Tryptophan synthase | 2 | trpA, B | 1 | Auxin production | Plant growth regulator |
| Biotin biosynthesis and transport | 9 | accB, C, BioB, C, D, madC | 1, 2, 6, 19 | Seed development | Plant seed production |
| Gluconic acid production | 5 | GDHs, gdhl, IV | 1, 19, 79 | Phosphate solubilization | Biofertilizer |
| Siderophore biosynthesis, transport and liberation of iron | 102 | yusV, TonB | All 6 | Iron uptake, phosphate solubilization by production of chelating substance | Plant growth regulator |

These results supported SSG as a possible potent biocontrol agent for plant diseases. They also indicated that SSG may also be a candidate biocontrol agent for insect pests and a biofertilizer.

SSG was identified as *B. cepacia* through genome-based identification on TrueBac™ ID. The average nucleotide identity (ANI) between the genomes and the type strain of *B. cepacia* was 98.4%. (ANI coverage of 94.8%). However, multilocus sequence typing (MLST) of the SSG genome sequence revealed that SSG contains only three of the seven loci that are used for differentiation of species in the Bcc.

Although SSG had the same allele number at atpD as two strains of Bcc (BCC0412, IST431) and the same allele number at lep as one strain (BCC0218) of Bcc in genomovar I, the overall SSG allelic profile did not match any Bcc that has been listed previously, indicating divergence of SSG from other species in this genomovar that uses *B. cepacia* as a representative.

Clinically important isolates of Bcc are most commonly members of genomovars II and III, with few human pathogens contained within genomovar I. To determine if SSG was different from clinical strains, we searched for the cable pilin gene encoding *Burkholderia cepacia* epidemic strain marker (BCESM) in the predicted CDS by Prokka and Rast. We did not find any CDS for the gene, indicating an absence of BCESM, which is consistent with PCR results in a previous study. Together with the presence of genes involving in nitrogen fixation that is a missing trait in clinical Bcc strains, SSG is a unique member of the Bcc which is distinct from clinical strains and appears to have great promise for agriculture and biotechnology applications.

Example 8: Materials and Methods for Characterization of Boxwood Endophytic *Burkholderia cepacia* SSG as a Plant Growth Promoter Isolate and Culture

*Burkholderia* sp. SSG isolate was deposited at the Virginia Tech Collection of *Phytophthora* and Beneficial Microbes (VTC) of the World Data Center for Microorganism (WDCM1197). SSG was grown on potato dextrose agar (PDA or nutrient agar (NA) or in nutrient broth (NB) (Becton, Dickinson and Company, Spark, MO, USA) for 48 h at 25-28° C. The culture was maintained at 4° C. within a month after growth and stored at −80° C.

IAA Production

IAA production by SSG was determined quantitatively using a published colorimetric method with a minor change. A single colony of SSG on a streak plate was transferred into four milliliters of NB containing four milligrams of tryptophan. After a 72-h incubation at 28° C., 1.5 mL SSG broth culture and NB without SSG as control was centrifuged at 13,523×g for five minutes, 0.5 ml of the supernatant was then mixed with one milliliter of Salkowski's reagent in a 1.5-mL tube. The mixtures were incubated at 23° C. for 30 min, then measured for absorbance at 530 nm after blanked with the control on Du®800 spectrophotometer (Beckman Coulter, Indianapolis, IN, USA). The assay was run in triplicate and repeated once. The result was quantified using a standard curve of known IAA dilution series (Sigma-Aldrich, St. Louis, MO, USA) at a range of 0.1 to 300 μg mL-1.

Nitrogen Fixation Ability

The nitrogen fixation ability of SSG was determined by growing SSG on nitrogen-free agar medium. Specifically, nitrogen-free agar plates were streaked with fresh SSG colonies on a PDA plate. Meanwhile nutrient agar plates as source of nitrogen were also streaked as positive control. After a four-day incubation at 25° C., the plates were examined for bacterial growth. The assay was conducted in triplicate and repeated once.

Phosphate Solubilization

The ability of SSG to solubilize phosphate was determined using the National Botanical Research Institute's Phosphate (NBRIP) medium broth or plate and colorimetric method with minor modifications. For the plate assay, three sterilized Whatman filter paper disks were placed as an equilateral triangle in NBRIP agar plates. A 10-μL aliquot of SSG cell culture stock was added to each disk. Control disks received the same amount of nutrient broth without SSG. All plates were examined for the development of halo around the disks after incubated at 27° C. for seven days. For the broth colorimetric assay, 150 mg $Ca_3(PO_4)_2$ as an insoluble form of phosphate was included in a 30 mL NBRIP broth. In the broth, 0.3 mL of overnight SSG culture in NB or NB alone was added. After incubated on a shaker at 27° C. for seven days, the broth was centrifuged at 13416×g for 10 min. The supernatant was autoclaved for 20 min and stored at 4° C. To determine soluble phosphate release into the solution, one milliliter of the supernatant or its dilution of samples was added with two milliliters of 2.5% ammonium molybdate and 0.5 ml of 10 M sulfuric acid, then mixed with one milliliter of 0.5 M hydrazine hydrate solution and filled with SDW to 25 mL. The resultant solutions were blanked with the supernatant of the control and measured for the absorbance at 840 nm on the spectrophotometer (Beckman Coulter, Indianapolis, IN, USA). When the absorbance of a sample was one or smaller, soluble phosphate in the sample was calculated with the formulation: sample absorbance/0.1235+0.0018. When the absorbance of a sample was one or greater, it was calculated with diluted samples. Both assays included three replicates and were repeated once.

Siderophore Production

Siderophore production by SSG was determined using a blue agar medium containing chrome azurol S (CAS) and the indicator hexadecyltrimethylammonium bromide. Specifically, the media plates were streaked with SSG and incubated at 25° C. Plate color change was examined after 48 h. Plates with a color change from blue to yellow were recorded as positive. This assay included three replicate plates, and the assay was repeated twice.

Plant Treatment and Growth Measurement

Three boxwood cultivars of different growth rates, *Buxus sempervirens* 'Justin Brouwers' (slow), 'Buddy' (intermedium) and *B. microphylla* var. *japonica* 'Winter Gem' (fast) were used in this study. These cultivars with two plants were grown in 3.8-l containers and maintained in a greenhouse before use. One week before SSG treatment in November 2018, plants were pulled out containers, separated and weighed after the potting mix was removed and plants were rinsed with tap water. Weighted individual plants were repotted with a mixture of Scotts® Premium Potting Soil (Marysville, OH) and pine barks (Pacific Mulch Inc, Henderson, NC) at ⅓ to ⅔ ratio in 3.8-L containers. These plants were watered manually to saturate the soil after potting, then drip-irrigated every other day for one min.

Plants were inoculated by drenching SSG cell suspension. To prepare SSG cell suspension, 150 mL of NB was inoculated in a flask with one milliliter of the stock, an overnight culture of SSG in NB, and incubated at 28° C. on a shaker for 40 h. Three flasks of the culture were used for an experiment. The culture was centrifuged at 8,275×g for 15 min to precipitate cells that were resuspended in 500 mL Phosphate-Buffered Saline (PBS) (pH=7.4) after supernatant was removed. A 50-mL aliquot of SSG resuspension at $10^8$ cfu/mL or the same amount of PBS was evenly poured onto the potting mix around plants in a container. After treatment, containers were arranged in a randomized complete block design and dripping irrigation was resumed for plants in two days. In March 2019, plants were moved from the green house to a gravel pad outside where they were overhead irrigated. In September 2019, plants were pulled out again and weighted after root cleaning as done at the beginning of the experiment in November 2018. The monthly growth rate was calculated by dividing the difference in plant weight between measurements at the beginning and end of the experiments by 10 for each replicate of cultivar and treatment combination. The experiment was conducted three times.

Statistical Analysis

Plant growth data from three repeated experiments were subjected to homogeneity test and subsequently pooled for further analyses. Analysis of variance was conducted using the Statistical Analysis Software Version 9.4 (SAS Institute, Cary, NC). Treatment means were separated by boxwood cultivar according to the least significant difference at P=0.05.

Figures 17A, 17B, 17C, 17D, 17E, 17F, 17G, 17H:
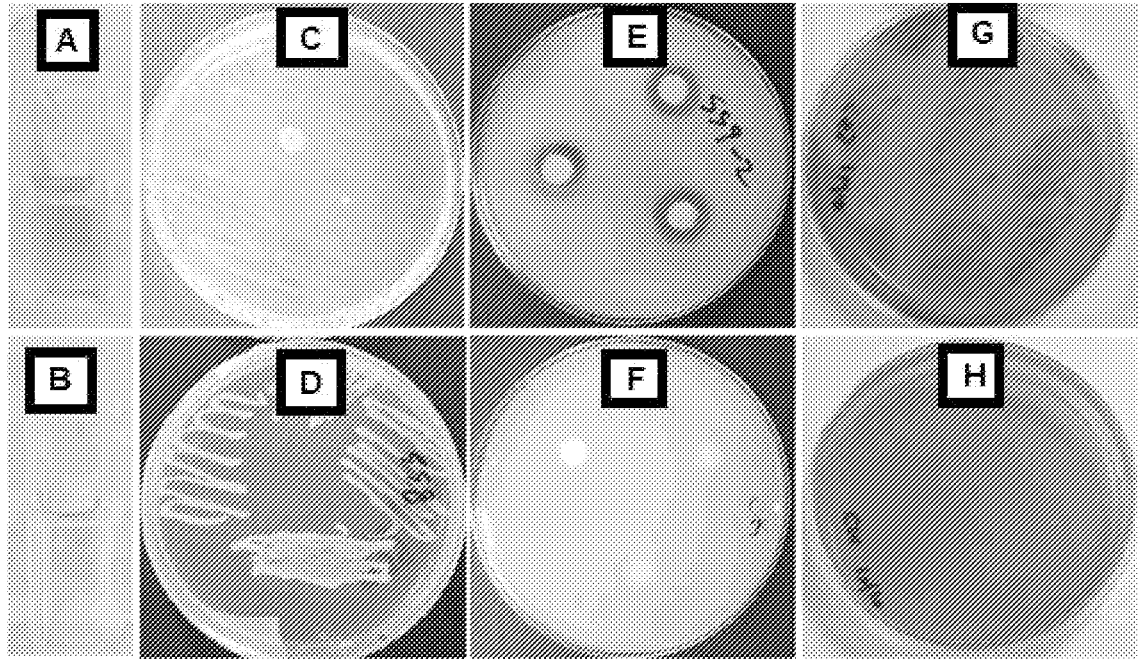
FIGS. 17A-17H show SSG plant growth-promoting traits as shown in a colorimetric or plate assay.

Example 9: Results and Discussion for Characterization of Boxwood Endophytic *Burkholderia cepacia* SSG as a Plant Growth Promoter Indole-3-Acetic Acid (IAA) Production IAA was detected in the cell-free supernatant of SSG culture two days after NB broth containing tryptophan was inoculated (FIGS. 17A, 17B). The estimated yield was 2.9-4.5 µg/mL that had no change with increasing growth time. No color change was observed in the same medium that was not inoculated with SSG. These results indicated that SSG was able to produce IAA. It is not clear whether this IAA yield of SSG is common in IAA producing *Burkholderia* due to lack of quantitative data for other *Burkholderia*. However, it is relatively low compared to some non-*Burkholderia* bacterial endophytes that produce 9.6-43 µg IAA/mL. Surprisingly, genes encoding tryptophan-2-monooxygeanse or tryptophan transaminase were not found in the SSG genome despite that there are genes for tryptophan production. These enzymes play important roles in the pathways of tryptophan-dependent IAA biosynthesis in bacteria (*Pseudomonas* and *Agrobacterium*) and plants. SSG producing IAA in the experiment without these genes suggests that this bacterium may use a different pathway from those currently known, which remains to be investigated.

IAA is the basic and most potent auxin natively occurring and functioning in plants and it regulates leaf and flower development. SSG is the first IAA-producing burkholderial bacterium from boxwood leaves based on our knowledge, while other IAA-producing *Burkholderia* are found in stem, root, and rhizosphere. SSG can survive in soil, indicating that it may also be a rhizosphere endophyte. This bacterium might have been as a boxwood symbiont facilitating the growth of plants, although whether and how SSG may move in the plant deserve a further investigation.

Nitrogen Fixation

SSG grew on the N-free medium, indicating its ability to fix atmospheric nitrogen (FIGS. 17C, 17D). This trait is expected as the SSG genome contains a nitrogenase gene (eg. NifQ) and a hgIE cluster, heterocyst glycolipid synthase-like PKS involving nitrogen fixation in cyanobacteria heterocyst, as well as other genes for nitrogen fixation and regulation such as pstN and glnB. Nitrogen fixation has been found in various endophytic bacteria although it is not common for Bcc. As a new nitrogen-fixing member of Bcc following B. vietinamiensis, SSG may be a great resource of boxwood plants in nitrogen acquisition and metabolism.

Phosphate Solubilization

Phosphate solubilization of SSG was evaluated using milky NBRIP agar media (FIGS. 17E, 17F). Around disks with SSG there was a clear halo initially seen on the third day of placing the disk. The halo enlarged with increasing incubation time. On day seven, the halo was evident and had diameter 14 mm (±0.3). No halo was present in any control plate without SSG. Weak phosphate-solubilizing bacteria do not display halo in the plate assay. The halo formulation with SSG suggests that the bacterium is a potent phosphate solubilizer. The solubilized phosphate was 206.4 ppm (±5.0) as estimated on the seventh day after treatment using a colorimetric method by which solubilization of $Ca_3(PO_4)_2$ in the broth remained detectable after the sample was diluted 100-fold. This amount was about four percent of the insoluble form of phosphate, which is slightly lower than that of other reported strong phosphate solubilizing bacterial endophytes, including *Burkholderia* spp. This difference among bacteria may have resulted from quantification methods used for insoluble phosphate. In this study we used the colorimetric method instead of the optical density of the broth. Phosphate-solubilizing bacteria can improve crop yield when used to inoculate seed or soil due to the release of insoluble and fixed forms of phosphorus. As a member of these bacteria, SSG is a great phosphorus resource for plants.

Siderophore Production

Siderophores from microorganisms can be used by the plant as an iron nutrient source, alleviating the stresses imposed on plants by high levels of heavy metals in soil and plant pathogen suppression. SSG was a strong siderophore producer, as indicated by decolorating blue chrome azurol S agar 48 h after the plate was streaked with SSG (FIGS. 17G, 17H). No color change occurred in control plates. This is supported by SSG genome sequencing showing that there are more than 100 genes or copies involving in siderophore biosynthesis, assembly and metabolism. However, further studies are warranted to understand how these siderophores may be used for plant growth promotion.

Effect of SSG as Inoculant on Boxwood Plant Growth

Figure 18:
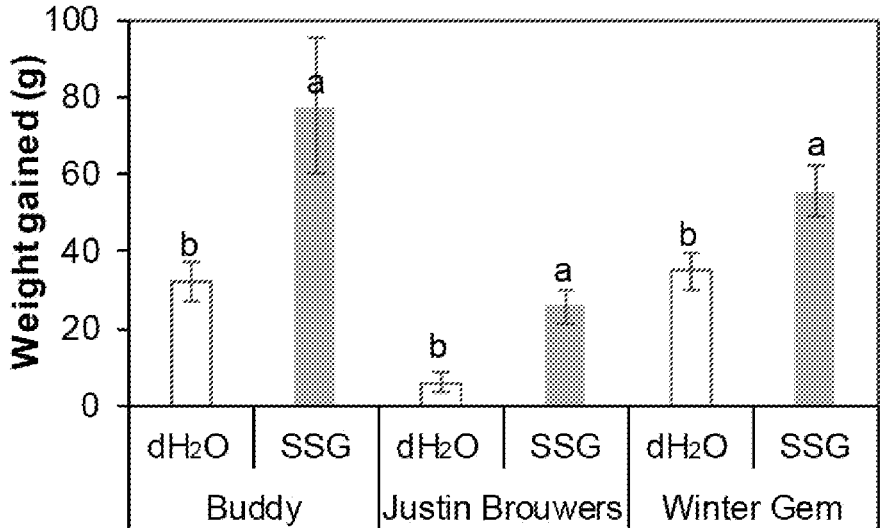
FIG. 18 shows boxwood plant growth of three cultivars-Buddy (intermediate), Justin Brouwers (slow) and Winter Gem (fast) as affected by SSG cell suspension (SSG) or control (dH$_2$O) drench over a 10-month period. Each column is a mean of 9 replicate plants from three repeated experiments. Standard error bars are presented on top of the columns. Columns within each cultivar topped with different letters differed according to the least significant difference at P=0.05.

SSG was used to inoculate boxwood roots to evaluate whether it may stimulate plant growth over a 10-month period. Plant growth showed no difference between three repeated experiments (P=0.6905) nor interaction between cultivar and treatment (P=0.2121), cultivar and experiment (P=0.1366) and between treatment and experiment (P=0.2434). However, there was significant difference between SSG inoculated and uninoculated treatments, although the difference varied with cultivar (P<0.0001). SSG consistently promoted plant growth of all three boxwood cultivars when compared to PBS. Specifically, SSG resulted in an increase of monthly growth rate that is 58%, 76%, and 37% greater than that of the control in Buddy (P=0.0236), Justin Brouwers (P=0.0014), and Winer Gem (P=0.0190), respectively. Leaf number increase has been observed for boxwood Justin Brouwers in containers with diseased leaf debris that was sprayed with SSG culture in a previous study of boxwood blight control with SSG. In that study, it was not certain whether the leaf increase resulted from plant growth or disease reduction. This study confirmed SSG as a plant growth bacterium contributing to the new growth of leaves. Justin Brouwers is a slow growth boxwood cultivar while Buddy and Winter Gem are medium and fast growth cultivars, respectively. SSG appeared more effective on promoting slow and medium growth plants than fast growth plants (FIG. 18). This study demonstrated the ability of SSG to produce IAA and siderophore, fix nitrogen and solubilize phosphorus as predicted by the genome sequencing. These features, together with its other features such as potent antagonism against pathogens and low human health risk may allow SSG to become a prospective biocontrol agent and PGPB in agriculture.

Example 10: Materials and Methods for *Burkholderia cepacia* SSG as a Broad-Spectrum Antagonist for Suppression of Multiple Plant Diseases Microorganisms and their Growth Conditions Except for SSG and tomato spotted wilt virus, information of other microbes used in this study were listed in Tables 5 and 6. Potato dextrose broth (PDB), nutrient broth (NB) (Sigma-Aldrich, St. Louis, MO, USA), or 5% clarified V8 medium broth (V8B) and their agar plates were used for culture and growth of fungi, bacteria, and oomycetes, respectively at 23-28° C. depending on the experiment.

Dual Culture Assay

Dual-culture assays were performed differently on agar medium plates depending on target microorganisms. For fungi and oomycetes, a 0.45 cm diameter plug of a week-old agar culture was placed in the center of a PDA plate between two streaks of SSG overnight broth culture or two streaks of NB medium as the control. Diameters of the targets were measured 1-4 weeks after the plates were incubated at 25° C. For target bacteria, 100 μL of overnight culture in NB were spread on NA plates, and three sterilized disks (0.7 cm in diameter) of Whatman filter paper No. 1 were placed at three angles of an equilateral triangle in the center of the plates, and each was dropped with 10 μL SSG cell culture stock or NB as the control. Diameters of suppression halo zone from the disks were measured 72 h after the treatment at 25° C. For each target isolate/strain, three replicate plates were included. Each assay was repeated at least twice.

Phytophthora Zoospore Germination Suppression by SSG

While germination suppression of fungal conidia by SSG has been reported, this study focused on zoospore germination suppression. P. capsici was used for easy zoospore production as described previously. 100 μL of zoospore suspension at $10^5$/mL was added into 1 mL PDB containing 50 μL SSG cell suspension at $10^7$ cfu/mL, SSG culture cell-free supernatant (CFS) or the control PDB alone in a well of 6-well plates. Four replicate wells were used for each treatment and examined for morphological changes of zoospores under a microscope 24 and 48 h after the addition of zoospores. The assay was repeated once.

Plants and Growth Conditions

Eleven plant species/cultivars were used for disease suppression experiments with SSG. They were started from seed, seedlings or grown plants at Hampton Roads Agricultural Research and Extension Center (HRAREC). Experimental plants were watered with a drip or overhead irrigation programmed for best growth of plants and maintained greenhouse or gravel pad at HRAREC before use.

Annual vinca (Catharanthus roseus 'Little Bright Eye') and pepper (Capsicum annuum L. 'California Wonder') plants were started from seeds as described previously. Plants were grown in the greenhouse for 4-8 weeks before use after transplantation with 2-3 seedlings per pot with dimensions of 15.9×14.7 cm.

Two-year Fraser fir (Abies fraseri) seedlings and 6-8-week seedling plugs of garden pansy (Viola tricolor var. hortensis), geranium (Pelargonium 'American White'), impatiens (Impatiens walleriana 'Beacon Orange'), and petunia (Petunia×hybrida 'Wave® Misty Lilac Hybrid') were purchased from nurseries. All the seedlings were transplanted, grown in pots with dimensions of 15.9×14.7 cm and used after 6-8 weeks.

Potting mix used for transplanting contained 89% unamended aged pine bark (Pacific Organics, Henderson, NC, USA), 10% Metro-Mix 830 (Sungro Horticulture, MA, USA), 0.59% 16-6-11, 5-6 month-controlled release fertilizer (CRF) (Harrell's, Lakeland, FL, USA), 0.06% Nitroform (Agrium Advanced Technologies, ON, Canada), 0.27% Pro Pulverized Limestone and 0.14% Pro Granular Limestone (Oldcastle Lawn & Garden, PA, USA) for a pH at 6.5-7.

Boxwood 'Green velvet' (B. sempervirens×B. microphylla var. koreana), hydrangea (Hydrangea paniculata 'Limelight'), and rhododendron (Rhododendron catawbiense 'Boursault') plants were gifts grown in pots with dimensions of 15.9×16.5 cm, 25.4×22.9 cm and 15.9×16.5 cm, respectively. Hydrangea plants were pruned back to promote new growth and fertilized with CRF two months before use. All plants were watered with a drip or overhead irrigation and maintained in the greenhouse or grovel pad at HRAREC before use.

Inoculum Preparation

Overnight broth culture SSG was used as a stock to make an inoculum for a plant treatment before or after inoculation with a pathogen. 350 mL NB was added to 1 mL of the stock and shaken for 40 h at 28° C. to get culture at a concentration range of $10^8$ cfu/mL as described in a previous study. The control was NB or sterile distilled water (SDW) depending on the suspension used.

Foliage inocula of Phytophthora including P. capsici, P. nicotianae, and P. ramorum were prepared with zoospores produced as described previously, respectively. P. nicotianae used for root inoculum was isolates from petunia (30J5 and 31A3). Concentrations of zoospore suspensions were adjusted with soil water extract to one at a range of $10^4$ zoospores/mL. Inoculum of P. cinnamomi used three isolates (28D5, 28E3, 28E6) from Fraser fir was made with 25 g double autoclaved Mahatma long grain rice soaked 18 mL $dH_2O$ in a 250-mL flask. The rice was inoculated with four agar culture plugs and incubated at 23° C. The inoculum was ready in about 10 days, during which the flask was tapped daily to redistribute grains until grains became powdery white.

Inocula of fungi including Collectortrichum fruticola, C. gleosporiodes, Botrytis cinerea, and Volutella buxi were prepared with conidia produced from 10 to 14 days old PDA cultures. Concentrations of conidial suspensions were adjusted with 0.01% polysorbate 20 to a range of $10^{5-6}$ conidia/mL.

Inoculum of Xanthomonas campastris was prepared from 3-day culture of the bacteria at 30° C. on PDA plates. At inoculation, the culture was resuspended in 0.01% polysorbate 20 to have a concentration of $8×10^7$ cfu/mL determined with a previously described platting method used for SSG.

Infected tomato plants with typical symptoms of tomato spotted wilt in a vegetable garden at HRAREC were used as inoculum source of TSWV for impatiens natural inoculation. Prior to inoculation, a pathogenicity test was conducted using a symptomized leaf sap. Specifically, the collected diseased leaf was cut and ground in a small volume of 0.01 M phosphate buffer at pH 7.0 with carborundum (Fisher Scientific, NJ, USA). The 10-fold diluted sap and sap from healthy leaves as the control were used to gently rub impatiens leaves. Plants inoculated with the sap from diseased plant showed necrotic spots after a few days, indicating diseased tomato plants could be used as an effective inoculum source.

Plant Treatment with SSG

For foliage treatment with SSG, plants were placed in moist chambers and applied with the inoculum or the control with a hand sprayer until dripping before or after inoculated with a pathogen inoculum, lead times for pretreatment with SSG before inoculation included one day (1 db), one week (1wb), two (2wb) or four weeks (4wb). Post-time treatment with SSG after inoculation with a pathogen was 3 days (3da). For each treatment, 3 replicate pots were included. Treated plants were removed from the moist chamber the next day and overhead irrigation was resumed on the third day after treatment.

For root treatment, each Fraser fir or petunia plant in a pot was drenched with 50 mL SSG inoculum or NB. Each treatment pot containing 3 replicate plants. Irrigation remained the same after treatment.

Plant Inoculation with a Pathogen

Pathogen inoculation was conducted at one day, one week, two weeks, or 4 weeks after the treatment or three days before the treatment. Prior to inoculation, SSG treated and control plants were arranged with a randomized block design. For foliage inoculation with a fungus or Phytoph-

*thora*, the inoculation was conducted with a hand sprayer as did for SSG. For inoculation with *X. campestris*, plant leaves were injured with push pins, five pinches per leaf, and then sprayed with the bacterial inoculum. Inoculated plants were kept in a moist chamber for 48 h before placed in a shade area with mist or hand watering until disease rating.

Inoculation of root pathogens used two methods. For P. cinnomomi, it was done with rice grain inocula. Four grains were placed in a hole at each of three plants in a pot. For *P. nicotianae*, it was done by drenching 5 mL inocula around the crown of each plant. Overhead irrigation was not disrupted before plants were rated for diseases. Natural inoculation (*thrips*) was conducted for TSWV. SSG treated or control *impatiens* plants were placed in a place surrounded by diseased tomato plants in the vegetable garden where 30 min/day overhead irrigation was carried out.

After a week of exposure, plants were moved back to the gravel pad with regular irrigation. Plants were assessed 10-20 days after inoculation for disease severity with a 1-10 scale: 1=1-10%, 2=11-20% up to 10=91-100% infection of plants or plant parts. Each experiment was repeated at least once.

Data Analysis

Data from each experiment and phytopathosystem were analyzed using the Microsoft Excel 2010 data function. Statistics used standard analysis of variance (ANOVA) Two-Factor with Replication or t-Test assuming equal variance at a (significant level)=0.05. Standard errors were calculated for all mean values based on standard divination (StdDevp) and replicate.

Example 11: Results and Discussion for *Burkholderia cepacia* SSG as a Broad-Spectrum Antagonist for Suppression of Multiple Plant Diseases SSG Inhibits Culture Growth of Three Groups of Pathogens SSG was cross cultured with three groups of microorganisms, bacteria, fungi and *Phytophthora*. Except for *E. coli*, all of the test isolates were from plants. SSG significantly inhibited growth of nine fungal, six oomycete and five of six bacterial species tested (Table 5).

TABLE 5

| | Suppression of Microorganisms by SSG in a Dual Culture Assay | | | | | | |
|---|---|---|---|---|---|---|
| Group | Species | Isolate | Source | Suppression[x] | SE[y] | P Value[z] |
| Bacteria | *Escherichia coli* | DH52 | ATCC | 12 | 0.7 | <0.0001 |
| | *Erwinia carotovora* | 60624 | Iris | 0 | 0 | 1 |
| | *Pseudomonas syringae* | 60625 | Tomato | 22 | 1.0 | <0.0001 |
| | *Raistonia solanacearum* | 60626 | Tomato | 4 | 0.2 | <0.0001 |
| | *Stenotrophomonas maltophilia* | SY (PE1) | Boxwood | 21 | 0.5 | <0.0001 |
| | *Xanthomonas campestris* | 60627 | Begonia | 28 | 0.3 | <0.0001 |
| Fungi | *Alternaria tenuissium* | PC2 | Pansy | 73.7 | 1.1 | <0.0001 |
| | *Botrytis cinerea* | PC4 | Pansy | 53.9 | 1.4 | 0.0001 |
| | *Collectortrichum acutatum* | Imp2 | Impatiens | 70.8 | 0.6 | 0.0002 |
| | *C. frutticola* | PS5 | Pansy | 68.5 | 1.1 | 0.0007 |
| | *C. gleosporiodes* | Hyd1 | Hydrangea | 64.3 | 1.0 | 0.0014 |
| | *C. viniferum* | Imp1 | Impatiens | 63.3 | 0.9 | 0.0013 |
| | *Fusarium proliferatum* | Carl | Carnation | 69.9 | 1.0 | 0.0001 |
| | *F. solani* | 11b07 | Sweet box | 83.7 | 0.7 | <0.0001 |
| | *Volutella buxi* | 11A10 | Boxwood | 87.7 | 1.9 | <0.0001 |
| Phytophthora | *P. capsica* | 22H3 | Pumpkin | 80.9 | 0.8 | 0.0001 |
| | *P. cinnamomi* | 30D6 | *Ilex glabra* | 74.6 | 2.2 | 0.0002 |
| | *P. infestans* | 27E7 | Tomato | 94.4 | 0 | 0 |
| | *P. nicotianae* | 1B11 | Annual vinca | 81.5 | 1.8 | 0.0002 |
| | *P. ramorum* | 32G2 | Camellia | 91.3 | 0.5 | <0.0001 |
| | *P. sojae* | 28G4 | Soybean | 81.6 | 1.3 | <0.0001 |

[x]Suppression of bacteria is indicated by halo diameter (mm) around disk with SSG. Suppression of fungi and *Phytophthora* by SSG is indicated by percentage of inhibited culture growth compared to the control 4 weeks after the cross.

[y]is the standard error of 9 replicates in 3 assays.

[z]results from t = test at $\alpha$ = 0.05.

Figure 16A:
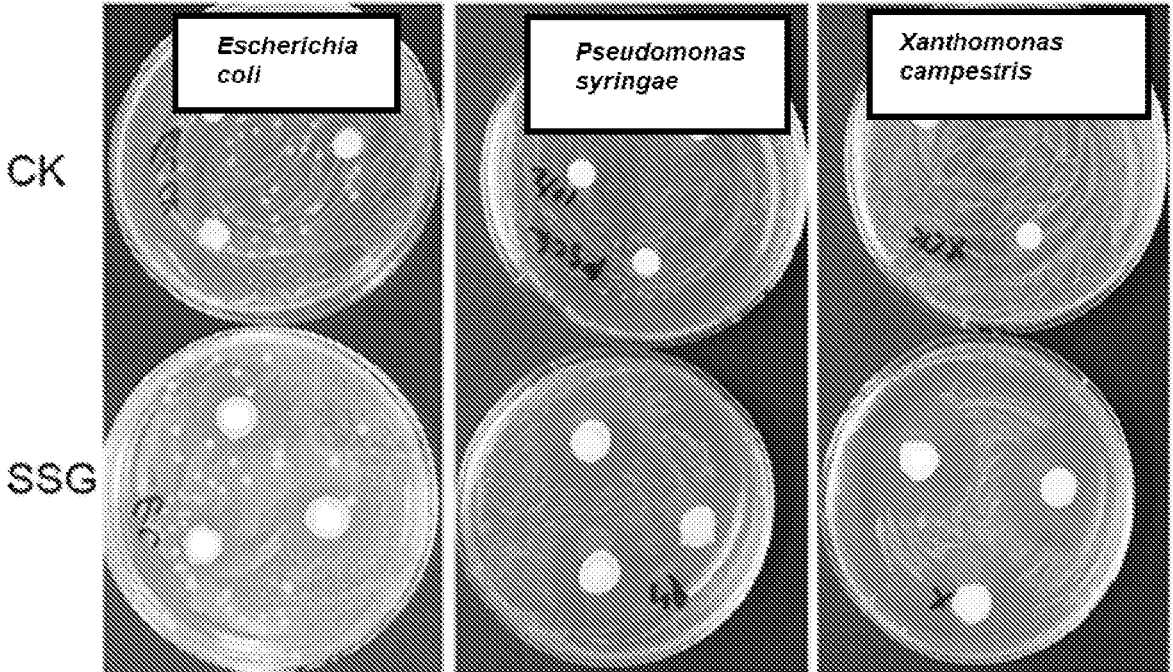
FIGS. 16A-16C show dual culture assays of microbial culture suppression by SSG at 25° C. Pictures were taken for bacteria (FIG. 16A) at 3rd day and for fungi (FIG. 16B) and *Phytophthora* (FIG. 16C) at 28th day except for *B. cinera, C. acutatum,* and *C. gloeosporioides,* which were at 7th day after setup of the assays.
Figure 16B:
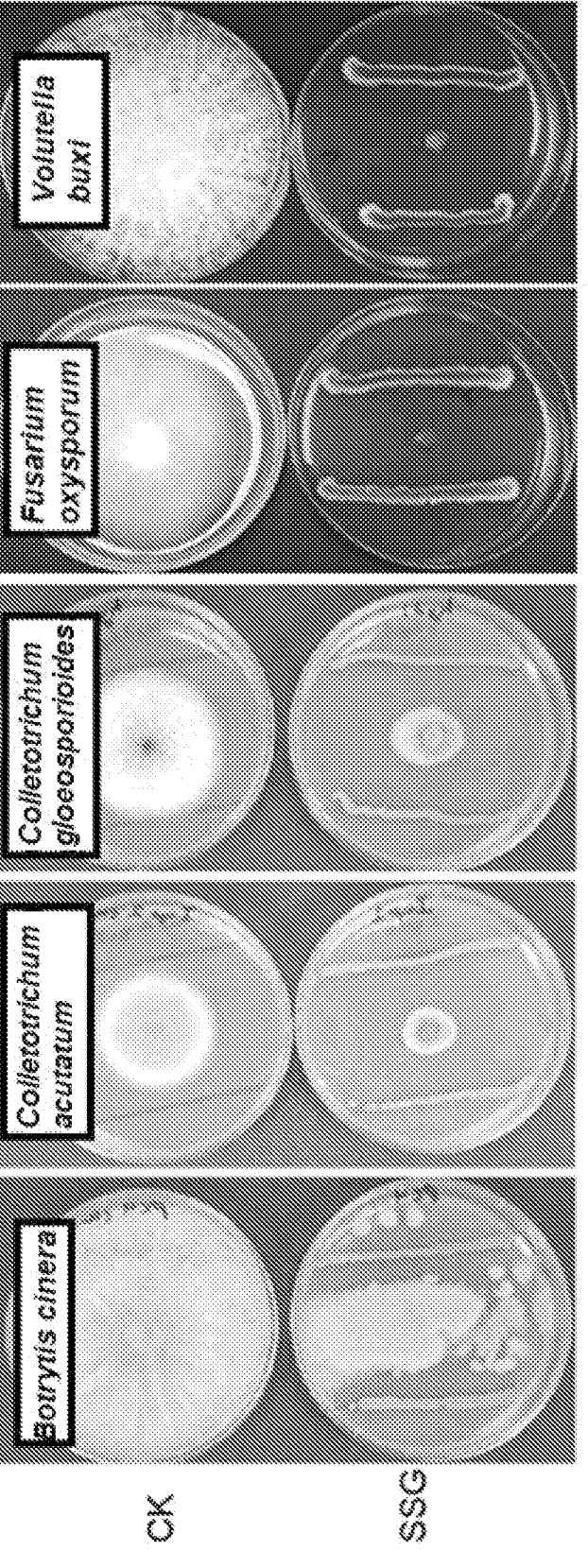
Figure 16C:
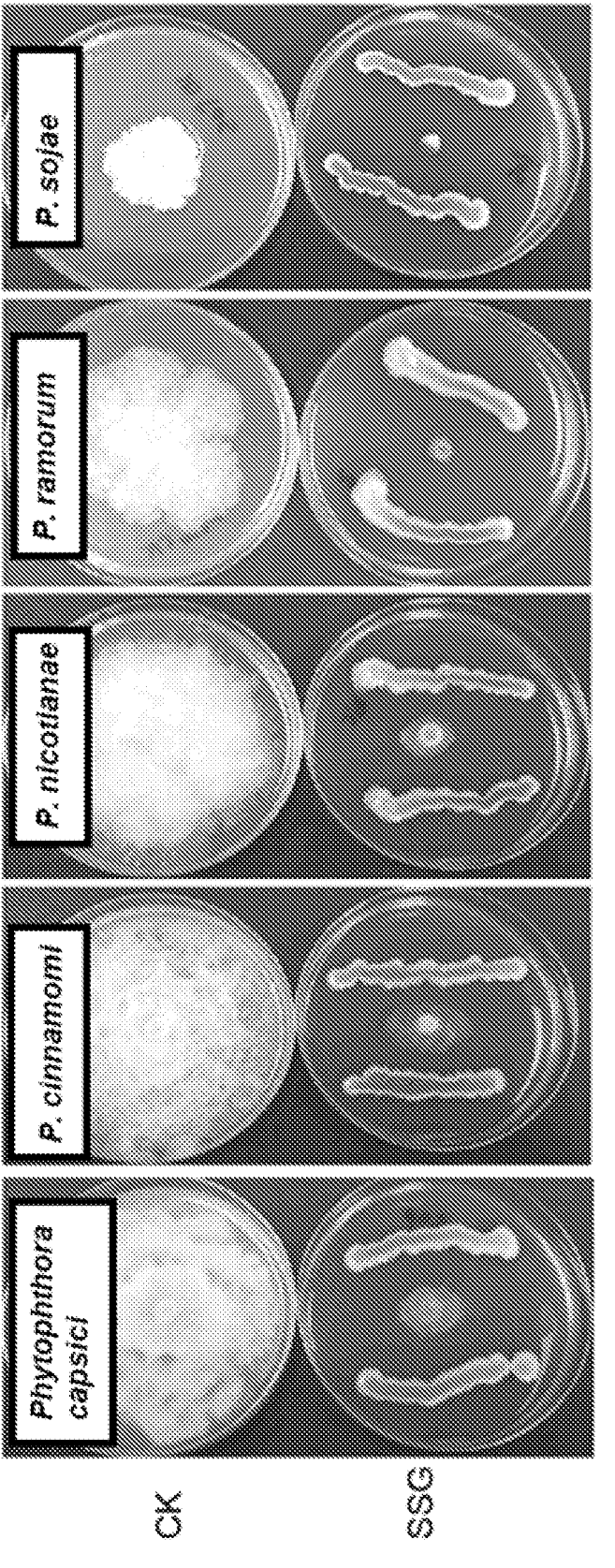

Between filamentous fungi and *Phytophthora*, stronger suppression was observed on *Phytophthora* than on fungi (FIG. 16). Among tested *Phytophthora*, the growth of *P. infestans* and *P. ramorum* was reduced by more than 90%. The growth of the rest was reduced by at least 75% compared to the control. For fungi, suppression rates were lower, between 54 to 88% (Table 6).

TABLE 6

Plant Disease Suppression by SSG

| Phytopathosystem | Treatment | Disease Severity (1-10 scale)[x] | | | | | | | | | |
|---|---|---|---|---|---|---|---|---|---|---|---|
| | | 1dbi | | 1wbi | | 2wbi | | 4wbi | | 3dai | |
| | | Mean | SE | Mean | SE | Mean | SE | Mean | SE | Mean | SE |
| Fraser fir | SSG | 2 | 1.4 | 3.2 | 0.8 | 1.8 | 1.0 | 2.8 | 1.5 | 2.5 | 1.3 |
| *P. cinnamomi* | CK | 3.7 | 1.8 | 2.5 | 0.7 | 2.3 | 1.2 | 2.8 | 1.2 | 3.1 | 1.2 |
| (28D5, 28E3, 28E6 mix) | P value (n = 4)[y] | *0.005* | | 0.26 | | *0.5* | | 1 | | *0.49* | |
| | Reduction (%)[z] | 45.9 | | −28 | | 21.7 | | 0 | | 19.4 | |
| Petunia | SSG | 1.5 | 1.3 | 1.7 | 1.9 | 1.7 | 1.1 | 7 | 1.5 | 5.2 | 1.7 |
| *P. nicotianae* | CK | 1 | 0.9 | 0 | 0.0 | 6.7 | 1.2 | 4.7 | 1.7 | 3.8 | 2.4 |
| (30J5, 31A3 mix) | P value (n = 3) | 0.74 | | 0.3 | | 0.007 | | 0.23 | | 0.59 | |
| | Reduction (%) | −50 | | 100 | | 74.6 | | −48.9 | | −36.8 | |
| Rhododendron | SSG | 1.8 | 0.2 | 2.3 | 0.1 | 5.3 | 0.3 | NA | NA | NA | NA |
| *P. ramorum* | CK | 3.9 | 0.3 | 5.3 | 0.3 | 7.3 | 0.3 | NA | NA | NA | NA |
| | P value (n = 9) | 0.0002 | | 0.033 | | 0.101 | | | | | |
| | Reduction (%) | 53.9 | | 56.6 | | 27.4 | | | | | |
| Annual vinca | SSG | 0.3 | 0.1 | NA | NA | NA | NA | NA | NA | NA | NA |
| *P. nicotianae* | CK | 6.3 | 0.7 | NA | NA | NA | NA | NA | NA | NA | NA |
| | P value (n = 9) | <0.0001 | | | | | | | | | |
| | Reduction (%) | 95.2 | | | | | | | | | |
| Bell pepper | SSG | 3.9 | 0.9 | NA | NA | NA | NA | NA | NA | NA | NA |
| *P. capsici* | CK | 8.9 | 0.6 | NA | NA | NA | NA | NA | NA | NA | NA |
| | P value (n = 9) | 0.0016 | | | | | | | | | |
| | Reduction (%) | 56.2 | | | | | | | | | |
| Hydrangea | SSG | 0.8 | 0.1 | 0.8 | 0.1 | 0.8 | 0.1 | 1.3 | 0.3 | 1 | 0.0 |
| *C. gleosporiodes* | CK | 2.4 | 0.4 | 2.3 | 0.3 | 1.4 | 0.1 | 2.3 | 0.3 | 1.4 | 0.1 |
| | P value (n = 9) | <0.0001 | | 0.001 | | 0.012 | | 0.08 | | 0.04 | |
| | Reduction (%) | 66.7 | | 65.2 | | 42.9 | | 43.5 | | 28.6 | |
| Pansy | SSG | 3.9 | 0.8 | NA | NA | 5.3 | 0.4 | NA | NA | 3.7 | 0.6 |
| *C. fruticola* | CK | 5.6 | 0.8 | NA | NA | 7.7 | 0.7 | NA | NA | 5.5 | 1.0 |
| | P value (n = 6) | 0.23 | | | | 0.041 | | | | 0.1 | |
| | Reduction (%) | 30.4 | | | | 31.2 | | | | 32.7 | |
| Pansy | SSG | 2.9 | 0.7 | NA | NA | NA | NA | NA | NA | NA | NA |
| *A. tenuissium* | CK | 7.3 | 0.8 | NA | NA | NA | NA | NA | NA | NA | NA |
| | P value (n = 9) | 0.002 | | | | | | | | | |
| | Reduction (%) | 60.3 | | | | | | | | | |
| Petunia | SSG | 6.3 | 0.5 | 1.4 | 0.2 | 5 | 0.4 | 5 | 0.7 | 4.9 | 0.3 |
| *B. cinerea* | CK | 7.9 | 0.6 | 4.2 | 0.3 | 7.4 | 0.7 | 7.9 | 0.5 | 8 | 0.3 |
| | P value (n = 9) | 0.07 | | <0.0001 | | *0.001* | | <0.0001 | | 0.02 | |
| | Reduction (%) | 20.3 | | 66.7 | | 32.4 | | 36.7 | | 38.8 | |
| Boxwood | SSG | 1.9 | 0.2 | NA | NA | NA | NA | NA | NA | NA | NA |
| *V. buxi* | CK | 3.4 | 0.4 | NA | NA | NA | NA | NA | NA | NA | NA |
| | P value (n = 9) | 0.014 | | | | | | | | | |
| | Reduction (%) | 44.1 | | | | | | | | | |
| Geranium | SSG | 1.4 | 0.1 | 1.6 | 0.1 | NA | NA | NA | NA | 1.7 | 0.1 |
| *X. campastris* | CK | 3.3 | 0.2 | 2.7 | 0.2 | NA | NA | NA | NA | 3.8 | 0.3 |
| | P value (n = 9) | 0.0002 | | 0.004 | | | | | | <0.0001 | |
| | Reduction (%) | 57.6 | | 40.7 | | | | | | 55.3 | |
| Impatiens | SSG | 2.6 | 0.3 | 3 | 0.1 | 1.9 | 0.2 | 4.2 | 0.0 | NA | NA |
| TWSV | CK | 3.2 | 0.2 | 4.1 | 0.3 | 4 | 0.3 | 3.2 | 0.0 | NA | NA |
| | P value (n = 9) | *0.003* | | 0.01 | | *<0.0001* | | 0.02 | | | |
| | Reduction (%) | 23.5 | | 26.8 | | 52.5 | | −31.3 | | | |

[x]Disease severity with a 1-10 scale: 1 = 1-10%, 2 = 11-20% up to 10 = 91-100% infection of plants or plant parts. 1dbi, 1wbi, 2wbi, and 4wbi represent treatments at 1 day and 1, 2, and 4 weeks before inoculation with a pathogen, respectively. 3dai represents a treatment at 3 days after inoculation with a pathogen.
[y]P results from two-factor ANOVA with replication at $\alpha = 0.05$. "n" is replicate plant pots from repeated experiments. Underlined numbers indicate a significant difference between CK and SSG. Italicized numbers indicate significant differences among experiments. Reduction is calculated using (CK-SSG)/CK × 100.
[z]NA = data is not available.

Specifically, fast-growing species such as *Botrytis cinerea* were less affected compared to slow-growing species.

Bacterial suppression by SSG depended on species. Suppression halo zones that were larger than 1.5 cm in diameter were observed for three species, *X. campestris*, *P. syringae*, and *S. maltophilia* (Table 5). SSG also strongly suppressed *E. coli* although the suppression was not as strong as for *X. campestris* and *P. syringae* (FIG. 16). However, it did not suppress *E. carotovora* and suppression of *R. solanacearum* was weak (Table 5).

Figure 5:
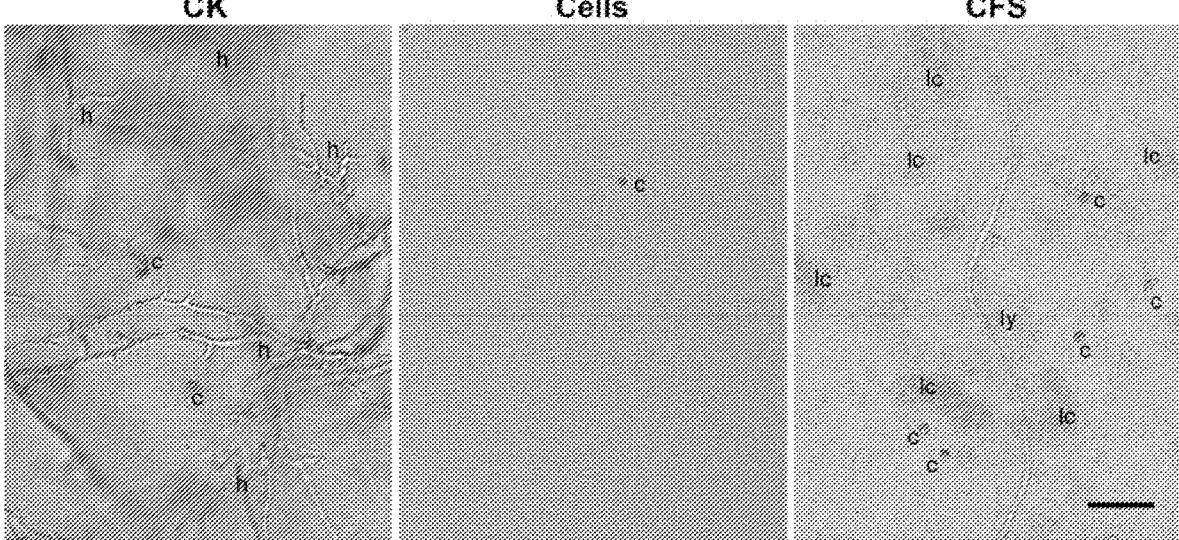
FIG. 5 shows effects of SSG on germination and survival of *P. capsici* zoospores at $10^4$/mL. Left: Zoospores in potato dextrose broth (PDB) without SSG (CK). Bar=50 μm. Center: Zoospores in cell-free suspension (CFS). Right. Zoospores in SSG cells resuspended in PDB. Micrographs were taken 24 h after incubation. c=conidium, ly=lysing conidium, lc=lysed conidium, h=hyphae.

The effects of SSG on culture growth of bacterial, fungal and oomycete pathogens indicate that SSG is a broad-spectrum antagonist. This conclusion is consistent with SSG great genomic capacity for antibiotic production estimated by genome sequencing. SSG contains not only synthase cluster of pyrrolnitrin, an antibiotic for fungi and strepto- mycetes and gram positive bacteria, but also gene clusters for bacteriocin production, polyketide synthase (PKS) and nonribosomal peptide synthetase (NRPS). The latter has been linked with synthesis of occidiofungins or burkholdi- nes, a new antibiotic effective against fungal pathogens and *Pythium*, a relative of *Phytophthora*. Activities of SSG in dual culture assays suggests that SSG is capable to produce such antibiotics and other beyond through diffusing in agar which can effectively inhibit growth of fungal, oomycete and some bacterial pathogens. Despite that SSG may pro- duce bacteriocin that may contribute to inhibition of five out of six test bacterial pathogens, it may not produce kasug- ammycin (kasumin), an effective bactericide for *Erwinia* sp due to the fact that *E. carotovora* was not suppressed in the dual culture assay. Efficacy of SSG on Gram positive bacterial pathogens remained unknown despite the fact that SSG can produce pyrrolnitrin effective on these pathogens.
Zoospore Lysis and Germination Inhibition As an important *Phytophthora* pathogen and large zoo- spore producer, P. capcisi was used for zoospore germination test. Almost all zoospores lysed 24 h after incubation with resuspended SSG cells while the control without SSG cells did not (FIG. 5). To determine whether the suppression was resulted from antibiotics produced, zoospores were also incubated with cell free supernatant of the SSG culture (CFS). Poor gemination of the zoospores as for treatment with SSG cell suspension was observed. However, in CFS treatment there were many fewer lysed cysts compared to that in SSG cells (FIG. 5), indicating that metabolites of SSG suppressed mainly germination but not lysis of zoospores. *P. capsici* zoospore lysis by *B. cepacia* metabolites has been reported previously. In that study, up to 10% zoospore lysis was observed within a one-hour time course which was significantly lower compared to a *Pseudomonas* isolate used. It is not clear whether SSG CFS may result in a different rate in the same time frame.

Similar effects of SSG have also been observed in spore lysis and germination of fungal boxwood blight pathogen Cps. Oomycetes and fungi are different in cell wall compo- sition. The former is composed of chitin, while the latter is made up of a mix of cellulosic compounds and glycan. To degrade cell wall degradation of these microorganisms, SSG must be a strong producer of lytic enzymes. Chitinase, $\beta \rightarrow 1,3$-glucanase, and proteases are common lytic enzymes found in bacterial and fungal biocontrol agents. Except for chitinase and $\beta \rightarrow 1,3$-glucanase, 58 genes encoding various proteases and five genes for biosynthesis of a-glucosidases and B-glucosidases that involve in cellulose degradation are present in the SSG genome. This suggests that SSG may use unusual mechanisms to lyse spores of fungi and *Phytoph- thora*.
Control of Plant Diseases by SSG SSG was evaluated in 12 phytophathosystems involving ornamental plants and their pathogens, including bacteria, fungi, oomycetes and a virus. Up to five treatment times before and after plants were inoculated with a pathogen were investigated. SSG gave a disease control efficacy varied from phytopathosystems, pathogen types, and treatment intervals (Table 6). The highest efficacy was in *vinca— Phytophthora nicotianae*. Spraying plants with SSG cell suspension at one day before pathogen inoculation (1dbi) resulted in 95% disease reduction. The same treatment also resulted in more than 50% disease reduction in other five systems, *rhododendron —P. ramorum*, pepper—P. capcisi, pansy—*Alternaria* tenuissium, *hydrangea*—Collectortri- chum gleosporiodes, and geranium—*Xanthomonas camp- estris*. Similar efficacy was also observed for treatments with an expanded interval, one week before inoculation (1wbi), in *rhododendron—P. ramorum* and *hydrangea*—C. gleospori- odes. However, decreased efficacies were observed at 2-4 wbi. For *rhododendron—P. ramorum*, the efficacy was 30% lower and for *hydrangea*—Collectortrichum gleosporiodes, it was 20% lower. Performances of SSG in these systems are similar to that observed in boxwood-Cps, which suggests that SSG may use mechanisms mediated by direct antago- nism or mixed-path antagonism. Plants treated with SSG and nutrient broth (CK) are shown in FIGS. 7A-7D.

Figure 7A:
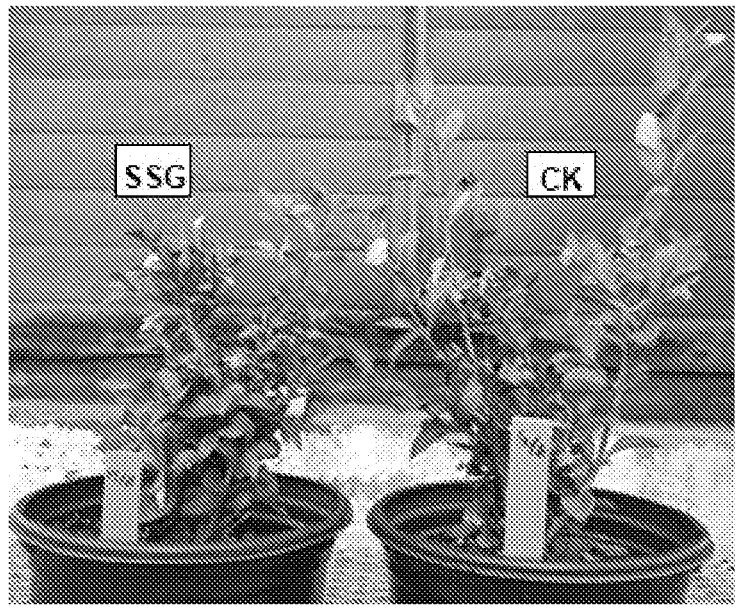
FIGS. 7A-7D show plant disease suppression with a SSG cell suspension applied on foliage one day before inoculation with a pathogen in comparison with the control (CK, nutrient broth).
Figure 7B:
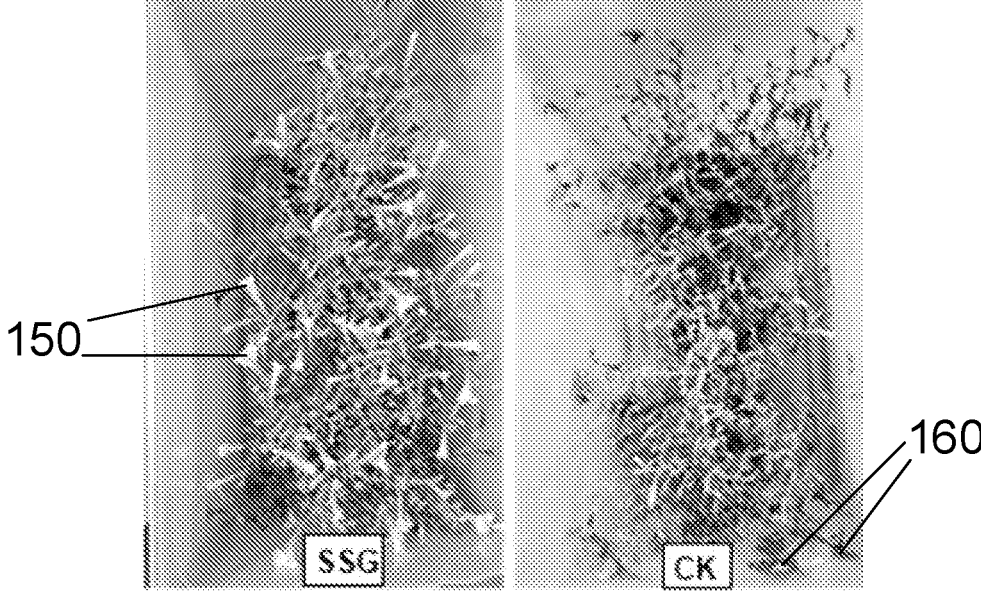

SSG may also use other mechanisms for plant protection in other phytopathosystems. In *petunia—Botrytis cinerea*, best efficacy did not occur in treatments at 1bdi but did in the treatment at 1wdi. Even treatments at 2 wbi and 4 wbi were more effective than that at 1dbi. This pattern is similar to that found with fungal biocontrol agent *Trichoderma koningiop- sis* for boxwood blight, which was more effective for treat- ments with great intervals, suggesting that disease suppres- sion may result from indirect antagonism of the biocontrol agent through competition and induction of host resistance or the Induced Systemic Resistance (ISR). In pansy—*C. fruticola*, SSG gave very similar protection for treatments at 1 dbi, 1 wbi and 2 wbi (Table 6) which may also be attributed to the same antagonism mechanism. In fact, SSG is a great producer of siderophores, indicating its ability of Fe defi- ciency response reduction and Fe acquisition improvement, which is an important feature of ISR eliciting microbes. With reference to FIG. 7B, SSG-treated *petunia* showed larger, healthier flowers 150 compared to nutrient broth- treated plants, which had numerous dead/browned parts 160.

Figure 7C:
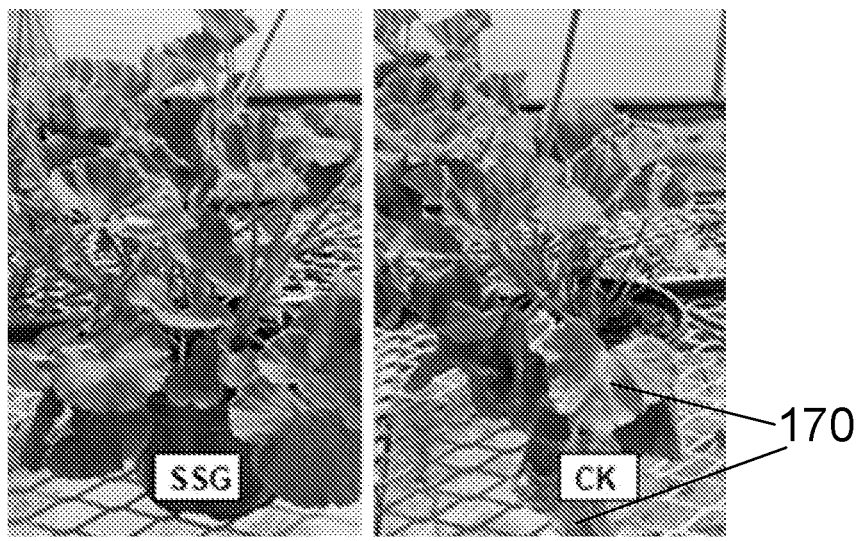

Post treatment with SSG was not as effective as pre- treatment in the phytopathosystems investigated. Among the evaluated six systems, the best result was found in gera- nium—*Xanthomonas campestris* (Table 6). With reference to FIG. 7C, the treatment at three days after plants inocu- lation with the pathogen (3 dai) resulted in 55% reduction of geranium blight 170, a rate similar to the pretreatment at 1 dbi and 1wdi. However, in other five systems, SSG was not effective or at a very low level. This difference in different phytopathosystems seems associated with pathogen type. SSG potently suppressed spore germination (FIG. 5) but was less effective on mycelia, particularly those fast-growing filamentous fungi and *Phytophthora* (Table 5). In contrast, SSG can directly suppress the bacterial pathogen given that it shares features of bacteria that do not differentiate in cell growth and enter plant tissue through natural openings or wounds. Therefore, SSG may be used as not only a protec- tive but also a curative biocontrol agent for diseases caused by bacterial pathogens it suppresses.

Figure 7D:
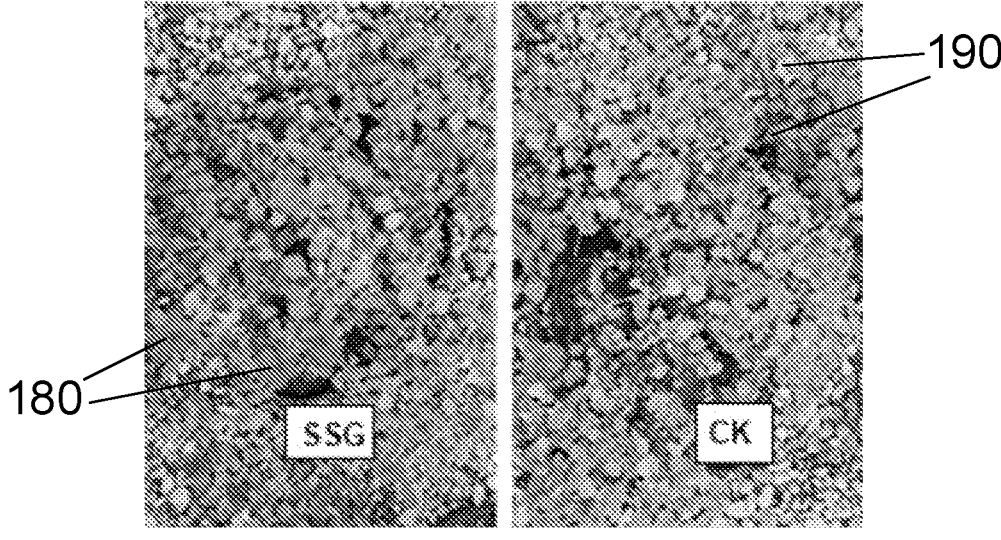

There was great variation in results for treatments in *impatiens*-TWSV and two root disease systems. In *impa- tiens*-TWSV, treatment at 2 wbi other than two other treat- ments at short lead times resulted in 53% control of TWSV (Table 6). Furthermore, treatment at 4 wbi brought a nega- tive result and significant variations among the replicates. With reference to FIG. 7D, SSG-treated plants displayed healthy flowers 180, while nutrient broth-treated plants displayed smaller, wilted flowers 190. In Fraser fir—*P. cinnamomi*, SSG treatment at 1 dbi resulted in a significant reduction of plants root rot by 46% compared to the control, although experimental differences of treatments were also significant. In addition, treatments at other lead times and 3 dai showed results that were either not significantly different from the control or presented significant differences among replicates. In *petunia—P. nicotianae*, there was as high as 75% reduction for treatment at 2 wbi but negative results for other treatments, although the results had no significant differences with the control because of experimental variations. The cause of these variations is not clear. However, many factors could involve. SSG as root inoculant may not be as efficient as it used as foliage inoculant since it is a foliage endophyte despite its survival in pine bark dominant potting mix. Moreover, our knowledge of SSG ecology and its interaction with plants is yet limited.

Factors such as overhead irrigation and rain full events after plant treatments that may affect minimal concentration for activities of SSG and methods used for pathogen inoculation, which may result in consistent plant infection are warranted to be further investigated.

In summary, SSG is a promising biocontrol agent for a variety of plant diseases. SSG was effective not only for fungal and *Phytophthora* diseases but also bacterial, and viral diseases although control efficacy for some of the diseases was low. This spectrum of antagonism, including viral disease, has not been reported for any biocontrol agents documented. The broad antagonism spectrum of SSG may be attributed to its ability to biosynthesize antibiotics, lytic enzymes and insecticidal products, physical and chemical interference and competition with pathogens or ISR induction. However, further studies on its ecology, interaction with plants and its risk to human health is warranted for the application of SSG in the field.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Anonymous. Chlorothalonil Fungicide Banned in European Union. 2019. Available online: <vegetablegrowers-news.com/news/chlorothalonil-fungicide-banned-in-european-union/> accessed Feb. 22, 2020).
2. Aziz, R. K., et al, (2008) The RAST Server: rapid annotations using subsystems technology. BMC Genomics 9, 75-75.
3. Baldwin, A. et al. (2005) Multilocus sequence typing scheme that provides both species and strain differentiation for the *Burkholderia cepacia* complex. J Clin Microbiol 43, 4665-4673.
4. Batdorf, L. R. Boxwood Handbook—A Practical Guide to Knowing and Growing Boxwood, 3rd ed.; The American Boxwood Society: Boyce, VA, USA, 2005; p. 123.
5 Batista, B. D., et al. (2018) Screening of tropically derived, multi-trait plant growth-promoting rhizobacteria and evaluation of corn and soybean colonization ability. Microbiol Res 206, 33-42.
6. Baudoin, A.; et al. Evaluation of fungicides for control of boxwood blight, 2014. Plant Dis. Manag. Rep. 2015, 9, OT006.
7. Benková, E., et al. (2003) Local, efflux-dependent auxin gradients as a common module for plant organ formation. Cell 115, 591-602.

8. Bevivino, A., et al, 1994. Phenotypic comparison between rhizosphere and clinical isolates of *Burkholderia cepacia*. Microbiology 140, 1069-1077.
9. Bevivino, A., et al. (1998) Characterization of a free-living maize-rhizosphere population of *Burkholderia cepacia*: effect of seed treatment on disease suppression and growth promotion of maize. FEMS Microbiol Ecol 27, 225-237.
10. Blin, K., et al, (2019) antiSMASH 5.0: updates to the secondary metabolite genome mining pipeline. Nucleic Acids Res. 47, W81-W87.
11. Bunt, C. R.; et al. Coated solid substrate microbe formulations: *Pseudomonas* spp. and zeolite. In Microbial-Based Biopesticides: Methods and Protocoles, Methods in Molecular Biology; Glare, T. R., et al, Eds.; Humana Press: New York, NY, USA, 2016; Volume 1477, pp. 49-57.
12. Calabro, J. M. (2018). Reclaiming boxwood from boxwood blight, Nursery Management, <www.nurserymag-.com/article/reclaiming-boxwood-from-blight-calabro/#>, accessed Feb. 8, 2021.
13. Campbell, E., et al, (1997) A polyketide-synthase-like gene is involved in the synthesis of heterocyst glycolipids in *Nostoc punctiforme* strain ATCC 29133. Arch. Microbiol. 167, 251-258.
14. Choi, J., et al, 2013. Fungal plant cell wall-degrading enzyme database: a platform for comparative and evolutionary genomics in fungi and Oomycetes. BMC Genomics 14 Suppl 5, S7-S7.
15. Choudhary, B., et al, 2014. Fungal cell-wall lytic enzymes, antifungal metabolite(s) production, and characterization from *Streptomyces exfoliatus* MT9 for controlling fruit-rotting fungi. Journal of Basic Microbiology 54, 1295-1309.
16. Cinquerrui, A.; et al. Integrated management for the reduction of *Calonectria* infections in ornamental nurseries. Plant Dis. 2017, 101, 165-169.
17. Coenye, T., et al, (2003) Diversity and significance of *Burkholderia* species occupying diverse ecological niches. 5, 719-729.
18. Compant, S., et al, (2008) Diversity and occurrence of *Burkholderia* spp. in the natural environment. FEMS Microbiol. Rev. 32, 607-626.
19. Compant, S., et al. (2005) Use of plant growth-promoting bacteria for biocontrol of plant diseases: Principles, mechanisms of action, and future prospects. Appl Environ Microbiol 71, 4951-4959.
20. Crennell, S. J., et al, (2000) The predicted structure of photopexin from *Photorhabdus* shows the first haemopexin-like motif in prokaryotes. FEMS Microbiol. Lett. 191, 139-144.
21. Crepel, C., et al. (2003) First report of blight on *Buxus* spp. caused by *Cylindrocladium buxicola* in Belgium. Plant Disease 87:1539.
22. Daughtrey, M. L. Boxwood blight: Threat to ornamentals. Annu. Rev. Phytopathol. 2019, 57, 189-209.
23. De Smet, B., et al, 2015. *Burkholderia stagnalis* sp. nov. and *Burkholderia territorii* sp. nov., two novel *Burkholderia cepacia* complex species from environmental and human sources. Journal of Systematic and Evolutionary Microbiology 65, 2265-2271.
24. Depoorter, E., et al. (2016) *Burkholderia*: an update on taxonomy and biotechnological potential as antibiotic producers. Applied Microbiology and Biotechnology 100: 5215-5229.
25. Diaz Herrera, S., et al. (2016) Wheat seeds harbour bacterial endophytes with potential as plant growth pro-

53 moters and biocontrol agents of Fusarium *graminearum*. Microbiological Research 186-187:37-43.

26. el-Banna, N., et al, 1998. Pyrrolnitrin from *Burkholderia cepacia*: antibiotic activity against fungi and novel activities against streptomycetes. Journal of Applied Microbiology 85, 69-78.

27. Eljounaidi, K.; et al. Bacterial endophytes as potential biocontrol agents of vascular wilt diseases—Review and future prospects. Biol. Control 2016, 103, 62-68.

28. Elmhirst, J. F., et al. (2013) First report of box blight caused by *Cylindrocladium pseudonaviculatum* (*C. buxicola*) in British Columbia, Canada. Plant Disease 97:559.

29 Estrada-De Los Santos, P., et al. (2001) *Burkholderia*, a genus rich in plant-associated nitrogen fixers with wide environmental and geographic distribution. Appl Environ Microbiol 67, 2790.

30. Fan, Q., et al, (2005) Clustered genes required for synthesis and deposition of envelope glycolipids in *Anabaena* sp. strain PCC 7120. Mol. Microbiol. 58, 227-243.

31. Ganci, M. L. et al. Susceptibility of commercial boxwood cultivars to *Cylindrocladium buxicola*, the causal agent of box blight (ABstr.). Phytopathology 2013, 103, 47.

32. Ganci, M. L. Investigation of Host Resistance in *Buxus* Species to the Fungal Plant Pathogen *Calonectria pseudonaviculata* (=*Cylindrocladium buxicola*), the Causal Agent of Boxwood Blight and Determination of Overwinter Pathogen Survival. Master's Thesis, North Carolina State University, Raleigh, NC, USA, 2014.

33. Gehesquière, B. *Cylindrocladium buxicola* (syn. *Calonectria pseudonaviculata*) on *Buxus*: Molecular Characterization, Epidemiology, Host Resistance and Fungicide Control. Ph.D. Thesis, Ghent University, Ghent, Belgium, 2014.

34. Germida, J. J. et al. (1996) Plant growth-promoting rhizobacteria alter rooting patterns and arbuscular mycorrhizal fungi colonization of field-grown spring wheat. Biol Fertility Soils 23, 113-120.

35 Ghosh, R., et al. (2016) Role of phosphate solubilizing *Burkholderia* spp. for successful colonization and growth promotion of *Lycopodium* cemuum L. (Lycopodiaceae) in lateritic belt of Birbhum district of West Bengal, India. Microbio/Res 183:80-91.

36. Gillis, M., et al. (1995) Polyphasic taxonomy in the genus *burkholderia* leading to an emended description of the genus and proposition of *Burkholderia Vietnamiensis* sp. Nov. for N2-fixing isolates from rice in Vietnam. Int J Syst Evol Microbiol 45, 274-289.

37. Gilson, D. et al, (2018) Boxwood blight found in Wisconsin for the first time. <datcp.wi.gov/Pages/News_Media/BoxwoodBlightFound.aspx> accessed Feb. 8, 2021.

38. Glick, B. R. (2012) Plant growth-promoting bacteria: Mechanisms and applications Scientifica 2012, 15.

39. Glick, B. R. (2014) Bacteria with ACC deaminase can promote plant growth and help to feed the world. Microbiological Research 169:30-39.

40. Gonzalez, C. F.; et al. Bacteriocin, plasmid and pectolytic diversity in Pseudommnas *cepacia* of clinical and plant origin. J. Gen. Microbiol. 1979, 110, 161-170.

41. Gonzalez, C. F.; et al. Mobilization, cloning, and sequence determination of a plasmid-encoded polygalacturonase from a phytopathogenic *Burkholderia* (*Pseudomonas*) *cepacia*. Mol. Plant-Microbe Interact. 1997, 10, 840-851.

42. Gorgiladze, Z., et al. (2011) First report of box blight caused by Cylindrocladiumbuxicola in Georgia. New Disease Reports 23:24.

43. Ha, J. K., et al, (2019) Application of the whole genome-based bacterial identification system, TrueBac ID, using clinical isolates that were not identified with three matrix-assisted laser desorption/ionization time-of-flight mass spectrometry (maldi-tof ms) systems. Annals of laboratory medicine 39, 530-536.

44. Hardoim, P. R., et al, (2008) Properties of bacterial endophytes and their proposed role in plant growth. Trends Microbiol. 16, 463-471.

45. Healy, S. E. Biology and Management of Box Blight Caused by *Cylindrocladium buxicola*. Master's Thesis, The University of Guelph, Toronto, ON, Canada, 2014.

46. Henricot, B. Box blight rampages onwards. Plantsman 2006, 5, 153-157.

47. Henricot, B. et al. Evaluation of foliar fungicide sprays for the control of boxwood blight, caused by the fungus *Cylindrocladium buxicola*. Plant Health Progr. 2013.

48. Henricot, B., et al, (2008) Studies on the control of *Cylindrocladium buxicola* using fungicides and host resistance. Plant Disease 92:1273-1279.

49. Henricot, B., et al. (2000) A new blight disease on *Buxus* in the UK caused by the fungus Cylindroladium. Plant Pathology 49:805.

50. Henricot, B.; et al. Studies on the control of *Cylindrocladium buxicola* using fungicides and host resistance. Plant Dis. 2008, 92, 1273-1279.

51. Henry, D. A.; et al. Identification of *Burkholderia cepacia* isolates from patients with cystic fibrosis and use of a simple new selective medium. J. Clin. Microbiol. 1997, 35, 614-619.

52. Hoffman, B. M., et al, (2014) Mechanism of nitrogen fixation by nitrogenase: the next stage. Chem. Rev. 114, 4041-4062.

53. Hong, C. X. Fighting plant pathogens together. Science 2019, 365, 229.

54. Hong, C. X. Saving American gardens from boxwood blight. Boxwood Bull. J. Am. Boxwood Soc. 2019, 58, 4-10.

55. Hwang, J., et al. (2002) Pyrrolnitrin production by *Burkholderia cepacia* and biocontrol of *Rhizoctonia* stem rot of poinsettia. Biological Control 25:56-63.

56. Ivors, K. L.; et al. Evaluation of fungicides for the prevention of boxwood blight, 2012. Plant Dis. Manag. Rep. 2013, 7, OT014.

57. Ivots, K. L., et al. (2012) First report of boxwood blight caused by *Cylindrocladium pseudonaviculatum* in the United States. Plant Disease 96:1070.

58. Jeng, W.-Y., etal, 2011. Structural and functional analysis of three B-glucosidases from bacterium *Clostridium cellulovorans*, fungus *Trichoderma reesei* and termite *Neotermes koshunensis*. Journal of Structural Biology 173, 46-56.

59. Joy, A. E. et al. (1994) Biocontrol of *Alternaria* leaf blight on American *ginseng* by *Burkholderia cepacia* AMMD. In The Challenge of the 21st Century Proc Inc *Ginseng* Conf eds. Bailey, W. G., et al. pp. 93-100. Vancouver, BC: Simon Fraser University.

60. Junaid, J. M., et al, 2013. Commercial biocontrol agents and their mechanism of action in the management of plant pathogens. International Journal of Modern Plant and Animal Sciences 1, 39-57.

61. Khan, M. S., et al. (2007) Role of phosphate-solubilizing microorganisms in sustainable agriculture—A review. Agronomy for Sustainable Development 27, 29-43.

62. Khatun, A., et al, 2018. *Pseudomonas* and *Burkholderia* inhibit growth and asexual development of *Phytophthora capsici*. Zeitschrift für Naturforschung 73 (3-4) c: 123-135.

63. Kong, P. et al. (2019) Utilization of plant endophytes for control of boxwood blight. Proc South Nurs Assoc Res Conf 63, 115-117.

64. Kong, P., 2019. Evaluation of a novel endophytic *Pseudomonas lactis* strain for control of boxwood blight. Journal of Environmental Horticulture 37, 39-43.

65. Kong, P., et al, (2017) Biocontrol of boxwood blight by *Trichoderma koningiopsis* Mb2. Crop Protect. 98, 124-127.

66. Kong, P., et al, (2020) A potent *Burkholderia* endophyte against boxwood blight caused by *Calonectria pseudonaviculata*. Microorganisms 8 (2), 310.

67. Kong, P., et al, 2010. Zoospore density dependent behaviors of *Phytophthora nicotianae* are autoregulated by extracellular products. Phytopathology 100, 632-637.

68. Kong, P., et al, 2010. Zoospore interspecific signaling promotes plant infection by *Phytophthora*. BMC Microbiology 10: e313. Published online.

69. Kong, P., et al, 2012. Effect of electrical conductivity on survival of *Phytophthora alni, P. kernoviae* and *P. ramorum* in a simulated aquatic environment Plant Pathology 61:1179-1186.

70. Kong, P., et al, 2020. Characterization of boxwood endophytic *Burkholderia cepacia* SSG as a plant growth promoter Letters in Applied Microbiology Under review.

71. Kong, P., et al, 2020. Complete genome sequence of a boxwood endophyte *Burkholderia* cepacian SSG with broad biotechnological application potential. Biotechnology Reports Under review.

72 Kong, P., et al. (2016) First report of blight of *Sarcococca hookeriana* var. *humilis* by *Calonectria pseudonaviculata* in Virginia. Plant Disease 100:247.

73. Kong, P., et al. (2017) First report of *Pachysandra terminalis* leaf spots by *Calonectria pseudonaviculata* in Virginia. Plant Disease 101:509.

74. Kong, P., et al. (2019) Variation in infection of boxwood, pachysandra and sweetbox by *Calonectria pseudonaviculata*. Planta, 249:831-838.

75. Kong, P.; et al. Host responses and impact on the boxwood blight pathogen, *Calonectria pseudonaviculata*. Planta 2019, 249, 831-838.

76. Koren, S., et al, (2017) Canu: scalable and accurate long-read assembly via adaptive k-mer weighting and repeat separation. 27, 722-736.

77. LaMondia, J. A. Management of *Calonectria pseudonaviculata* in boxwood with fungicides and less susceptible host species and varieties. Plant Dis. 2015, 99, 363-369.

78. LaMondia, J. A. *Pachysandra* species and cultivar susceptibility to the boxwood blight pathogen, *Calonectria pseudonaviculata*. Plant Health Progr. 2017, 18:41-43.

79. LaMondia, J. A.; et al Susceptibility of boxwood accessions from the National Boxwood Collection to boxwood blight and the potential for differences between *Calonectria pseudonaviculata* and *C. henricotiae*. HortScience 2017, 52, 873-879.

80. LaMondia, J. A.; et al. *Calonectria pseudonaviculata* can cause leaf spot and stem blight of *Pachysandra procumbens*. Plant Health Progr. 2013.

81. LaMondia, J. A.; et al. First report of *Cylindrocladium pseudonaviculatum* causing leaf spot of *Pachysandra terminalis*. Plant Dis. 2012, 96, 1069.

82. LeBlanc, N., et al, (2018) Boxwood blight: an ongoing threat to ornamental and native boxwood. Applied Microbiology and Biotechnology 102:4371-4380.

83. Liaqat, F. et al. (2016) Identification and characterization of endophytic bacteria isolated from in vitro cultures of peach and pear rootstocks. 3 Biotech 6, 120-120.

84. Likins, T. M., et al. (2019) Preventing soil inoculum of *Calonectria pseudonaviculata* from splashing onto healthy boxwood foliage by mulching. Plant Disease, 103:357-363.

85. Lu, S.-E., et al, 2009. Occidiofungin, a unique antifungal glycopeptide produced by a strain of *Burkholderia contaminans*. Biochemistry 48, 8312-8321.

86. Ludwig-Müller, J. (2011) Auxin conjugates: their role for plant development and in the evolution of land plants. J Exp Bot 62, 1757-1773.

87. Mahenthiralingam, E., et al, (2005) The multifarious, multireplicon *Burkholderia cepacia* complex. Nature Reviews Microbiology 3, 144-156.

88. Mahenthiralingam, E., et al, 1997. Identification and characterization of a novel DNA marker associated with epidemic *Burkholderia cepacia* strains recovered from patients with cystic fibrosis. Journal of Clinical Microbiology 35, 808-816.

89. Mahenthiralingam, E., et al, 2000. DNA-based diagnostic approaches for identification of *Burkholderia cepacia* complex, *Burkholderia vietnamiensis, Burkholderia multivorans, Burkholderia stabilis, Burkholderia cepacia* genomovars I and III. Journal of Clinical Microbiology 38, 3165-3173.

90. Malapi-Wight, M.; et al. *Sarcococca* blight: Use of whole-genome sequencing for fungal plant disease diagnosis. Plant Dis. 2016, 100, 1093-1100.

91. Mendes, R., et al. (2007) Diversity of cultivated endophytic bacteria from sugarcane: Genetic and biochemical characterization of *Burkholderia* cepacian complex isolates. Appl Environ Microbiol 73, 7259-7267.

92. Michiels, J., et al, (1998) The *Rhizobium etli* rpoN locus: DNA sequence analysis and phenotypical characterization of rpoN, ptsN, and ptsA mutants. J. Bacteriol. 180, 1729-1740.

93. Miethke, M., et al. (2007) Siderophore-Based Iron Acquisition and Pathogen Control. Microbiology and Molecular Biology Reviews: MMBR 71:413-451.

94. Nautiyal, C. S. (1999) An efficient microbiological growth medium for screening phosphate solubilizing microorganisms. FEMS Microbiol Lett 170, 265-270.

95. Nejad, P. et al. (2000) Endophytic bacteria induce growth promotion and wilt disease suppression in oilseed rape and tomato. Biol Control 18, 208-215.

96. Nübel, U.; et al. Sequence heterogeneties of genes encoding 16S rRNAs in *Paenibacillus polymyxa* detected by temperature gradient gel electrophoresis. J. Bacteriol. 1996, 178, 5636-5643.

97. Omomowo, O. I.; et al. Bacterial and fungal endophytes: Tiny giants with immense beneficial potential for plant growth and sustainable agricultural productivity. Microorganisms 2019, 7, 481.

98. Pal, K. K. et al, 2006. Biological control of plant pathogens. The Plant Health Instructor. Am. Phytopath. Soc., 10.1094/PHI-A-2006-1117-02.

99. Parke, J L., et al. (2001) Diversity of the *Burkholderia cepacia* complex and implications for risk assessment of biological control strains. Annual Review of Phytopathology 39:225 258.

100. Pradhan, S. et al. (2013) Spectrophotometric Determination of Phosphate in Sugarcane Juice, Fertilizer, Detergent and Water Samples by Molybdenum Blue Method. Scientific World, 11:58-62.

101. Qureshi, M. A., et al. (2012) Role of phosphate solubilizing bacteria (PSB) in enhancing p availability and promoting cotton growth. Journal of Animal and Plant Sciences 22, 204-210.

102. Reijnders, L. (2014) Phosphorus resources, their depletion and conservation, a review. Resources, Conservation and Recycling 93, 32-49.

103. Reinhold-Hurek, B., et al, 2011. Living inside plants: bacterial endophytes. Current Opinion in Plant Biology 14, 435-443.

104. Rekanovic, E., et al, 2008. Efficacy of antibiotics and copper compounds in *Erwinia amylovora* control in Serbia. International Society for Horticultural Science (ISHS), Leuven, Belgium, pp. 875-878.

105. Richardson, P. A.; et al. Indications of susceptibility to *Calonectria pseudonaviculata* in som common groundcovers and boxwood companion plants. Plant Dis. 2019.

106. Ridley, G. New plant fungus found in Auckland box hedges (*Buxus*). For. Health News 1998, 77, 1-2.

107. Rodriguez, H., et al, (1999) Phosphate solubilizing bacteria and their role in plant growth promotion. Biotechnol. Adv. 17, 319-339.

108. Romera, F. J., et al, 2019. Induced Systemic Resistance (ISR) and Fe Deficiency Responses in Dicot Plants. Frontiers in Plant Science 10, 287.

109. Rosenblueth, M., et al (2006) Bacterial endophytes and their interactions with hosts. Molecular Plant-Microbe Interactions 19:827-837.

110. Ryan, C.; et al. Susceptibility of *Sarcococca* taxa to boxwood blight by *Calonectria pseudonaviculata*. Proc. South. Nurs. Assoc. Res. Conf. 2018, 62, 64-67.

111. Sajjan, U.S., et al, 1995. Cable (cbl) type II pili of cystic fibrosis-associated *Burkholderia* (*Pseudomonas*) *cepacia*: nucleotide sequence of the cblA major subunit pilin gene and novel morphology of the assembled appendage fibers. Journal of Bacteriology 177, 1030.

112. Santoyo, G., et al, 2016. Plant growth-promoting bacterial endophytes. Microbiological Research 183, 92-99.

113. Santoyo, G., et al. (2012) Mechanisms of biocontrol and plant growth-promoting activity in soil bacterial species of *Bacillus* and *Pseudomonas*: a review. Biocontrol Sci Technol 22, 855-872.

114. Saracchi, M., et al. (2008) Box blight, a new disease of *Buxus* in Italy caused by *Cylindrocladium buxicola*. Journal of Plant Pathology 90:581-584.

115. Saunders, P. Boxwood Guide, 5th ed.; The Saunders Brothers Family: Piney River, VA, USA, 2017; p. 95.

116. Savary, S., et al, 2012. Crop losses due to diseases and their implications for global food production losses and food security. Food Security 4, 519-537.

117. Schikora, A, et al. (2016) Beneficial effects of bacteria-plant communication based on quorum sensing molecules of the N-acyl homoserine lactone group. Plant Mol Biol 90:605-612.

118. Schluenzen, F., et al, 2006. The antibiotic kasugamycin mimics mRNA nucleotides to destabilize tRNA binding and inhibit canonical translation initiation. Nature Structural & Molecular Biology 13, 871-878.

119. Schulz, B., et al, 1999. The endophyte-host interaction: a balanced antagonism? Mycological Research 103, 1275-1283.

120. Schwyn, B. et al. (1987) Universal chemical assay for the detection and determination of siderophores. Anal Biochem 160, 47-56.

121. Seemann, T., (2014) Prokka: rapid prokaryotic genome annotation. Bioinformatics 30, 2068-2069.

122. Shishkoff, N.; etal. Evaluating boxwood susceptibility to *Calonectria pseudonaviculata* using cuttings from the national boxwood collection. Plant Health Progr. 2015, 16, 11-15.

123. Sopheareth, M., et al. (2013) Biocontrol of late blight (*Phytophthora capsici*) disease and growth promotion of pepper by *Burkholderia cepacia* MPC-7. The Plant Pathology Journal 29, 67-76.

124. Suárez-moreno, Z. R., et al, (2012) Common Features of Environmental and Potentially Beneficial Plant-Associated *Burkholderia*. Microb. Ecol. 63, 249-266.

125. Suleman, M., et al, (2018) Phosphate solubilizing bacteria with glucose dehydrogenase gene for phosphorus uptake and beneficial effects on wheat. PLOS ONE 13, e0204408.

126. Tawfik, K. A., et al, Burkholdines 1097 and 1229, potent antifungal peptides from *Burkholderia ambifaria* 2.2n. Organic Letters 12, 664-666.

127. Trân Van, V., et al. (2000) Repeated beneficial effects of rice inoculation with a strain of *Burkholderia vietnamiensis* on early and late yield components in low fertility sulphate acid soils of Vietnam. Plant Soil 218, 273-284.

128. Vandamme, P., et al. (1997) Occurrence of multiple genomovars of *Burkholderia cepacia* in cystic fibrosis patients and proposal of *Burkholderia multivorans* sp. nov. Int J Syst Evol Microbiol 47, 1188-1200.

129. Varela, C. P., Penalta, B. G., Vazquez, J. P. M., and Casal, O. A. (2009) First report of *Cylindrocladium buxicola* on 130. Vitale, A.; et al. *Calonectria* diseases on ornamental plants in Europe and the Mediterranean basin: An overview. J. Plant Pathol. 2013, 95, 463-476.

131. Walker, R., et al (2015, Symbiotic nitrogen fixation in legumes: Perspectives on the diversity and evolution of nodulation by *Rhizobium* and *Burkholderia* species. In Biological Nitrogen Fixation.

132. Weilharter, A., et al. (2011) Complete genome sequence of the plant growth-promoting endophyte *Burkholderia phytofirmans* strain PsJN. J Bacteriol 193, 3383.

133. Yabuuchi, E., et al, (1992) Proposal of *Burkholderia* gen. nov. and transfer of seven species of the genus *Pseudomonas* homology group II to the new genus, with the type species *Burkholderia cepacia* (Palleroni and Holmes 1981) comb. nov. Microbiol. Immunol. 36, 1251-1275.

134. Yang, T., et al, (2014) Chrysanthemyl diphosphate synthase operates in planta as a bifunctional enzyme with chrysanthemol synthase activity. The Journal of biological chemistry 289, 36325-36335.

135. Yang, X. et al. (2018) Biological control of boxwood blight by *Pseudomonas protegens* recovered from recycling irrigation systems. Biol Control 124, 68-73.

136. Yang, X.; et al. Evaluation of biofungicides for control of boxwood blight on boxwood, 2017. Plant Dis. Manag. Rep. 2017, 11, OT023.

137. Yoon, S.-H.; et al. Introducing EzBioCloud: A taxonomically united database of 16S rRNA gene sequences and whole-genome assemblies. Int. J. Syst. Evol. Microbiol. 2017, 67, 1613-1617.

138. Yoshihisa, H., et al (1989) Production of antibiotics by *Pseudomonas cepacia* as an agent for biological control of soilborne plant pathogens. Soi/Biology and Biochemistry 21:723-728.

139. Zhao, Y. (2010) Auxin biosynthesis and its role in plant development. Annu Rev Plant Biol 61, 49-64.

140. Zhao, Y. (2012) Auxin biosynthesis: a simple two-step pathway converts tryptophan to indole-3-acetic acid in plants. Molecular plant 5, 334-338.

SEQUENCE LISTING

The patent contains a lengthy sequence listing. A copy of the sequence listing is available in electronic form from the USPTO web site (https://seqdata.uspto.gov/docdetail?docId=US12616207B2). An electronic copy of the sequence listing will also be available from the USPTO upon request and payment of the fee set forth in 37 CFR 1.19(b)(3).

What is claimed is:

1. A composition comprising a cell-free supernatant produced by culturing a microbial strain comprising a DNA sequence exhibiting at least 99.5% sequence identity to SEQ ID NO. 1 and at least one of SEQ ID NOs. 2-6; and at least one excipient, diluent, or carrier.

2. The composition of claim 1, wherein the at least one excipient, diluent, or carrier comprises a surfactant, a solvent, an emulsifier, a buffer, a cryoprotectant, a salt, a microbial culture medium, a wetting agent, a bulking agent, an anti-caking agent, a thickener, a clay, a mineral, a lipid, a gum, a dye or colorant, a biological waste material, or any combination thereof.

3. The composition of claim 1, wherein the composition further comprises an effective amount of at least one additional active ingredient, wherein the additional active ingredient comprises a fertilizer, a pesticide, an herbicide, or any combination thereof.

4. A method for treating or preventing a plant disease caused by a pathogen, the method comprising applying the composition of claim 1 to a plant or a material in a bed surrounding a plant.

5. The method of claim 4, wherein the composition is applied from about 2 to about 30 days prior to exposure to the pathogen.

6. The method of claim 4, wherein the composition is applied from about 3 hours to about 48 hours after exposure to the pathogen.

7. A method for treating or preventing a plant disease caused by a pathogen, the method comprising applying the composition of claim 1 to at least one environmental component of a plant, wherein the at least one environmental component comprises leaf debris, soil, the plant's rhizosphere, or any combination thereof.

8. The method of claim 4, wherein applying the composition reduces primary inocula by at least 30% after 5 days.

9. The method of claim 4, wherein the pathogen comprises a bacterium, a fungus, an oomycete, or a virus.

10. The method of claim 9, wherein the fungus comprises *Calonectria pseudonaviculata, Alternaria* tenuissium,

*Botrytis cinerea, Collectortrichum acutatum*, Collectortrichum frutticola, Collectortrichum gleosporiodes, Collectortrichum *viniferum, Fusarium* proliferaturm, *Fusarium solani*, or *Volutella* buxi.

11. The method of claim 4, wherein the composition is applied to roots, leaves, fruits, flowers, stems, or seeds of the plant, soil, compost, mulch, leaf litter, sawdust, straw, pine straw, wood chips, gravel, plant growing medium, other material in a bed surrounding the plant, or any combination thereof.

12. The method of claim 4, wherein the plant comprises Fraser fir, *petunia, rhododendron*, annual *vinca*, bell pepper, cucumber, tomato, *hydrangea*, pansy, boxwood, geranium, or *impatiens*.

13. The method of claim 12, wherein the plant pathogen is a fungus and wherein the fungus comprises *Calonectria pseudonaviculata* and the plant comprises boxwood.

14. The method of claim 4, wherein performing the method reduces at least one symptom of the plant disease by at least 50%.

15. The method of claim 14, wherein the at least one symptom comprises leaf yellowing, leaf loss, wilting, dwarfing or hypoplasia, gall formation, mycelium or mold growth, smuts, rusts, sclerotia, tissue necrosis, cankers, blight, rot, hypertrophy, or any combination thereof.

16. The method of claim 4, wherein performing the method reduces transmission of the plant disease by at least 50%.

17. The method of claim 4, wherein the plant pathogen is a fungus and wherein performing the method lyses at least a portion of fungal conidia, causes defects in formed fungal conidia, suppresses mycelial growth, reduces survival of fungal microsclerotia, reduces sporulation, or any combination thereof.

18. The composition of claim 1, wherein the at least one excipient, diluent, or carrier comprises 0.01% polysorbate 20.

* * * * *